US006172278B1

(12) United States Patent
Georgopoulos

(10) Patent No.: US 6,172,278 B1
(45) Date of Patent: Jan. 9, 2001

(54) IKAROS TRANSGENIC CELLS AND MICE

(75) Inventor: Katia Georgopoulos, Cambridge, MA (US)

(73) Assignee: The General Hospital Corporation, Boston, MA (US)

(*) Notice: Under 35 U.S.C. 154(b), the term of this patent shall be extended for 0 days.

(21) Appl. No.: 08/283,300

(22) Filed: Jul. 29, 1994

Related U.S. Application Data

(63) Continuation-in-part of application No. 08/238,212, filed on May 2, 1994, now abandoned, which is a continuation-in-part of application No. 08/121,438, filed on Sep. 14, 1993, now abandoned, which is a continuation-in-part of application No. 07/946,233, filed on Sep. 14, 1992, now abandoned.

(51) Int. Cl.[7] ............................ C12N 15/09; C12N 15/63; C12N 15/00; C12N 5/00

(52) U.S. Cl. ................................ 800/18; 800/14; 800/9; 800/11; 800/10; 800/3; 800/21; 800/22; 800/25; 435/455; 435/463; 435/320.1; 435/325

(58) Field of Search .................................. 800/2, 18, 14, 800/9, 11, 10, 3, 21, 22, 25; 435/172.3, 455, 463, 320.1, 325

(56) References Cited

FOREIGN PATENT DOCUMENTS

WO 94/06814   3/1994  (WO) .
WO 97/09419   3/1997  (WO) .

OTHER PUBLICATIONS

Adams, B. et al. "Pax–5– encodes the transcription factor BSAP and is expressed in B lymphocytes, the developing CNS, and adult testis" *Genes & Development* 6: 1589–1607 (1992).
Akbar, A.N. et al. "A possible role for bcl–2 in regulating T–cell memory—a 'balancing act' between cell death and survival" *Immunology Today* 14(11): 526–531 (1993).
Ardavin, C. et al. "Thymic dendritic cells and T cells develop simultaneously in the thymus from a common precursor population" *Nature* 362; 761–763 (1993).
Asarnow, D.M. et al. "Limited Diversity of γδ Antigen Receptor Genes of Thy–1+ Dendritic Epidermal Cells" *Cell* 55: 837–847 (Dec. 2, 1988).
Beg, A.A. et al. "The IκB proteins: multifunctional regulators of Rel/NF–κB transcription factors" *Genes & Development* 7: 2064–2070 (1993).
Bigby, M. et al. "Ratio of Langerhan Cells to Thy–1+ Dendritic Epidermal Cells in Murine Epidermis Influences the Intensity of Contact Hypersensitivity" *The Journal of Investigative Dermatology* 89(5): 495–499 (Nov. 1987).
Boise, L.H. et al. "bcl–x, a bcl–2–Related Gene that Functions as a Dominant Regulator of Apoptotic Cell Death" *Cell* 74: 597–608 (1993).
Bours, V. et al. "The Oncoprotein Bcl–3 Directly Transactivates through κB Motifs via Association with DNA–Binding p50B Homodimers" *Cell* 72: 729–739 (1993).

Cepko, C.L. et al "Construction and Applications of a Highly Transmissible Murine Retrovirus Shuttle Vector" *Cell* 37: 1053–1062 (1984).
Clevers, H.C. et al. "Transcription factors in early T–cell development" *Immunology Today* 14(2): 591–596 (1993).
Connelly, C.S. et al. "The Role of Transgenic Animals in the Analysis of Various Biological Aspects of Normal and Pathologic States" *Experimental Cell Research* 183: 257–276 (1989).
Delwel, R. et al. Four of the Seven Zinc Fingers of the Evi–1 Myeloid–Transforming Gene Are Required for Sequence–Specific Binding to GA(C/T)AAGA(T/C)AAGATAA, *Molecular and Cellular Biology* 13(7): 4291–4300 (1993).
Ehlich, A. et al. "Immunoglobulin Heavy and Light Chain Genes Rearrange Independently at Early Stages of B Cell Development" *Cell* 72: 695–704 (1993).
Fife, A. et al. "Gram negative septicaemia diagnosed on peripheral blood smear appearances" *Journal of Clinical Pathology* 47: 82–84 (1994).
Fleming, W.H. et al. "Functional Heterogeneity Is Associated with the Cell Cycle Status of Murine Hematopoietic Stem Cells" *J. Cell Biol.* 122: 897–902 (1993).
Franzoso, G. et al. "The oncoprotein Bcl–3 can facilitate NF–κB–mediated transactivation by removing inhibiting p50 homodimers from select κB sites" *The EMBO Journal*, vol. 12, No. 10 3893–3901 (1993).
Furley, A.J. et al. "Developmentally Regulated Rearrangement and Expression of Genes Encoding the T Cell Receptor–T3 Complex" *Cell*, vol. 46: 75–87 (Jul. 1986).
Garni–Wagner, B.A. et al. "Natural Killer Cells in the Thymus" *The Journal of Immunology* 144 (3): 796–803 (1990).
Georgopoulos, K. "Ikaros an Early Lymphoid Restricted Regulatory Protein Putative Mediator For T Cell Specification" *Biochem. Suppl.* 0 (17 Part A): 158, B 631 (1993).
Georgopoulos, K. et al. "Functionally Distinct Isoforms of the CRE–BP DNA–Binding Protein Mediate Activity of a T–Cell–Specific Enhancer" *Molecular and Cellular Biology* 12(2): 747–757 (Feb. 1992).
Georgopoulos, K. et al. "Ikaros, an Early Lymphoid–Specific Transcription Factor and a Putative Mediator for T Cell Commitment" *Science* 258: 808–812 (Oct. 1992).
Georgopoulos, K. et al. "A T cell–specific enhancer is located in a DNase I–hypersensitive area at the 3' end of the CD3–δ gene" *The EMBO Journal* 7(8): 2401–2407 (Aug. 1988).
Georgopoulos, K. et al. "Tissue–specific nuclear facors mediate expression of the CD3δ gene during T cell development" *The EMBO Journal* 9(1): 109–115 (Jan. 1990).

(List continued on next page.)

Primary Examiner—Jasemine Chambers
Assistant Examiner—Jill D. Martin
(74) Attorney, Agent, or Firm—Fish & Richardson, P.C.

(57) ABSTRACT

Transgenic cells, transgenic mice having an Ikaros transgene and methods for the use thereof.

11 Claims, 16 Drawing Sheets

OTHER PUBLICATIONS

Godfrey, D.I. and A. Zlotnik "Control points in early T–cell development" *Immunology Today* 14(11): 547–553 (1993).

Gogos, J.A. et al. "Sequence Discrimination by Alternatively Spliced Isoforms of a DNA Binding Zinc Finger Domain" *Science* 257: 1951–1955 (1992).

Hackett, Jr., J. et al. "Origin and Differentiation of Natural Killer Cells" *The Journal of Immunology* 136(8): 3124–3131 (1986).

Hackett, Jr., J. et al. "Transplantable progenitors of natural killer cells are distinct from those of T and B lymphocytes" *Proc. Natl. Acad. Sci USA* 83: 3427–3431 (1986).

Hardy, R.R. et al. "Resolution and Characterization of Pro–B and Pre–Pro–B Cell Stages in Normal Mouse Bone Marrow" *J. Exp. Med.* 173: 1213–1225 (May 1991).

Havran, W.L. and J.P. Allision "Origin of Thy–1+ dendritic epidermal cells of adult mice from fetal thymic precursors" *Nature* 344: 68–70 (1990).

Havran, W.L. et al. "Developmentally ordered appearance of thymocytes expressing different T–cells antigen receptors" *Nature* 335: 443–445 (1988).

Havran, W.L. et al. "Limited diversity of T–cell receptor γ–chain expression of murine Thy–1+ dendritic epidermal cells revealed by Vγ3–specific monoclonal antibody" *Proc. Natl. Acad. Sci. USA* 86: 4185–4189 (1989).

Haynes, B. et al. "Ontogeny of T–cell precursors: a model for the initial stages of human T–cell development" *Immunology Today* 10(3): 87–90 (1989).

Hestdal, K. et al. "Characterization and Regulation of RB6–8C5 Antigen Expression on Murine Bone Marrow Cells" *J. Immunol.* 147(1): 22–28 (Jul. 1, 1991).

Ho, I.–C. et al. "Human GATA–3: a lineage–restected transcription factor that regulates the expression of the T cell receptor α gene" *The EMBO Journal* 10(5): 1187–1192 (1991).

Ho, I.–C. et al. "Sequence–Specific Binding of Human Ets–1 to the T Cell Receptor α Gene Enhancer" *Science* 250: 814–818 (1990).

Hsu, T. et al. "Multiple Zinc Finger Forms Resulting from Developmentally Regulated Alternative Splicing of a Transcription Factor Gene" *Science* 257: 1946–1950 (1992).

Ikuta, K. et al. "A Developmental Switch in Thymic Lymphocyte Maturation Potential Occurs at the Level of Hematopoietic Stem Cells" *Cell* 62: 863–874 (1990).

Ikuta, K. et al. "Lymphocyte Development From Stem Cells" *Annu. Rev. Immunol.* 10: 759–783 (1992).

Jiang, J. and M. Levine "Binding Affinities and Cooperative Interactions with bHLH Activators Delimit Threshold Responses to the Dorsal Gradient Morphogen" *Cell* 72: 741–752 (1993).

Juhlin, L. and W.B. Shelley "New Staining Techniques for the Langerhans Cell" *Acta Dermatovener* 57: 289–296 (1977).

Kang, S.–M. et al. "NF–κB Subunit Regulation in Nontransformed CD4+ T Lymphocytes" *Science* 256: 1452–1456 (1992).

Karasuyama, H. et al. "The Expression of $V_{pre-B}/\lambda 5$ Surrogate Light Chain in Early Bone Marrow Precursor B Cells of Normal and B Cell–Deficient Mutant Mice" *Cell* 77: 133–143 (Apr. 8, 1994).

Lagasse, E. and I.L. Weissman "BCL–2 Transgene Inhibits Neutrophils Cell Death But Not Their Engulfment By Microphages" *J. Biochem.* 0 (Suppl. 17D): 168 (Mar. 13–31, 1993).

Leiden, J.M. et al. "Transcriptional regulation during T–cell development: The α TCR gene as a molecular model" *Immunology Today* 13(1): 22–30 (Jan. 1992).

Lenardo, M.J. and D. Baltimore "NF–κB: A Pleiotropic Mediator of Inducible and Tissue–Specific Gene Control" *Cell* 58: 227–229 (1989).

Li, E. et al. "Targeted Mutation of the DNA Methyltransferase Gene Results in Embryonic Lethality" *Cell* 69: 915–926 (1992).

Li, Y.–S. et al. "The Regulated Expression of B Lineage Associated Genes during B Cell Differentiation in Bone Marrow and Fetal Liver" *J. Exp. Med.* 178: 951–960 (1993).

Liang, P. et al. "Distribution and cloning of eukaryotic mRNAs by means of differential display: refinements and optimization" *Nucleic Acids Research* 21(14): 3269–3275 (1993).

Mann, R. et al. "Construction of a Retrovirus Packaging Mutant and Its Use to Produce Helper–Free Defective Retrovirus" *Cell* 33: 153–159 (1993).

Martin, D.I.K. et al. "Expression of an erythroid transcription factor in megakaryocytic and mast cell lineages" *Nature* 344: 444–447 (1990).

McDonnell, T.J. et al. "bcl–2–Immunoglobulin Transgenic Mice Demonstrate Extended B Cell Survival and Follicular Lymphoproliferation" *Cell* 57: 79–88 (1989).

McDonnell, T.J. et al. "Progression from lymphoid hyperplasia to high–grade malignant lymphoma in mice transgenic for the t(14;18)" *Nature* 349: 254–256 (1991).

Metcalf, D. "The molecular control of cell division, differentiation commitment and maturation in haemopoietic cells" *Nature* 339:27–30 (1989).

Mombaerts, P. et al. "RAG–1–Deficient Mice Have No Mature B and T Lymphocytes" *Cell* 68: 869–877 (1992).

Mucenski, M.L. et al. "A Functional c–myb Gene is Required for Normal Murine Fetal Hepatic Hematopoiesis" *Cell* 65: 677–689 (1991).

Oltvai, Z.N. et al. "Bcl–2 Heterodimerizes In Vivo with a Conserved Homolog, Bax, That Accelerates Programed Cell Death" *Cell* 74: 609–619 (1993).

Oosterwegel, M. et al. "Cloning of Murine TCF–1, a T Cell–specific Transcription Factor Interacting with Functional Motifs in the CD3–ε and T Cell Receptor α Enhancers" *J. Exp. Med.* 173: 1133–1142 (May 1991).

Oosterwegel, M. et al. "Differential expression of the HMG box factors TCF–1 and LEF–1 during murine embryogenesis" *Development* 118: 439–448 (1993).

Philpott, K.L. et al. "Lymphoid Development in Mice Congenitally Lacking T Cell Receptor αβ–Expressing Cells" *Science* 256: 1448–1452 (Jun. 5, 1992).

Raulet, D.H. et al. "Control of γδ T–Cell Development" *Immunological Reviews* 120:185–204 (1991).

Read, D. and J.L. Manley "Alternatively spliced transcripts of the *Drosophila* tramtrack gene encode zinc finger proteins with distinct DNA binding specificities" *The EMBO Journal* 11(3): 1035–1044 (1992).

Rodewald, H.–R. et al. "A Population of Early Fetal Thymocytes Expressing FcγRII/III Contains Precursors of T Lymphocytes and Natural Killer Cells" *Cell* 69: 139–150 (1992).

Rolink, A. and F. Melchers "Molecular and Cellular Origins of B Lymphocyte Diversity" *Cell* 66: 1061–1094 (1991).

Rudnicki, M.A. et al. "Inactivation of MyoD in Mice Leads to Up–Regulation of the Myogenic HLH Gene Myf–5 and Results in Apparently Normal Muscle Development" *Cell* 71: 383–390 (1992).

Sawyers, C.L. et al. "Leukemia and the Disruption of Normal Hematopoiesis" *Cell* 64: 337–350 (1991).

Sentman, C.L. et al. "bcl–2 Inhibits Multiple Forms of Apoptosis but Not Negative Selection in Thymosytes" *Cell* 67: 879–888 (1991).

Shinkai, Y. et al. "RAG–2–Deficient Mice Lack Mature Lymphocytes Owing to Inability to Initiate V(D)J Rearrangement" *Cell* 68: 855–867 (1992).

Singh, H. et al. "Molecular Cloning of an Enhancer Binding Protein: Isolation by Screening of an Expression Library with a Recognition Site DNA" *Cell* 52: 415–423 (Feb. 12, 1988).

Skeath, J.B. et al. "Gene regulation in two dimensions" the proneural achaete and scute genes are controlled by combinations of axis–patterning genes through a common intergenic control region *Genes & Development* 6: 2606–2619 (1992).

Spangrude, G.J. "Enrichment of murine haemopoietic stem cells: diverging roads" *Immunology Today* 10(10): 344–350 (1989).

Spangrude, G.J. et al. "Purification and Characterization of Mouse Hematopoeitic Stem Cells" *Science* 241:58–62 (Jul. 1, 1988).

Spanopoulou, E. et al. "Functional immunoglobulin transgenes guide ordered B–cell differentiation in Rag–1–deficient mice" *Genes & Development* 8: 1030–1042 (1994).

Travis, A. et al. "LEF–1, a gene encoding a lymphoid–specific with protein, an HMG domain, regulates T–cell receptor α enhancer function" *Genes & Development* 5: 880–894 (1991).

Turner, Jr., C.A. et al. "Blimp–1, a Novel Zinc Finger–Containing Protein that Can Drive the Maturation of B Lymphocytes into Immunoglobulin–Secreting Cells" *Cell* 77: 297–306 (Apr. 22, 1994).

van de Wetering, M. et al. "Identification and cloning of TCF–1 a T lymphocyte–specific transcription factor containing a sequence–specific HMG box" *The EMBO Journal* 10(1): 123–132 (1991).

von Boehmer, H. "The Developmental Biology of T Lymphocytes" *Ann. Rev. Immunol.* 6: 309–326 (1988).

Waterman, M.L. et al. "A thymus–specific member of the HMG protein family regulates the human T cell receptor Cα enhancer" *Genes & Development* 5: 656–669 (1991).

Weintraub, H. "The MyoD Family and Myogenesis: Redundancy, Networks, and Thresholds" *Cell* 75: 1241–1244 (Dec. 31, 1993).

Xu, Y. et al. "LH–2: A LIM/homeodomain gene expressed in developing lymphocytes and neural cells" *Proc. Natl. Acad Sci. USA* 90: 227–231 (1993).

Yokoyama, W.M. "Flow Cytometry Analysis Using the Becton Dickinson FACScan" in *Current Protocols in Immunology*, J.E. Coligan et al. (Eds.), Brooklyn, NY: Greene Publishing Associates, 5.4.1–5.4.14 (1992).

Zervos, A.S. et al. "Mxi1, a Protein that Specifically Interacts with Max to Bind Myc–Max Recognition Sites" *Cell* 72: 223–232 (1993).

Molnar et al., "The Ikaros gene encodes a family of functionally diverse zinc finger DNA–binding proteins": Mol. and Cell. Biology 14:8292–8303 (1994).

Winandy et al., ":A dominant mutation in the Ikaros gene leads to rapid development of leukemia and lymphoma", Cell 83:289–299 (1995).

Georgopoulos, K. et al. "The Ikaros Gene is Required for the Development of all Lymphoid Lineages" *Cell* 79, 143–156 (1994).

Bradley et al., Biotechnology, vol. 10, pp. 534–539, May, 1992.*

Mullins et al., J. Clin. Invest., vol. 98, No. 11, pp. S37–S40, 1996.

Mullins et al., J. Clin. Invest., vol. 98, No. 11, pp. S37–S40, 1996.

Seamark, Reproduction, Fertility and Development, vol. 6, No. 5, pp. 653–657, 1994.

Moreadith et al., J. Mol. Med., vol. 75, pp. 208–216, 1997.

* cited by examiner

```
AATTCGTTCT ACCTTCTCTG AACCCCAGTG GTGTGTCAAG GCCGGACTGG GAGCTTGGGG         60

GAAGAGGAAG AGGAAGAGGA ATCTGCGGCT CATCCAGGGA TCAGGGTCCT TCCCAAGTGG        120

CCACTCAGAG GGGACTCAGA GCAAGTCTAG ATTTGTGTGG CAGAGAGAGA CAGCTCTCGT        180

TTGGCCTTGG GGAGGCACAA GTCTGTTGAT AACCTGAAGA CA                          222
```

| | | | | | | | | | | | | | | | | |
|---|---|---|---|---|---|---|---|---|---|---|---|---|---|---|---|---|
| ATG | GAT | GTC | GAT | GAG | GGT | CAA | GAC | ATG | TCC | CAA | GTT | TCA | GGA | AAG | GAG | 270 |
| Met | Asp | Val | Asp | Glu | Gly | Gln | Asp | Met | Ser | Gln | Val | Ser | Gly | Lys | Glu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| AGC | CCC | CCA | GTC | AGT | GAC | ACT | CCA | GAT | GAA | GGG | GAT | GAG | CCC | ATG | CCT | 318 |
| Ser | Pro | Pro | Val | Ser | Asp | Thr | Pro | Asp | Glu | Gly | Asp | Glu | Pro | Met | Pro | |
| | | | 20 | | | | | 25 | | | | | 30 | | | |

| | | | | | | | | | | | | | | | | |
|---|---|---|---|---|---|---|---|---|---|---|---|---|---|---|---|---|
| GTC | CCT | GAG | GAC | CTG | TCC | ACT | ACC | TCT | GGA | GCA | CAG | CAG | AAC | TCC | AAG | 366 |
| Val | Pro | Glu | Asp | Leu | Ser | Thr | Thr | Ser | Gly | Ala | Gln | Gln | Asn | Ser | Lys | |
| | | 35 | | | | | 40 | | | | | 45 | | | | |

| | | | | | | | | | | | | | | | | |
|---|---|---|---|---|---|---|---|---|---|---|---|---|---|---|---|---|
| AGT | GAT | CGA | GGC | ATG | GGT | GAA | CGG | CCT | TTC | CAG | TGC | AAC | CAG | TCT | GGG | 414 |
| Ser | Asp | Arg | Gly | Met | Gly | Glu | Arg | Pro | Phe | Gln | Cys | Asn | Gln | Ser | Gly | |
| | | 50 | | | | 55 | | | | | 60 | | | | | |

| | | | | | | | | | | | | | | | | |
|---|---|---|---|---|---|---|---|---|---|---|---|---|---|---|---|---|
| GCC | TCC | TTT | ACC | CAG | AAA | GGC | AAC | CTC | CTG | CGG | CAC | ATC | AAG | CTG | CAC | 462 |
| Ala | Ser | Phe | Thr | Gln | Lys | Gly | Asn | Leu | Leu | Arg | His | Ile | Lys | Leu | His | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| TCG | GGT | GAG | AAG | CCC | TTC | AAA | TGC | CAT | CTT | TGC | AAC | TAT | GCC | TGC | CGC | 510 |
| Ser | Gly | Glu | Lys | Pro | Phe | Lys | Cys | His | Leu | Cys | Asn | Tyr | Ala | Cys | Arg | |
| | | | | 85 | | | | | 90 | | | | | 95 | | |

| | | | | | | | | | | | | | | | | |
|---|---|---|---|---|---|---|---|---|---|---|---|---|---|---|---|---|
| CGG | AGG | GAC | GCC | CTC | ACC | GGC | CAC | CTG | AGG | ACG | CAC | TCC | GTT | GGT | AAG | 558 |
| Arg | Arg | Asp | Ala | Leu | Thr | Gly | His | Leu | Arg | Thr | His | Ser | Val | Gly | Lys | |
| | | | | 100 | | | | | 105 | | | | | 110 | | |

| | | | | | | | | | | | | | | | | |
|---|---|---|---|---|---|---|---|---|---|---|---|---|---|---|---|---|
| CCT | CAC | AAA | TGT | GGA | TAT | TGT | GGC | CGG | AGC | TAT | AAA | CAG | CGA | AGC | TCT | 606 |
| Pro | His | Lys | Cys | Gly | Tyr | Cys | Gly | Arg | Ser | Tyr | Lys | Gln | Arg | Ser | Ser | |
| | | 115 | | | | | 120 | | | | | 125 | | | | |

| | | | | | | | | | | | | | | | | |
|---|---|---|---|---|---|---|---|---|---|---|---|---|---|---|---|---|
| TTA | GAG | GAG | CAT | AAA | GAG | CGA | TGC | CAC | AAC | TAC | TTG | GAA | AGC | ATG | GGC | 654 |
| Leu | Glu | Glu | His | Lys | Glu | Arg | Cys | His | Asn | Tyr | Leu | Glu | Ser | Met | Gly | |
| | | 130 | | | | | 135 | | | | | 140 | | | | |

| | | | | | | | | | | | | | | | | |
|---|---|---|---|---|---|---|---|---|---|---|---|---|---|---|---|---|
| CTT | CCG | GGC | GTG | TGC | CCA | GTC | ATT | AAG | GAA | GAA | ACT | AAC | CAC | AAC | GAG | 702 |
| Leu | Pro | Gly | Val | Cys | Pro | Val | Ile | Lys | Glu | Glu | Thr | Asn | His | Asn | Glu | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ATG | GCA | GAA | GAC | CTG | TGC | AAG | ATA | GGA | GCA | GAG | AGG | TCC | CTT | GTC | CTG | 750 |
| Met | Ala | Glu | Asp | Leu | Cys | Lys | Ile | Gly | Ala | Glu | Arg | Ser | Leu | Val | Leu | |
| | | | | 165 | | | | | 170 | | | | | 175 | | |

| | | | | | | | | | | | | | | | | |
|---|---|---|---|---|---|---|---|---|---|---|---|---|---|---|---|---|
| GAC | AGG | CTG | GCA | AGC | AAT | GTC | GCC | AAA | CGT | AAG | AGC | TCT | ATG | CCT | CAG | 798 |
| Asp | Arg | Leu | Ala | Ser | Asn | Val | Ala | Lys | Arg | Lys | Ser | Ser | Met | Pro | Gln | |
| | | | | 180 | | | | | 185 | | | | | 190 | | |

FIG. 1A

```
AAA TTT CTT GGA GAC AAG TGC CTG TCA GAC ATG CCC TAT GAC AGT GCC    846
Lys Phe Leu Gly Asp Lys Cys Leu Ser Asp Met Pro Tyr Asp Ser Ala
            195                 200                 205

AAC TAT GAG AAG GAG GAT ATG ATG ACA TCC CAC GTG ATG GAC CAG GCC    894
Asn Tyr Glu Lys Glu Asp Met Met Thr Ser His Val Met Asp Gln Ala
        210                 215                 220

ATC AAC AAT GCC ATC AAC TAC CTG GGG GCT GAG TCC CTG CGC CCA TTG    942
Ile Asn Asn Ala Ile Asn Tyr Leu Gly Ala Glu Ser Leu Arg Pro Leu
225                 230                 235                 240

GTG CAG ACA CCC CCC GGT AGC TCC GAG GTG GTG CCA GTC ATC AGC TCC    990
Val Gln Thr Pro Pro Gly Ser Ser Glu Val Val Pro Val Ile Ser Ser
                245                 250                 255

ATG TAC CAG CTG CAC AAG CCC CCC TCA GAT GGC CCC CCA CGG TCC AAC   1038
Met Tyr Gln Leu His Lys Pro Pro Ser Asp Gly Pro Pro Arg Ser Asn
            260                 265                 270

CAT TCA GCA CAG GAC GCC GTG GAT AAC TTG CTG CTG CTG TCC AAG GCC   1086
His Ser Ala Gln Asp Ala Val Asp Asn Leu Leu Leu Leu Ser Lys Ala
        275                 280                 285

AAG TCT GTG TCA TCG GAG CGA GAG GCC TCC CCG AGC AAC AGC TGC CAA   1134
Lys Ser Val Ser Ser Glu Arg Glu Ala Ser Pro Ser Asn Ser Cys Gln
290                 295                 300

GAC TCC ACA GAT ACA GAG AGC AAC GCG GAG GAA CAG CGC AGC GGC CTT   1182
Asp Ser Thr Asp Thr Glu Ser Asn Ala Glu Glu Gln Arg Ser Gly Leu
305                 310                 315                 320

ATC TAC CTA ACC AAC CAC ATC AAC CCG CAT GCA CGC AAT GGG CTG GCT   1230
Ile Tyr Leu Thr Asn His Ile Asn Pro His Ala Arg Asn Gly Leu Ala
                325                 330                 335

CTC AAG GAG GAG CAG CGC GCC TAC GAG GTG CTG AGG GCG GCC TCA GAG   1278
Leu Lys Glu Glu Gln Arg Ala Tyr Glu Val Leu Arg Ala Ala Ser Glu
            340                 345                 350

AAC TCG CAG GAT GCC TTC CGT GTG GTC AGC ACG AGT GGC GAG CAG CTG   1326
Asn Ser Gln Asp Ala Phe Arg Val Val Ser Thr Ser Gly Glu Gln Leu
        355                 360                 365

AAG GTG TAC AAG TGC GAA CAC TGC CGC GTG CTC TTC CTG GAT CAC GTC   1374
Lys Val Tyr Lys Cys Glu His Cys Arg Val Leu Phe Leu Asp His Val
370                 375                 380

ATG TAT ACC ATT CAC ATG GGC TGC CAT GGC TGC CAT GGC TTT CGG GAT   1422
Met Tyr Thr Ile His Met Gly Cys His Gly Cys His Gly Phe Arg Asp
385                 390                 395                 400

CCC TTT GAG TGT AAC ATG TGT GGT TAT CAC AGC CAG GAC AGG TAC GAG   1470
Pro Phe Glu Cys Asn Met Cys Gly Tyr His Ser Gln Asp Arg Tyr Glu
                405                 410                 415
```

FIG. 1B

```
TTC TCA TCC CAT ATC ACG CGG GGG GAG CAT CGT TAC CAC CTG AGC         1515
Phe Ser Ser His Ile Thr Arg Gly Glu His Arg Tyr His Leu Ser
            420                 425                 430

TAAACCCAGC CAGGCCCCAC TGAAGCACAA AGATAGCTGG TTATGCCTCC TTCCCGGCAG   1575

CTGGACCCAC AGCGGACAAT GTGGGAGTGG ATTTGCAGGC AGCATTTGTT CTTTTATGTT   1635

GGTTGTTTGG CGTTTCATTT GCGTTGGAAG ATAAGTTTTT AATGTTAGTG ACAGGATTGC   1695

ATTGCATCAG CAACATTCAC AACATCCATC CTTCTAGCCA GTTTTGTTCA CTGGTAGCTG   1755

AGGTTTCCCG GATATGTGGC TTCCTAACAC TCT                                1788
```

(SEQ.ID.NO:1)

FIG. 1C

```
AAT GTT AAA GTA GAG ACT CAG AGT GAT GAA GAG AAT GGG CGT GCC TGT        48
Asn Val Lys Val Glu Thr Gln Ser Asp Glu Glu Asn Gly Arg Ala Cys
 1           5                  10                  15

GAA ATG AAT GGG GAA GAA TGT GCG GAG GAT TTA CGA ATG CTT GAT GCC        96
Glu Met Asn Gly Glu Glu Cys Ala Glu Asp Leu Arg Met Leu Asp Ala
             20                  25                  30

TCG GGA GAG AAA ATG AAT GGC TCC CAC AGG GAC CAA GGC AGC TCG GCT       144
Ser Gly Glu Lys Met Asn Gly Ser His Arg Asp Gln Gly Ser Ser Ala
         35                  40                  45

TTG TCG GGA GTT GGA GGC ATT CGA CTT CCT AAC GGA AAA CTA AAG TGT       192
Leu Ser Gly Val Gly Gly Ile Arg Leu Pro Asn Gly Lys Leu Lys Cys
     50                  55                  60

GAT ATC TGT GGG ATC ATT TGC ATC GGG CCC AAT GTG CTC ATG GTT CAC       240
Asp Ile Cys Gly Ile Ile Cys Ile Gly Pro Asn Val Leu Met Val His
 65                  70                  75                  80

AAA AGA AGC CAC ACT GGA GAA CGG CCC TTC CAG TGC AAT CAG TGC GGG       288
Lys Arg Ser His Thr Gly Glu Arg Pro Phe Gln Cys Asn Gln Cys Gly
             85                  90                  95

GCC TCA TTC ACC CAG AAG GGC AAC CTG CTC CGG CAC ATC AAG CTG CAT       336
Ala Ser Phe Thr Gln Lys Gly Asn Leu Leu Arg His Ile Lys Leu His
            100                 105                 110

TCC GGG GAG AAG CCC TTC AAA TGC CAC CTC TGC AAC TAC GCC TGC CGC       384
Ser Gly Glu Lys Pro Phe Lys Cys His Leu Cys Asn Tyr Ala Cys Arg
        115                 120                 125

CGG AGG GAC GCC CTC ACT GGC CAC CTG AGG ACG CAC TCC GTT GGT AAA       432
Arg Arg Asp Ala Leu Thr Gly His Leu Arg Thr His Ser Val Gly Lys
    130                 135                 140

CCT CAC AAA TGT GGA TAT TGT GGC CGA AGC TAT AAA CAG CGA ACG TCT       480
Pro His Lys Cys Gly Tyr Cys Gly Arg Ser Tyr Lys Gln Arg Thr Ser
145                 150                 155                 160

TTA GAG GAA CAT AAA GAG CGC TGC CAC AAC TAC TTG GAA AGC ATG GGC       528
Leu Glu Glu His Lys Glu Arg Cys His Asn Tyr Leu Glu Ser Met Gly
                165                 170                 175

CTT CCG GGC ACA CTG TAC CCA GTC ATT AAA GAA GAA ACT AAG CAC AGT       576
Leu Pro Gly Thr Leu Tyr Pro Val Ile Lys Glu Glu Thr Lys His Ser
            180                 185                 190

GAA ATG GCA GAA GAC CTG TGC AAG ATA GGA TCA GAG AGA TCT CTC GTG       624
Glu Met Ala Glu Asp Leu Cys Lys Ile Gly Ser Glu Arg Ser Leu Val
        195                 200                 205

CTG GAC AGA CTA GCA AGT AAT GTC GCC AAA CGT AAG AGC TCT ATG CCT       672
Leu Asp Arg Leu Ala Ser Asn Val Ala Lys Arg Lys Ser Ser Met Pro
    210                 215                 220

CAG AAA TTT CTT GGG GAC AAG GGC CTG TCC GAC ACG CCC TAC GAC AGT       720
Gln Lys Phe Leu Gly Asp Lys Gly Leu Ser Asp Thr Pro Tyr Asp Ser
225                 230                 235                 240
```

FIG. 2A

```
GCC ACG TAC GAG AAG GAG AAC GAA ATG ATG AAG TCC CAC GTG ATG GAC       768
Ala Thr Tyr Glu Lys Glu Asn Glu Met Met Lys Ser His Val Met Asp
            245                 250                 255

CAA GCC ATC AAC AAC GCC ATC AAC TAC CTG GGG GCC GAG TCC CTG CGC       816
Gln Ala Ile Asn Asn Ala Ile Asn Tyr Leu Gly Ala Glu Ser Leu Arg
            260                 265                 270

CCG CTG GTG CAG ACG CCC CCG GGC GGT TCC GAG GTG GTC CCG GTC ATC       864
Pro Leu Val Gln Thr Pro Pro Gly Gly Ser Glu Val Val Pro Val Ile
            275                 280                 285

AGC CCG ATG TAC CAG CTG CAC AGG CGC TCG GAG GGC ACC CCG CGC TCC       912
Ser Pro Met Tyr Gln Leu His Arg Arg Ser Glu Gly Thr Pro Arg Ser
            290                 295                 300

AAC CAC TCG GCC CAG GAC AGC GCC GTG GAG TAC CTG CTG CTG CTC TCC       960
Asn His Ser Ala Gln Asp Ser Ala Val Glu Tyr Leu Leu Leu Leu Ser
305                 310                 315                 320

AAG GCC AAG TTG GTG CCC TCG GAG CGC GAG GCG TCC CCG AGC AAC AGC      1008
Lys Ala Lys Leu Val Pro Ser Glu Arg Glu Ala Ser Pro Ser Asn Ser
            325                 330                 335

TGC CAA GAC TCC ACG GAC ACC GAG AGC AAC AAC GAG GAG CAG CGC AGC      1056
Cys Gln Asp Ser Thr Asp Thr Glu Ser Asn Asn Glu Glu Gln Arg Ser
            340                 345                 350

GGT CTT ATC TAC CTG ACC AAC CAC ATC GCC CGA CGC GCG CAA CGC GTG      1104
Gly Leu Ile Tyr Leu Thr Asn His Ile Ala Arg Arg Ala Gln Arg Val
            355                 360                 365

TCG CTC AAG GAG GAG CAC CGC GCC TAC GAC CTG CTG CGC GCC GCC TCC      1152
Ser Leu Lys Glu Glu His Arg Ala Tyr Asp Leu Leu Arg Ala Ala Ser
            370                 375                 380

GAG AAC TCG CAG GAC GCG CTC CGC GTG GTC AGC ACC AGC GGG GAG CAG      1200
Glu Asn Ser Gln Asp Ala Leu Arg Val Val Ser Thr Ser Gly Glu Gln
385                 390                 395                 400

ATG AAG GTG TAC AAG TGC GAA CAC TGC CGG GTG CTC TTC CTG GAT CAC      1248
Met Lys Val Tyr Lys Cys Glu His Cys Arg Val Leu Phe Leu Asp His
            405                 410                 415

GTC ATG TAC ACC ATC CAC ATG GGC TGC CAC GGC TTC CGT GAT CCT TTT      1296
Val Met Tyr Thr Ile His Met Gly Cys His Gly Phe Arg Asp Pro Phe
            420                 425                 430

GAG TGC AAC ATG TGC GGC TAC CAC AGC CAG GAC CGG TAC GAG TTC TCG      1344
Glu Cys Asn Met Cys Gly Tyr His Ser Gln Asp Arg Tyr Glu Phe Ser
            435                 440                 445

TCG CAC ATA ACG CGA GGG GAG CAC CGC TTC CAC ATG AGC TAA              1386
Ser His Ile Thr Arg Gly Glu His Arg Phe His Met Ser
450                 455                 460
```

FIG. 2B (SEQ.ID.NO:2)

US 6,172,278 B1

IKAROS TRANSGENIC CELLS AND MICE

This application is a continuation-in-part of U.S. Ser. No. 08/238,212, filed May 2, 1994, now abandoned, which is a continuation-in-part of U.S. Ser. No. 08/121,438, filed Sep. 14, 1993, now abandoned which is a continuation-in-part of U.S. Ser. No. 07/946,233, filed Sep. 14, 1992, now abandoned, all of which are hereby incorporated by reference.

BACKGROUND OF THE INVENTION

The invention relates to transgenic cells and animals having an Ikaros transgene and methods, e.g., drug screening, or immunological assay methods, using such cells or animals.

The generation of the T cell repertoire from a progenitor stem cell proceeds through a differentiation pathway in which the later intrathymic steps are well documented while the early extrathymic events are only poorly characterized. One of the earliest definitive T cell differentiation markers is the CD3δ gene of the CD3/TCR complex.

SUMMARY OF THE INVENTION

The Ikaros locus is a master regulatory locus which is intricately intertwined with the regulation of hematopoietic development. The Ikaros locus is also expressed in certain nervous tissue and is active in the regulation of the cell cycle. It is active at various times in development and exerts an extremely pleiotropic hematopoietic development phenotype. E.g., as is discussed below, and in copending applications U.S. Ser. No. 08/238,212, U.S. Ser. No. 08/121,438, and U.S. Ser. No. 07/946,233, the Ikaros gene is characterized by a complex and striking pattern of expression in terms of tissue-specificity, is temporally regulated, and is regulated in terms of the profile of isoform expression. All of these observations are consistent with a gene which provides critical developmental control at a number of points in development. The phenotypes of Ikaros transgenic animals of the invention confirm the fundamental and multifaceted role of the Ikaros gene. For example, mice which are heterozygotic for a deletion of portions of exons 3 and 4 (which encode a region involved in DNA binding), develop extremely aggressive lymphomas. Initial data suggest that human lymphoma tissue often exhibit chromosomal aberrations involving Ikaros. Homozygotes for the exon 3/4 deletion are poorly viable. Transgenic mice with a different deletion, a deletion of exon 7 (which is believed to be active in activation and dimerization of the Ikaros gene product) exhibit a very different phenotype. Mice which are heterozygous for an exon 7 deletion are healthy. Mice which are homozygous for an exon 7 deletion have no B cells, no NK cells, and no γδ T cells. While T cells are present, the populations of $CD4^+/CD8^+$, $CD4^+/CD8^-$, and $CD4^-/CD8^+$ are skewed (the proportion of $CD4^+/CD8^+$ cells is decreased relative to wild type, the proportion of $CD4^+/CD8^-$ cells is increased relative to wild type, and the proportion of $CD4^-/CD8^+$ cells is unchanged relative to wild type).

The central and multifaceted role of Ikaros in development, and the variety of phenotypes exhibited by Ikaros transgenic animals and cells, render Ikaros transgenic animals and cells useful, e.g., in a variety of assays, screens, and other methods. E.g., animals, cells and methods of the invention can be used to elucidate and characterize the function of the immune system, mechanisms of development, ways in which components of the immune system interact, ways in which the cell cycle is regulated, mechanisms of immune tolerance, and mechanisms of the development of immune or nervous tissue disorders. The cells, animals, and methods of the invention are also useful, e.g., for evaluating or discovering treatments which can be used to treat immune or nervous tissue disorders, for discovering or for evaluating treatments or methods of inducing immunological tolerance, e.g., to transplanted tissues. By way of example, Ikaros mice which develop lymphomas are useful not only for investigating the molecular basis of these disorders but for screening treatments for the ability to treat such disorders. Ikaros mice which lack one or more components of the immune system are useful in a variety of reconstitution experiments.

Accordingly, the invention features, a transgenic animal, e.g., a mammal, e.g., preferably a mouse, having an Ikaros transgene, or a nonhuman primate.

In preferred embodiments the animal is a transgenic mouse having a mutated Ikaros transgene, the mutation occurring in, or altering, e.g., a domain of the Ikaros gene described herein.

In other preferred embodiments the transgenic animal or cell: is heterozygous for an Ikaros transgene; homozygous for an Ikaros transgene; includes a first Ikaros transgene and a second Ikaros transgene; includes an Ikaros transgene and a second transgene which is other than an Ikaros transgene.

In another aspect, the invention features a method for evaluating the effect of a treatment on a transgenic cell or animal having an Ikaros transgene, e.g., the effect of the treatment on the development of the immune system. The method includes administering the treatment to a cell or animal having an Ikaros transgene, and evaluating the effect of the treatment on the cell or animal. The effect can be, e.g., the effect of the treatment on: the immune system or a component thereof, the nervous system or a component thereof, or the cell cycle. Immune system effects include e.g., T cell activation, T cell development, the ability to mount an immune response, the ability to give rise to a component of the immune system, B cell development, NK cell development, or the ratios $CD4^+/CD8^+$, $CD4^+/CD8^-$ and $CD4^-/CD8^+$.

In preferred embodiments the treatment can include: the administration of a drug, chemical, or other substance; the administration of ionizing radiation; the administration of an antibody, e.g., an antibody directed against a molecule or cell of the immune system; administration of a substance or other treatment which suppresses the immune system; or administration of a substance or other treatment which activates or boosts the function of the immune system; introduction of a nucleic acid, e.g., a nucleic acid which encodes or expresses a gene product, e.g., a component of the immune system; the introduction of a protein, e.g., a protein which is a component of the immune system.

In another aspect, the invention features a method for evaluating the effect of a treatment on an immune system component. The method includes: (1) supplying a transgenic cell or animal having an Ikaros transgene; (2) supplying the immune system component; (3) administering the treatment; and (4) evaluating the effect of the treatment on the immune system component.

In yet another aspect, the invention features a method for evaluating the interaction of a first immune system component with a second immune system component. The method includes: (1) supplying a transgenic cell or animal, e.g., a mammal, having an Ikaros transgene; (2) introducing the first and second immune system component into the transgenic cell or mammal; and (3) evaluating an interaction between the first and second immune system components.

Mice with mutant Ikaros transgenes which eliminate many of the normal components of the immune system, e.g., mice homozygous for a transgene having a deletion for some or all of exon 7, are particularly useful for "reconstitution experiments."

Ikaros transgenic mice which exhibit a phenotype characteristic of an immune system disorder, e.g., mice which are homozygous for a transgene having a deletion of all or some of exons 3 and 4, can serve as model systems for human disorders, e.g., for lymphoma.

In another aspect, the invention features a method for evaluating the effect of a treatment on an immune system disorder, e.g., a neoplastic disorder, a lymphoma, a T cell related lymphoma, including: administering the treatment to a cell or animal having an Ikaros transgene, and evaluating the effect of the treatment on the cell or animal.

In another aspect, the invention features, a method for evaluating the effect of a treatment on the nervous system comprising administering the treatment to a transgenic cell or an animal having an Ikaros transgene, and evaluating the effect of the treatment on the cell or the animal.

In another aspect, the invention features, a method for evaluating the effect of a treatment on a disorder of the nervous system, e.g., neurodegenerative disorder, e.g., Alzheimer's disease, Huntington's disease, Parkinson's disease, e.g, a neuroactive substance, e.g., neurotransmitter, imbalance, including administering the treatment to a cell or animal having an Ikaros transgene, and evaluating the effect of the treatment on the cell or animal.

The Ikaros gene is active in the early differentiation of lymphocytes, e.g. T cells and B cells. The gene encodes a family of unique zinc finger proteins, the Ikaros proteins. The proteins of the Ikaros family are isoforms which arise from differential splicing of Ikaros gene transcripts. The isoforms of the Ikaros family generally include a common 3' exon (Ikaros exon E7, which includes amino acid residues 283–518 of the mouse Ikaros protein represented by SEQ ID NO:4, and amino acid residues 229–461 of the human Ikaros protein represented by SEQ ID NO:2) but differ in the 5' region. The Ikaros family includes all naturally occurring splicing variants which arise from transcription and processing of the Ikaros gene. Five such isoforms are described in copending U.S. patent application Ser. No. 08/121,438, filed Sep. 14, 1993. The Ikaros family also includes other isoforms, including those generated by mutagenesis and/or by in vitro exon shuffling. The naturally occurring Ikaros proteins can bind and activate (to differing extents) the enhancer of the CD3δ gene, and are expressed primarily if not solely in T cells in the adult. The expression pattern of this transcription factor during embryonic development show that Ikaros proteins play a role as a genetic switch regulating entry into the T cell lineage. The Ikaros gene is also expressed in the proximal corpus striatum during early embryogenesis in mice.

As described above, the Ikaros gene is a master regulator for lymphocyte specification. The Ikaros gene was initially described for its ability to mediate the activity of an enhancer element in the CD3 3δ gene, an early and definitive marker of the T cell differentiation (Georgopoulos, K. et al. (1992) *Science* 258:808). During embryogenesis, Ikaros expression is restricted to sites of hemopoiesis where it precedes and overlaps with areas of lymphocyte differentiation. Ikaros is expressed in early B cells and in T cells and their progenitors in the adult organism. Consistent with its role as a master regulator of lymphocyte specific gene expression, the Ikaros gene encodes a family of zinc finger DNA binding proteins by means of differential splicing (Molnar et al., 1994). These protein isoforms display overlapping but distinct DNA binding specificities and range from strong activators to suppressors of transcription. Together, Ikaros proteins appear to control multiple layers of gene expression during lymphocyte ontogeny in the embryo and in the adult. Significantly, high affinity binding sites for the Ikaros proteins were identified in the regulatory domains of many lymphocyte specific genes among which are the members of the CD3/TCR complex, terminal deoxyribonucleotidyl transferase (TdT), the IL-2 receptor, immunoglobulin heavy and light chains and the signal transducing molecule Igα. These genes are all important components in T and B cell differentiation pathways and their expression is a prerequisite for lymphocyte development. In addition, the Ikaros proteins can bind and activate a subset of NF-KB sites implicated in stimulating gene expression in the activated T cell (Beg, A. A. and Baldwin, A. S. J. (1993) *Genes Dev.* 7:2064–2070; Lenardo, M. J. and Baltimore, D. (1989) *Cell* 58:227–229). The Ikaros gene and its splicing products are highly conserved between mice and mane in further support of a master switch function for the lymphopoietic system across species (Molnar, et al., 1994).

The role of Ikaros as a major determinant in lymphocyte specification, development and homeostasis is shown in Ikaros transgenic animals. A deletion was introduced in the DNA binding domain of the Ikaros gene by homologous recombination in embryonic stem (ES) cells. This mutation, which was expected to abrogate the ability of four of the Ikaros proteins to bind DNA, was introduced in the mouse germ line. Mice homozygous for this Ikaros mutation lack both mature T and B lymphocytes and their well defined progenitors (Ardavin et al., 1993; Godfrey and Zlotnik, 1993; Ikuta, et al., 1992; Karasuyama et al.,; Spanopoulou et al., 1994). Natural killer (NK) cells, believed to arise from a common precursor with T cells are also absent in Ikaros mutant mice (Hackett et al., 1 986a; Hackett et al., 1986b; Rodewald et al., 1992). The erythroid and myeloid compartments of the hemopoietic system in the Ikaros −/− mutant mice were intact. Together these two lineages comprised almost 100% of the spleen and the bone marrow cell populations. Significantly, the absolute numbers of erythroid and myeloid progenitors were higher in the spleen than in the bone marrow. Infections throughout the major organs particularly the gut, the liver and the blood were detected as early as one week past birth and were often the cause of death of these mice.

Together, these results demonstrate that lack of functionally intact Ikaros proteins prevents the production of T, B and NK lymphocytes. Ikaros mutant mice therefore lack specific immune responses mediated by T and B cells and the first line of defense mediated by NK cells. These severely immunocompromised animals rapidly succumb to opportunistic infections.

Other features and advantages of the invention will be apparent from the following description and from the claims.

BRIEF DESCRIPTION OF THE DRAWINGS

The drawings are first briefly described.

Drawings

FIG. 1 is a map of the DNA sequence of a murine Ikaros cDNA and the desired amino acid sequence encoded thereby (SEQ ID NO:1).

FIG. 2 is a partial sequence of a human Ikaros cDNA (SEQ ID NO:2).

DETAILED DESCRIPTION OF THE INVENTION

Ikaros Transgenic Animals and Uses Thereof

Figure 3:
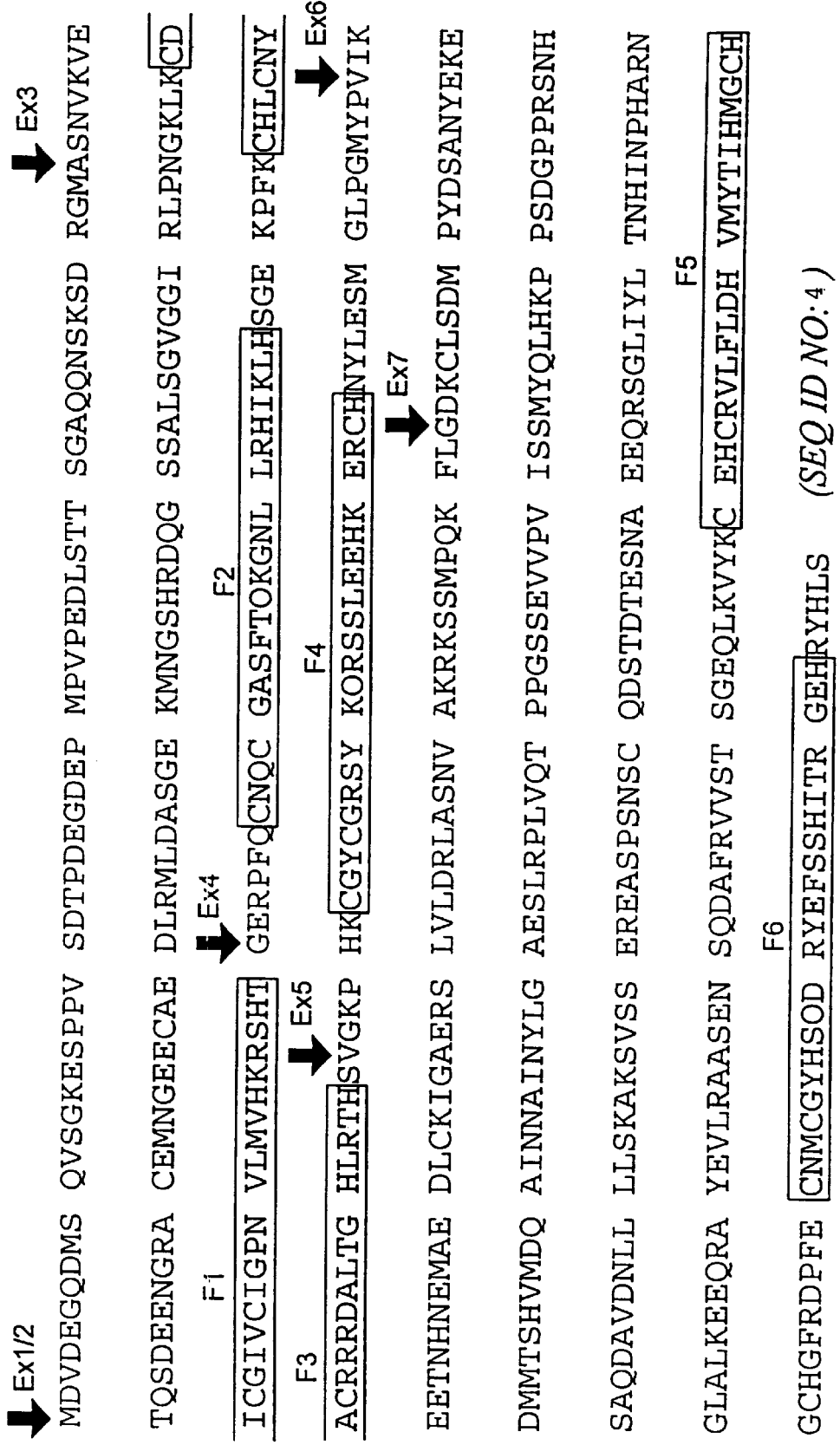
FIG. 3 is a depiction of the partial amino acid composition of the IK-1 cDNA, including Ex3, Ex4, Ex5, Ex6, and Ex7 (SEQ ID NO:4).

In general, the invention features, a transgenic animal, e.g., a mammal, having an Ikaros transgene.

In preferred embodiments the mammal is a non-human mammal, e.g., a swine, a monkey, a goat, or a rodent, e.g., a rat, but preferably a mouse.

In other preferred embodiments: the Ikaros transgene includes a mutation. In yet more preferred embodiments the Ikaros transgene includes a mutation and: the mutation is, or results from, a chromosomal alteration; the mutation is, or results from, any of an alteration resulting from homologous recombination, site-specific recombination, nonhomologous recombination; the mutation is, or results from, any of an inversion, deletion, insertion, translocation, or reciprocal translocation; the mutation is, or results from, any of a deletion of one or more nucleotides from the gene, an addition of one or more nucleotides to the gene, a change of identity of one or more nucleotides of the gene.

In yet other preferred embodiments the Ikaros transgene includes a mutation and: the mutation results in mis-expression of the transgene or of another gene in the animal; the mutation results in mis-expression of the transgene and the mis-expression is any of an alteration in the level of a messenger RNA transcript of the transgene, the presence of a non-wild type splicing pattern of a messenger RNA transcript of the transgene, or a non-wild type level of a protein encoded by the transgene; the mutation alters the relative abundance of a first Ikaros isoform with respect to a second Ikaros isoform, as compared, e.g., to a wild type animal or to an animal lacking the transgene; the mutation is in, or alters, the sequence, expression, or splicing of one or more of the following exons: exon 1/2, exon 3, exon 4, exon 5, exon 6, and exon 7; the mutation is in, or alters, the sequence, expression, or splicing of a DNA binding domain of, the Ikaros gene or DNA; the mutation is a deletion of portions of exon 3 and/or exon 4; the mutation is alters the expression, activation, or dimerization of an Ikaros gene product; the mutation is a deletion of a portion of exon 7.

In yet other preferred embodiments the Ikaros transgene includes an Ikaros transcriptional control region operably linked to a sequence which is functionally unrelated to the Ikaros gene, or which is less than 50% homologous with the Ikaros gene, e.g., a nucleic acid encoding a reporter molecule, a nucleic acid encoding a toxin, or a nucleic acid encoding a gene to be placed under the control of an Ikaros regulatory region.

In yet other preferred embodiments the Ikaros transgene encodes: an Ikaros protein which is a competitive inhibitor or an antagonist of a naturally occurring Ikaros protein; an Ikaros gene genetically engineered, e.g., by deletion of an exon, or by using a sequence which results in expression in a preselected tissue, to encode a specific isoform, or a specific subset of Ikaros isoforms, e.g., the transgene is genetically engineered to express one of mIK-1, mIK-2, mIK-3, mIK-4, mIK-5, hIK-1, hIK-2, hIK-3, hIK-4, or hIK-5.

In preferred embodiments the transgenic animal: is heterozygous for an Ikaros transgene; homozygous for an Ikaros transgene; includes a first Ikaros transgene and a second Ikaros transgene; includes an Ikaros transgene and a second transgene which is other than an Ikaros transgene.

In another aspect, the invention includes a transgenic mouse having a mutated Ikaros transgene, the mutation occurring in, or altering, a domain of the Ikaros gene, e.g., a domain described herein, e.g., the mutation is in, or alters, the sequence of a DNA binding domain of the Ikaros transgene.

In preferred embodiments: the mutation is a deletion of one or more nucleotides from the Ikaros transgene; the mutation is a deletion which is in or which includes a portion of exon 3 and/or exon 4 of the Ikaros transgene.

In another aspect, the invention includes a transgenic mouse having a mutated Ikaros transgene in which the mutation alters the expression, activation, or dimerization of an Ikaros gene product.

In preferred embodiments: the mutation is a deletion of one or more nucleotides from the Ikaros transgene; the mutation is a deletion which is in or which includes a portion of exon 7 of the Ikaros transgene.

In another aspect, the invention features a method for evaluating the effect of a treatment on a transgenic cell or animal having an Ikaros transgene. The method includes administering the treatment to a cell or animal having an Ikaros transgene, and evaluating the effect of the treatment on the cell or animal. The effect can be, e.g., the effect of the treatment on the immune system or a component thereof, the nervous system or a component thereof, or the cell cycle. Immune system effects include e.g., T cell activation, T cell development, B cell development, NK cell development, and the ratios $CD4^+/CD8^+$, $CD4^+/CD8^-$ and $CD4^-/CD8^+$.

In preferred embodiments using a transgenic animal the transgenic animal is a mammal, e.g., a non-human mammal, e.g., a nonhuman primate or a swine, a monkey, a goat, or a rodent, e.g., a rat, but preferably a mouse.

In preferred embodiments using a transgenic cell the transgenic cell is a mammalian cell, e.g., a non-human mammalian cell, e.g., a swine, a monkey, a goat, or a rodent, preferably a mouse, cell.

In other preferred embodiments: the Ikaros transgene includes a mutation. In yet more preferred embodiments the Ikaros transgene includes a mutation and: the mutation is, or results from, a chromosomal alteration; the mutation is, or results from, any of an alteration resulting from homologous recombination, site-specific recombination, nonhomologous recombination; the mutation is, or results from, any of an inversion, deletion, insertion, translocation, or reciprocal translocation; the mutation is, or results from, any of a deletion of one or more nucleotides from the gene, an addition of one or more nucleotides to the gene, a change of identity of one or more nucleotides of the gene.

In yet other preferred embodiments the Ikaros transgene includes a mutation and: the mutation results in mis-expression of the transgene or of another gene in the animal or cell; the mutation results in mis-expression of the transgene and the mis-expression is any of an alteration in the level of a messenger RNA transcript of the transgene, the presence of a non-wild type splicing pattern of a messenger RNA transcript of the transgene, or a non-wild type level of a protein encoded by the transgene; the mutation alters the relative abundance of a first Ikaros isoform with respect to a second Ikaros isoform, as compared, e.g., to a wild type animal or to an animal lacking the transgene; the mutation is in, or alters, the sequence, expression, or splicing of one or more of the following exons: exon 1/2, exon 3, exon 4, exon 5, exon 6, and exon 7; the mutation is in, or alters, the sequence, expression, or splicing of a DNA binding domain of, the Ikaros gene or DNA; the mutation is a deletion of portions of exon 3 and/or exon 4; the mutation is alters the expression, activation, or dimerization of an Ikaros gene product; the mutation is a deletion of a portion of exon 7.

In yet other preferred embodiments the Ikaros transgene includes an Ikaros transcriptional control region operably linked to a sequence which is functionally unrelated to the Ikaros gene, or which is less than 50% homologous with the Ikaros gene, e.g., a nucleic acid encoding a reporter molecule, a nucleic acid encoding a toxin, or a nucleic acid encoding a gene to be placed under the control of an Ikaros regulatory region.

In yet other preferred embodiments the Ikaros transgene encodes: an Ikaros protein which is a competitive inhibitor or an antagonist of a naturally occurring Ikaros protein; an Ikaros gene genetically engineered, e.g., by deletion of an exon, or by using a sequence which results in expression in a preselected tissue, to encode a specific isoform, or a specific subset of Ikaros isoforms, e.g., the transgene is genetically engineered to express one of mIK-1, mIK-2, mIK-3, mIK-4, mIK-5, hIK-1, hIK-2, hIK-3, hIK-4, or hIK-5.

In preferred embodiments the transgenic animal or cell: is heterozygous for an Ikaros transgene; homozygous for an Ikaros transgene; includes a first Ikaros transgene and a second Ikaros transgene; includes an Ikaros transgene and a second transgene which is other than an Ikaros transgene.

In preferred embodiments, the evaluating step includes determining the effect of the treatment on a parameter related to the immune system. The parameter related to the immune system can, e.g., be any of: the presence, function, or morphology of T cells or their progenitors: the presence, function, or morphology of B cells or their progenitors; the presence, function, or morphology of natural killer cells or their progenitors; resistance to infection; life span; body weight; the presence, function, or morphology of tissues or organs of the immune system; the expression of the Ikaros transgene; the ability of a component of the immune system to respond to a stimulus (e.g., a diffusable substance, e.g., cytokines, other cells of the immune system, or antigens); the ability to exhibit immunological tolerance to an alloantigen or a xenoantigen.

In preferred embodiments the evaluating step includes evaluating the expression of a gene or transgene, e.g., a gene which encodes a component of the immune system, e.g., a cell surface marker, a receptor, or a cytokine; a gene which regulates the expression of a component of the immune system, a gene which modulates the ability of the immune system to function, the Ikaros gene, or an Ikaros transgene.

In preferred embodiments the evaluating step includes evaluating the growth rate of a transgenic cell.

In preferred embodiments the treatment can include: the administration of a drug, chemical, or other substance; the administration of ionizing radiation; the administration of an antibody, e.g., an antibody directed against a molecule or cell of the immune system, e.g., an antibody directed against a T cell, B cell, NK cell, dendritic cell, or thymic cell, an antibody directed against a precursor of a T cell, B cell, NK cell, dendritic cell, or thymic cell, an antibody directed against a cell surface marker of a T cell, B cell, NK cell, dendritic cell, or thymic cell; introduction of a component of the immune system derived from an animal of the same species as the transgenic animal; the introduction of a component of the immune system derived from an animal of a different species from the transgenic animal; the introduction of an immune system component derived from an animal or cell other than the transgenic animal or cell; the introduction of an immune system component which is endogenous, (i.e., it is present in the transgenic animal or cell and does not have to be introduced into the transgenic animal or cell) to the transgenic animal or cell; the introduction of an immune system component derived from an animal or cell of the same species as the transgenic animal or cell; the introduction of an immune system component derived from an animal or cell (of the same species as the transgenic animal) which does not include the transgene; the introduction of an immune system component derived from an immunologically competent animal, or from a cell derived from an immunologically competent animal, of the same species as the transgenic animal or cell; the introduction of an immune system component derived from an animal or cell of a different species from the transgenic animal or cell; the introduction of an immune system component derived from an immunologically competent animal, or from a cell derived from an immunologically competent animal, of a different species than the transgenic animal or cell; administration of a substance or other treatment which suppresses the immune system; administration of a substance or other treatment which activates or boosts the function of the immune system; introduction of a nucleic acid, e.g., a nucleic acid which encodes or expresses a component of the immune system; or the introduction of a protein, e.g., a protein which is a component of the immune system.

In another aspect, the invention features a method for evaluating the effect of a treatment on an immune system component. The method includes: (1) supplying a transgenic cell or animal having an Ikaros transgene; (2) supplying the immune system component; (3) administering the treatment; and (4) evaluating the effect of the treatment on the immune system component.

In preferred embodiments using a transgenic animal the transgenic animal is a mammal, e.g., a non-human mammal, e.g., a nonhuman primate or a swine, a monkey, a goat, or a rodent, e.g., a rat, but preferably a mouse.

In preferred embodiments using a transgenic cell the transgenic cell is a mammalian cell, e.g., a non-human mammalian cell, e.g., a swine, a monkey, a goat, or a rodent, preferably a mouse, cell.

In other preferred embodiments: the Ikaros transgene includes a mutation. In yet more preferred embodiments the Ikaros transgene includes a mutation and: the mutation is, or results from, a chromosomal alteration; the mutation is, or results from, any of an alteration resulting from homologous recombination, site-specific recombination, nonhomologous recombination; the mutation is, or results from, any of an inversion, deletion, insertion, translocation, or reciprocal translocation; the mutation is, or results from, any of a deletion of one or more nucleotides from the gene, an addition of one or more nucleotides to the gene, a change of identity of one or more nucleotides of the gene.

In yet other preferred embodiments the Ikaros transgene includes a mutation and: the mutation results in mis-expression of the transgene or of another gene in the animal; the mutation results in mis-expression of the transgene and the mis-expression is any of an alteration in the level of a messenger RNA transcript of the transgene, the presence of a non-wild type splicing pattern of a messenger RNA transcript of the transgene, or a non-wild type level of a protein encoded by the transgene; the mutation alters the relative abundance of a first Ikaros isoform with respect to a second Ikaros isoform, as compared, e.g., to a wild type animal or to an animal lacking the transgene; the mutation is in, or alters, the sequence, expression, or splicing of one or more of the following exons: exon 1/2, exon 3, exon 4, exon 5, exon 6, and exon 7; the mutation is in, or alters, the sequence, expression, or splicing of a DNA binding domain of, the Ikaros gene or DNA; the mutation is a deletion of portions of exon 3 and/or exon 4; the mutation is alters the expression, activation, or dimerization of an Ikaros gene product; the mutation is a deletion of a portion of exon 7.

In yet other preferred embodiments the Ikaros transgene includes an Ikaros transcriptional control region operably linked to a sequence which is functionally unrelated to the Ikaros gene, or which is less than 50% homologous with the Ikaros gene, e.g., a nucleic acid encoding a reporter molecule, a nucleic acid encoding a toxin, or a nucleic acid encoding a gene to be placed under the control of an Ikaros regulatory region.

In yet other preferred embodiments the Ikaros transgene encodes: an Ikaros protein which is a competitive inhibitor or an antagonist of a naturally occurring Ikaros protein; an Ikaros gene genetically engineered, e.g., by deletion of an exon, or by using a sequence which results in expression in a preselected tissue, to encode a specific isoform, or a specific subset of Ikaros isoforms, e.g., the transgene is genetically engineered to express one of mIK-1, mIK-2, mIK-3, mIK-4, mIK-5, hIK-1, hIK-2, hIK-3, hIK-4, or hIK-5.

In preferred embodiments the transgenic animal or cell: is heterozygous for an Ikaros transgene; homozygous for an Ikaros transgene; includes a first Ikaros transgene and a second Ikaros transgene; includes an Ikaros transgene and a second transgene which is other than an Ikaros transgene.

In preferred embodiments: the immune system component is taken from an animal or cell other than the transgenic animal or cell and is introduced into the transgenic cell or animal; the component is endogenous, to the transgenic animal or cell; the immune system component is taken from an animal or cell of the same species as the transgenic animal or cell and is introduced into the transgenic cell or animal (i.e., it is present in the transgenic animal or cell and does not have to be introduced into the transgenic animal or cell); the immune system component is taken from an animal or cell (of the same species as the transgenic animal) which does not include the transgene and is introduced into the transgenic cell or animal; the immune system component is taken from an immunologically competent animal, or from a cell derived from an immunologically competent animal, of the same species as the transgenic animal or cell and is introduced into the transgenic cell or animal; the immune system component is taken from an animal or cell of a different species from the transgenic animal or cell and is introduced into the transgenic cell or animal; the immune system component is taken from an immunologically competent animal, or from a cell derived from an immunologically competent animal, of a different species than the transgenic animal or cell and is introduced into the transgenic cell or animal.

In preferred embodiments the immune system component is any of an antigen, a T cell, a T cell progenitor, a totipotent hematopoietic stem cell, a pluripotent hematopoietic stem cell, a B cell, a B cell progenitor, a natural killer cell, a natural killer cell progenitor, bone marrow tissue, spleen tissue, or thymic tissue.

In other preferred embodiments the immune system component is: a nucleic acid which encodes an immune system component, e.g., a cell surface marker, a receptor, or a cytokine; a protein, e.g., a cell surface marker, a receptor, or a cytokine.

In preferred embodiments, the evaluating step includes determining the effect of the treatment on a parameter related to the immune system. The parameter related to the immune system can, e.g., be any of: the presence, function, or morphology of T cells or their progenitors: the presence, function, or morphology of B cells or their progenitors; the presence, function, or morphology of natural killer cells or their progenitors; resistance to infection; life span; body weight; the presence, function, or morphology of tissues or organs of the immune system; the expression of the Ikaros transgene; the ability of a component of the immune system to respond to a stimulus (e.g., a diffusable substance, e.g., cytokines, other cells of the immune system, or antigens); the ability to exhibit immunological tolerance to an alloantigen or a xenoantigen.

In preferred embodiments the evaluating step includes evaluating the expression of a gene or transgene, e.g., a gene which encodes a component of the immune system, e.g., a cell surface marker, a receptor, or a cytokine; a gene which regulates the expression of a component of the immune system, a gene which modulates the ability of the immune system to function, the Ikaros gene. or an Ikaros transgene.

In preferred embodiments the evaluating step includes evaluating the growth rate of a transgenic cell.

In preferred embodiments the treatment can include: the administration of a drug, chemical, or other substance; the administration of ionizing radiation; the administration of an antibody, e.g., an antibody directed against a molecule or cell of the immune system, e.g., an antibody directed against a T cell, B cell, NK cell, dendritic cell, or thymic cell, an antibody directed against a precursor of a T cell, B cell, NK cell, dendritic cell, or thymic cell, an antibody directed against a cell surface marker of a T cell, B cell, NK cell, dendritic cell, or thymic cell; introduction of a component of the immune system derived from an animal or cell of the same species as the transgenic animal or cell; the introduction of a component of the immune system derived from an animal or cell of a different species from the transgenic animal or cell; the introduction of an immune system component derived from an animal or cell other than the transgenic animal or cell; the introduction of an immune system component which is endogenous, (i.e., it is present in the transgenic animal or cell and does not have to be introduced into the transgenic animal or cell) to the transgenic animal or cell; the introduction of an immune system component derived from an animal or cell of the same species as the transgenic animal or cell ; the introduction of an immune system component derived from an animal or cell (of the same species as the transgenic animal) which does not include the transgene; the introduction of an immune system component derived from an immunologically competent animal, or from a cell derived from an immunologically competent animal, of the same species as the transgenic animal or cell; the introduction of an immune system component derived from an animal or cell of a different species from the transgenic animal or cell; the introduction of an immune system component derived from an immunologically competent animal, or from a cell derived from an immunologically competent animal, of a different species than the transgenic animal or cell; administration of a substance or other treatment which suppresses the immune system; or administration of a substance or other treatment which activates or boosts the function of the immune system; introduction of a nucleic acid, e.g., a nucleic acid which encodes or expresses a component of the immune system; the introduction of a protein, e.g., a protein which is a component of the immune system.

In yet another aspect, the invention features a method for evaluating the interaction of a first immune system component with a second immune system component. The method includes: (1) supplying a transgenic cell or animal, e.g., a mammal, having an Ikaros transgene; (2) introducing the first and second immune system component into the transgenic cell or mammal; and (3) evaluating an interaction between the first and second immune system components.

In preferred embodiments, with respect to either the first and/or the second immune system component: the immune system component is taken from an animal or cell other than the transgenic cell or animal and is introduced into the transgenic cell or animal; the component is endogenous, (i.e., it is present in the transgenic animal or cell and does not have to be introduced into the transgenic animal or cell) to the transgenic animal or cell; the immune system component is taken from an animal or cell of the same species as the transgenic animal or cell and is introduced into the transgenic cell or animal; the immune system component is taken from an animal or cell (of the same species as the transgenic animal) which does not include the transgene and is introduced into the transgenic cell or animal; the immune system component is taken from an immunologically competent animal, or from a cell derived from an immunologically competent animal, of the same species as the transgenic animal or cell and is introduced into the transgenic cell or animal; the immune system component is taken from an animal or cell of a different species from the transgenic animal or cell and is introduced into the transgenic cell or animal; the immune system component is taken from an immunologically competent animal, or from a cell derived from an immunologically competent animal, of a different species than the transgenic animal or cell and is introduced into the transgenic cell or animal.

In preferred embodiments the immune system component is any of an antigen, a T cell, a T cell progenitor, a totipotent hematopoietic stem cell, a pluripotent hematopoietic stem cell, a B cell, a B cell progenitor, a natural killer cell, a natural killer cell progenitor, bone marrow tissue, spleen tissue, thymic tissue, or other lymphoid tissue and its stroma, e.g., encapsulated lymphoid tissue, e.g., lymph nodes, or unencapsulated lymphoid tissue, e.g., Peyer's patches in the ileum, lymphoid nodules found in the mucosa of the alimentary, respiratory, urinary, and reproductive tracts.

In other preferred embodiments the immune system component is: a nucleic acid which encodes an immune system component, e.g., a cell surface marker, a receptor, or a cytokine; a protein, e.g., a cell surface marker, a receptor, or a cytokine.

In preferred embodiments, the first component is the same as the second component; the first component is different from the second component; the first and the second components are from the same species as the transgenic mammal; the first and the second components are from species different from the species of the transgenic mammal; the first and second components are from different species.

In preferred embodiments using a transgenic animal the transgenic animal is a mammal, e.g., a non-human mammal, e.g., a nonhuman primate or a swine, a monkey, a goat, or a rodent, e.g., a rat, but preferably a mouse.

In preferred embodiments using a transgenic cell the transgenic cell is a mammalian cell, e.g., a non-human mammalian cell, e.g., a swine, a monkey, a goat, or a rodent, preferably a mouse, cell.

In other preferred embodiments: the Ikaros transgene includes a mutation. In yet more preferred embodiments the Ikaros transgene includes a mutation and: the mutation is, or results from, a chromosomal alteration; the mutation is, or results from, any of an alteration resulting from homologous recombination, site-specific recombination, nonhomologous recombination; the mutation is, or results from, any of an inversion, deletion, insertion, translocation, or reciprocal translocation; the mutation is, or results from, any of a deletion of one or more nucleotides from the gene, an addition of one or more nucleotides to the gene, a change of identity of one or more nucleotides of the gene.

In yet other preferred embodiments the Ikaros transgene includes a mutation and: the mutation results in mis-expression of the transgene or of another gene in the animal; the mutation results in mis-expression of the transgene and the mis-expression is any of an alteration in the level of a messenger RNA transcript of the transgene, the presence of a non-wild type splicing pattern of a messenger RNA transcript of the transgene, or a non-wild type level of a protein encoded by the transgene; the mutation alters the relative abundance of a first Ikaros isoform with respect to a second Ikaros isoform, as compared, e.g., to a wild type animal or to an animal lacking the transgene; the mutation is in, or alters, the sequence, expression, or splicing of one or more of the following exons: exon 1/2, exon 3, exon 4, exon 5, exon 6, and exon 7; the mutation is in, or alters, the sequence, expression, or splicing of a DNA binding domain of, the Ikaros gene or DNA; the mutation is a deletion of portions of exon 3 and/or exon 4; the mutation is alters the expression, activation, or dimerization of an Ikaros gene product; the mutation is a deletion of a portion of exon 7.

In yet other preferred embodiments the Ikaros transgene includes an Ikaros transcriptional control region operably linked to a sequence which is functionally unrelated to the Ikaros gene, or which is less than 50% homologous with the Ikaros gene, e.g., a nucleic acid encoding a reporter molecule, a nucleic acid encoding a toxin, or a nucleic acid encoding a gene to be placed under the control of an Ikaros regulatory region.

In yet other preferred embodiments the Ikaros transgene encodes: an Ikaros protein which is a competitive inhibitor or an antagonist of a naturally occurring Ikaros protein; an Ikaros gene genetically engineered, e.g., by deletion of an exon, or by using a sequence which results in expression in a preselected tissue, to encode a specific isoform, or a specific subset of Ikaros isoforms, e.g., the transgene is genetically engineered to express one of mIK-1, mIK-2, mIK-3, mIK-4, mIK-5, hIK-1, hIK-2, hIK-3, hIK-4, or hIK-5.

In preferred embodiments the transgenic animal or cell: is heterozygous for an Ikaros transgene; homozygous for an Ikaros transgene; includes a first Ikaros transgene and a second Ikaros transgene; includes an Ikaros transgene and a second transgene which is other than an Ikaros transgene.

In preferred embodiments, the evaluating step includes determining the effect of the treatment on a parameter related to the immune system. The parameter related to the immune system can, e.g., be any of: the presence, function, or morphology of T cells or their progenitors: the presence, function, or morphology of B cells or their progenitors; the presence, function, or morphology of natural killer cells or their progenitors; resistance to infection; life span; body weight; the presence, function, or morphology of tissues or organs of the immune system; the expression of the Ikaros transgene; the ability of a component of the immune system to respond to a stimulus (e.g., a diffusable substance, e.g., cytokines, other cells of the immune system, or antigens); the ability to exhibit immunological tolerance to an alloantigen or a xenoantigen.

In preferred embodiments the evaluating step includes evaluating the expression of a gene or transgene, e.g., a gene which encodes a component of the immune system, e.g., a cell surface marker, a receptor, or a cytokine; a gene which regulates the expression of a component of the immune system, a gene which modulates the ability of the immune system to function, the Ikaros gene. or an Ikaros transgene.

In preferred embodiments the evaluating step includes evaluating the growth rate of a transgenic cell.

In another aspect, the invention features a method for evaluating the effect of a treatment on an immune system disorder including: administering the treatment to a cell or animal having an Ikaros transgene, and evaluating the effect of the treatment on the cell or animal.

In preferred embodiments the disorder is: a neoplastic disorder; a lymphoma; a T cell related lymphoma.

In preferred embodiments using a transgenic animal the transgenic animal is a mammal, e.g., a non-human mammal, e.g., a swine, a monkey, a goat, or a rodent, e.g., a rat, but preferably a mouse.

In preferred embodiments using a transgenic cell the transgenic cell is a mammalian cell, e.g., a non-human mammalian cell, e.g., a swine, a monkey, a goat, or a rodent, preferably a mouse, cell.

In other preferred embodiments: the Ikaros transgene includes a mutation. In yet more preferred embodiments the Ikaros transgene includes a mutation and: the mutation is, or results from, a chromosomal alteration; the mutation is, or results from, any of an alteration resulting from homologous recombination, site-specific recombination, nonhomologous recombination; the mutation is, or results from, any of an inversion, deletion, insertion, translocation, or reciprocal translocation; the mutation is, or results from, any of a deletion of one or more nucleotides from the gene, an addition of one or more nucleotides to the gene, a change of identity of one or more nucleotides of the gene.

In yet other preferred embodiments the Ikaros transgene includes a mutation and: the mutation results in mis-expression of the transgene or of another gene in the animal; the mutation results in mis-expression of the transgene and the mis-expression is any of an alteration in the level of a messenger RNA transcript of the transgene, the presence of a non-wild type splicing pattern of a messenger RNA transcript of the transgene, or a non-wild type level of a protein encoded by the transgene; the mutation alters the relative abundance of a first Ikaros isoform with respect to a second Ikaros isoform, as compared, e.g., to a wild type animal or to an animal lacking the transgene; the mutation is in, or alters, the sequence, expression, or splicing of one or more of the following exons: exon 1/2, exon 3, exon 4, exon 5, exon 6, and exon 7; the mutation is in, or alters, the sequence, expression, or splicing of a DNA binding domain of, the Ikaros gene or DNA; the mutation is a deletion of portions of exon 3 and/or exon 4; the mutation is alters the expression, activation, or dimerization of an Ikaros gene product; the mutation is a deletion of a portion of exon 7.

In yet other preferred embodiments the Ikaros transgene includes an Ikaros transcriptional control region operably linked to a sequence which is functionally unrelated to the Ikaros gene, or which is less than 50% homologous with the Ikaros gene, e.g., a nucleic acid encoding a reporter molecule, a nucleic acid encoding a toxin, or a nucleic acid encoding a gene to be placed under the control of an Ikaros regulatory region.

In yet other preferred embodiments the Ikaros transgene encodes: an Ikaros protein which is a competitive inhibitor or an antagonist of a naturally occurring Ikaros protein; an Ikaros gene genetically engineered, e.g., by deletion of an exon, or by using a sequence which results in expression in a preselected tissue, to encode a specific isoform, or a specific subset of Ikaros isoforms, e.g., the transgene is genetically engineered to express one of mIK-1, mIK-2, mIK-3, mIK-4, mIK-5, hIK-1, hIK-2, hIK-3, hIK-4, or hIK-5.

In preferred embodiments the transgenic animal or cell: is heterozygous for an Ikaros transgene; homozygous for an Ikaros transgene; includes a first Ikaros transgene and a second Ikaros transgene; includes an Ikaros transgene and a second transgene which is other than an Ikaros transgene.

In preferred embodiments, the evaluating step includes determining the effect of the treatment on a parameter related to the immune system. The parameter related to the immune system can, e.g., be any of: the presence, function, or morphology of T cells or their progenitors: the presence, function, or morphology of B cells or their progenitors; the presence, function, or morphology of natural killer cells or their progenitors; resistance to infection; life span; body weight; the presence, function, or morphology of tissues or organs of the immune system; the expression of the Ikaros transgene; the ability of a component of the immune system to respond to a stimulus (e.g., a diffusable substance, e.g., cytokines, other cells of the immune system, or antigens); the ability to exhibit immunological tolerance to an alloantigen or a xenoantigen.

In preferred embodiments the evaluating step includes evaluating the expression of a gene or transgene, e.g., a gene which encodes a component of the immune system, e.g., a cell surface marker, a receptor, or a cytokine; a gene which regulates the expression of a component of the immune system, a gene which modulates the ability of the immune system to function, the Ikaros gene. or an Ikaros transgene.

In preferred embodiments the evaluating step includes evaluating the growth rate of a transgenic cell.

In preferred embodiments the treatment can include: the administration of a drug, chemical, or other substance; the administration of ionizing radiation; the administration of an antibody, e.g., an antibody directed against a molecule or cell of the immune system, e.g., an antibody directed against a T cell, B cell, NK cell, dendritic cell, or thymic cell, an antibody directed against a precursor of a T cell, B cell, NK cell, dendritic cell, or thymic cell, an antibody directed against a cell surface marker of a T cell, B cell, NK cell, dendritic cell, or thymic cell; introduction of a component of the immune system derived from an animal of the same species as the transgenic animal; the introduction of a component of the immune system derived from an animal of a different species from the transgenic animal; the introduction of an immune system component derived from an animal or cell other than the transgenic animal or cell; the introduction of an immune system component which is endogenous, (i.e., it is present in the transgenic animal or cell and does not have to be introduced into the transgenic animal or cell) to the transgenic animal or cell; the introduction of an immune system component derived from an animal or cell of the same species as the transgenic animal or cell; the introduction of an immune system component derived from an animal or cell (of the same species as the transgenic animal) which does not include the transgene; the introduction of an immune system component derived from an immunologically competent animal, or from a cell derived from an immunologically competent animal, of the same species as the transgenic animal or cell; the introduction of an immune system component derived from an animal or cell of a different species from the transgenic animal or cell; the introduction of an immune system component derived from an immunologically competent animal, or from a cell derived from an immunologically competent animal, of a different species than the transgenic animal or cell; administration of a substance or other treatment which suppresses the immune system; or administration of a substance or other treatment which activates or boosts the function of the immune system; introduction of a nucleic acid, e.g., a nucleic acid which encodes or expresses a component of the immune system; the introduction of a protein, e.g., a protein which is a component of the immune system.

In another aspect, the invention features a method for evaluating the effect of a treatment on the nervous system including administering the treatment to a transgenic cell or an animal having an Ikaros transgene, and evaluating the effect of the treatment on the cell or the animal.

In preferred embodiments using a transgenic animal the transgenic animal is a mammal, e.g., a non-human mammal, e.g., a swine, a monkey, a goat, or a rodent, e.g., a rat, but preferably a mouse.

In preferred embodiments using a transgenic cell the transgenic cell is a mammalian cell, e.g., a non-human mammalian cell, e.g., a swine, a monkey, a goat, or a rodent, preferably a mouse, cell.

In other preferred embodiments: the Ikaros transgene includes a mutation. In yet more preferred embodiments the Ikaros transgene includes a mutation and: the mutation is, or results from, a chromosomal alteration; the mutation is, or results from, any of an alteration resulting from homologous recombination, site-specific recombination, nonhomologous recombination; the mutation is, or results from, any of an inversion, deletion, insertion, translocation, or reciprocal translocation; the mutation is, or results from, any of a deletion of one or more nucleotides from the gene, an addition of one or more nucleotides to the gene, a change of identity of one or more nucleotides of the gene.

In yet other preferred embodiments the Ikaros transgene includes a mutation and: the mutation results in mis-expression of the transgene or of another gene in the animal; the mutation results in mis-expression of the transgene and the mis-expression is any of an alteration in the level of a messenger RNA transcript of the transgene, the presence of a non-wild type splicing pattern of a messenger RNA transcript of the transgene, or a non-wild type level of a protein encoded by the transgene; the mutation alters the relative abundance of a first Ikaros isoform with respect to a second Ikaros isoform, as compared, e.g., to a wild type animal or to an animal lacking the transgene; the mutation is in, or alters, the sequence, expression, or splicing of one or more of the following exons: exon 1/2, exon 3, exon 4, exon 5, exon 6, and exon 7; the mutation is in, or alters, the sequence, expression, or splicing of a DNA binding domain of, the Ikaros gene or DNA; the mutation is a deletion of portions of exon 3 and/or exon 4; the mutation is alters the expression, activation, or dimerization of an Ikaros gene product; the mutation is a deletion of a portion of exon 7.

In yet other preferred embodiments the Ikaros transgene includes an Ikaros transcriptional control region operably linked to a sequence which is functionally unrelated to the Ikaros gene, or which is less than 50% homologous with the Ikaros gene, e.g., a nucleic acid encoding a reporter molecule, a nucleic acid encoding a toxin, or a nucleic acid encoding a gene to be placed under the control of an Ikaros regulatory region.

In yet other preferred embodiments the Ikaros transgene encodes: an Ikaros protein which is a competitive inhibitor or an antagonist of a naturally occurring Ikaros protein; an Ikaros gene genetically engineered, e.g., by deletion of an exon, or by using a sequence which results in expression in a preselected tissue, to encode a specific isoform, or a specific subset of Ikaros isoforms, e.g., the transgene is genetically engineered to express one of mIK-1, mIK-2, mIK-3, mIK-4, mIK-5, hIK-1, hIK-2, hIK-3, hIK-4, or hIK-5.

In preferred embodiments the transgenic animal or cell: is heterozygous for an Ikaros transgene; homozygous for an Ikaros transgene; includes a first Ikaros transgene and a second Ikaros transgene; includes an Ikaros transgene and a second transgene which is other than an Ikaros transgene.

In preferred embodiments, the evaluating step includes determining the effect of the treatment on a parameter related to the nervous system. The parameter related to the nervous system can, e.g., be any of: the presence, function, or morphology of cells (or their progenitors) of a nervous tissue, e.g., neurons, glial cells, brain cells, or cells of the basal ganglia, e.g., cells of the corpus striatum, cells of the substantia nigra; resistance to infection. life span; body weight; the presence, function, or morphology of tissues or organs of the nervous system; the expression of a gene, e.g., the Ikaros transgene.

In preferred embodiments the evaluating step includes evaluating the expression of a gene or transgene, e.g., a gene which encodes a component of the nervous system, e.g., a cell surface marker, or a receptor, the Ikaros gene, or an Ikaros transgene.

In preferred embodiments the evaluating step includes evaluating the growth rate of a transgenic cell.

In preferred embodiments the treatment can include: the administration of a drug, chemical, or other substance; the administration of ionizing radiation; the administration of an antibody, e.g., an antibody directed against a molecule or cell of the nervous system; administration of a substance or other treatment which suppresses the immune system; or administration of a substance or other treatment which activates or boosts the function of the immune system; introduction of a nucleic acid, e.g., a nucleic acid which encodes or expresses a component of the nervous system; the introduction of a protein, e.g., a protein which is a component of the immune system.

In another aspect, the invention features, a method for evaluating the effect of a treatment on a disorder of the nervous system including administering the treatment to a cell or animal having an Ikaros transgene, and evaluating the effect of the treatment on the cell or animal.

In preferred embodiments the disorder is: related to the presence, function, or morphology of cells (or their progenitors) of a nervous tissue, e.g., neurons, glial cells, brain cells, or cells of the basal ganglia, e.g., cells of the corpus striatum, cells of the substantia nigra; trauma; Alzheimer's disease; Parkinson's disease; or Huntington's disease.

In preferred embodiments using a transgenic animal the transgenic animal is a mammal, e.g., a non-human mammal, e.g., a nonhuman primate or a swine, a monkey, a goat, or a rodent, e.g., a rat, but preferably a mouse.

In preferred embodiments using a transgenic cell the transgenic cell is a mammalian cell, e.g., a non-human mammalian cell, e.g., a swine, a monkey, a goat, or a rodent, preferably a mouse, cell.

In other preferred embodiments: the Ikaros transgene includes a mutation. In yet more preferred embodiments the Ikaros transgene includes a mutation and: the mutation is, or results from, a chromosomal alteration; the mutation is, or results from, any of an alteration resulting from homologous recombination, site-specific recombination, nonhomologous recombination; the mutation is, or results from, any of an inversion, deletion, insertion, translocation, or reciprocal translocation; the mutation is, or results from, any of a deletion of one or more nucleotides from the gene, an addition of one or more nucleotides to the gene, a change of identity of one or more nucleotides of the gene.

In yet other preferred embodiments the Ikaros transgene includes a mutation and: the mutation results in mis-expression of the transgene or of another gene in the animal; the mutation results in mis-expression of the transgene and the mis-expression is any of an alteration in the level of a messenger RNA transcript of the transgene, the presence of a non-wild type splicing pattern of a messenger RNA transcript of the transgene, or a non-wild type level of a protein encoded by the transgene; the mutation alters the relative abundance of a first Ikaros isoform with respect to a second Ikaros isoform, as compared, e.g., to a wild type animal or to an animal lacking the transgene; the mutation is in, or alters, the sequence, expression, or splicing of one or more of the following exons: exon 1/2, exon 3, exon 4, exon 5, exon 6, and exon 7; the mutation is in, or alters, the sequence, expression, or splicing of a DNA binding domain of, the Ikaros gene or DNA; the mutation is a deletion of portions of exon 3 and/or exon 4; the mutation is alters the expression, activation, or dimerization of an Ikaros gene product; the mutation is a deletion of a portion of exon 7.

In yet other preferred embodiments the Ikaros transgene includes an Ikaros transcriptional control region operably linked to a sequence which is functionally unrelated to the Ikaros gene, or which is less than 50% homologous with the Ikaros gene, e.g., a nucleic acid encoding a reporter molecule, a nucleic acid encoding a toxin, or a nucleic acid encoding a gene to be placed under the control of an Ikaros regulatory region.

In yet other preferred embodiments the Ikaros transgene encodes: an Ikaros protein which is a competitive inhibitor or an antagonist of a naturally occurring Ikaros protein; an Ikaros gene genetically engineered, e.g., by deletion of an exon, or by using a sequence which results in expression in a preselected tissue, to encode a specific isoform, or a specific subset of Ikaros isoforms, e.g., the transgene is genetically engineered to express one of mIK-1, mIK-2, mIK-3, mIK-4, mIK-5, hIK-1, hIK-2, hIK-3, hIK-4, or hIK-5.

In preferred embodiments the transgenic animal or cell: is heterozygous for an Ikaros transgene; homozygous for an Ikaros transgene; includes a first Ikaros transgene and a second Ikaros transgene; includes an Ikaros transgenic and a second transgene which is other than an Ikaros transgene.

In preferred embodiments, the evaluating step includes determining the effect of the treatment on a parameter related to the nervous system. The parameter related to the nervous system can, e.g., be any of: the presence, function, or morphology of cells (or their progenitors) of a nervous tissue, e.g., neurons, glial cells, brain cells, or cells of the basal ganglia, e.g., cells of the corpus striatum, cells of the substantia nigra; resistance to infection; life span; body weight; the presence, function, or morphology of tissues or organs of the nervous system; the expression of a gene, e.g., the Ikaros transgene.

In preferred embodiments the evaluating step includes evaluating the expression of a gene or transgene, e.g., a gene which encodes a component of the nervous system, e.g., a cell surface marker, or a receptor, the Ikaros gene, or an Ikaros transgene.

In preferred embodiments the evaluating step includes evaluating the growth rate of a transgenic cell.

In preferred embodiments the treatment can include: the administration of a drug, chemical, or other substance; the administration of ionizing radiation; the administration of an antibody, e.g., an antibody directed against a molecule or cell of the nervous system; administration of a substance or other treatment which suppresses the immune system; or administration of a substance or other treatment which activates or boosts the function of the immune system; introduction of a nucleic acid, e.g., a nucleic acid which encodes or expresses a component of the nervous system; the introduction of a protein, e.g., a protein which is a component of the immune system.

The term "Ikaros" as used herein to refer to a gene, a transgene, or a nucleic acid, refers to a nucleic acid sequence which is at least about 50%, preferably at least about 60%, more preferably at least about 70%, yet more preferably at least about 80%, most preferably at least about 90%–100% homologous with a naturally occuring Ikaros gene or portion thereof, e.g., with the nucleic acid sequence of human Ikaros as shown in SEQ ID NO:2 (FIG. 2) or of mouse Ikaros as shown in SEQ ID NO:1 (FIG. 1).

As used herein, the term "transgene" refers to a nucleic acid sequence (encoding, e.g., one or more Ikaros proteins), which is inserted by artifice into a cell. The transgene can become part of the genome of an animal which develops in whole or in part from that cell. If the transgene is integrated into the genome it results in a change in the nucleic acid sequence of the genome into which it is inserted. A transgene can be partly or entirely species-heterologous, i.e., the transgene, or a portion thereof, can be from a species which is different from the cell into which it is introduced. A transgene can be partly or entirely species-homologous, i.e., the transgene, or a portion thereof, can be from the same species as is the cell into which it is introduced. If a transgene is homologous (in the sequence sense or in the species-homologous sense) to an endogenous gene of the cell into which it is introduced, then the transgene, preferably, has one or more of the following characteristics: it is designed for insertion, or is inserted, into the cell's genome in such a way as to alter the sequence of the genome of the cell into which it is inserted (e.g., it is inserted at a location which differs from that of the endogenous gene or its insertion results in a change in the sequence of the endogenous endogenous gene); it includes a mutation, e.g., a mutation which results in misexpression of the transgene; by virtue of its insertion, it can result in misexpression of the gene into which it is inserted, e.g., the insertion can result in a knockout of the gene into which it is inserted. A transgene can include one or more transcriptional regulatory sequences and any other nucleic acid sequences, such as introns, that may be necessary for a desired level or pattern of expression of a selected nucleic acid, all operably linked to the selected nucleic acid. The transgene can include an enhancer sequence. The transgene is typically introduced into the animal, or an ancestor of the animal, at a prenatal, e.g., an embryonic stage.

As used herein, an Ikaros transgene, is a transgene which includes all or part of an Ikaros coding sequence or regulatory sequence. Included are transgenes: which upon insertion result in the missexpression of an endogenous Ikaros gene; which upon insertion result in an additional copy of an Ikaros gene in the cell; which upon insertion place a non-Ikaros gene under the control of an Ikaros regulatory region. Also included are transgenes: which include a copy of the Ikaros gene having a mutation, e.g., a deletion or other mutation which results in misexpression of the transgene (as compared with wild type); which include a functional copy of an Ikaros gene (i.e., a sequence having at least 5% of a wild type activity, e.g., the ability to support the development of T, B, or NK cells); which include a functional (i.e., having at least 5% of a wild type activity, e.g., at least 5% of a wild type level of transcription) or nonfunctional (i.e., having less than 5% of a wild type activity, e.g., less than a 5% of a wild type level of transcription) Ikaros regulatory region which can (optionally) be operably linked to a nucleic acid sequence which encodes a wild type or mutant Ikaros gene product or, a gene product other than an Ikaros gene product, e.g., a reporter gene, a toxin gene, or a gene which is to be expressed in a tissue or at a developmental stage al which Ikaros is expressed. Preferably, the transgene includes at least 10, 20, 30, 40, 50, 100, 200, 500, 1,000, or 2,000 base pairs which have at least 50, 60, 70, 80, 90, 95, or 99% homology with a naturally occurring Ikaros sequence.

As used herein, the term "transgenic cell" refers to a cell containing a transgene.

As used herein, a "transgenic animal" is any animal, e.g, a non-human mammal, e.g., a swine, a monkey, a goat, or a rodent, e.g., a mouse, in which one or more, and preferably essentially all, of the cells of the animal include a transgene. The transgene is introduced into the cell, directly or indirectly by introduction into a precursor of the cell, by way of deliberate genetic manipulation, such as by micro-injection or by infection with a recombinant virus. The term genetic manipulation is directed to the introduction of a recombinant DNA molecule. This molecule may be integrated within a chromosome, or it may be extrachromosomally replicating DNA.

The "transgenic animals" of the invention are preferably produced by introducing "transgenes" into the germline of an animal. Embryonal target cells at various developmental stages can be used to introduce transgenes. Different methods are used depending on the stage of development of the embryonal target cell. The zygote is the best target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al. (1985) *Proc. Natl. Acad. Sci. USA* 82:4438–4442). As a consequence, all cells of the transgenic mammal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

Retroviral infection can also be used to introduce transgene into a mammal. The developing mammalian embryo can be cultured in vitro to the blastocyst stage. During this time, the blastomeres can be targets for retroviral infection (Jaenich, R. (1976) *Proc. Natl. Acad. Sci. USA* 73:1260–1264). Efficient infection of the blastomeres is obtained by enzymatic treatment to remove the zona pellucida (Manipulating the Mouse Embryo, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *Proc. Natl. Acad. Sci. USA* 82:6927–6931; Van der Putten et al. (1985) *Proc. Natl. Acad. Sci. USA* 82:6148–6152). Transfection is easily and efficiently obtained by culturing the blastomeres on a monolayer of virus-producing cells (Van der Putten et al. (1985) *Proc. Natl. Acad. Sci. USA* 82:6148–6152; Stewart et al. (1987) *EMBO J*. 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1985) *Proc. Natl. Acad. Sci. USA* 82:6927–6931).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *Proc. Natl. Acad. Sci. USA* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a mammal. The ES cells thereafter colonize the embryo and contribute to the germ line of the resulting chimeric animal. For a review see Jaenisch, R. (1988) *Science* 240:1468–1474; Sedivy, J. M. and Joyner, A. L. (1992) "Gene Targeting" (W.H. Freeman and Company, N.Y.) 123–142.

For construction of transgenic mice, procedures for embryo manipulation and microinjection are described in, for example, *Manipulating the Mouse Embryo*, (Cold Spring Harbor Laboratory Press, Cold Spring Harbor, N.Y., 1986). Similar methods are used for production of other transgenic animals. In an exemplary embodiment, mouse zygotes are collected from six week old females that have been superovulated with pregnant mares serum (PMS) followed 48 hours later with human chorionic gonadotropin. Primed females are placed with males and checked for vaginal plugs on the following morning. Pseudopregnant females are selected for estrus, placed with proven sterile vasectomized males and used as recipients. Zygotes are collected and cumulus cells removed. Pronuclear embryos are recovered from female mice mated to males. Females are treated with pregnant mare serum, PMS, to induce follicular growth and human chorionic gonadotropin, hCG, to induce ovulation. Embryos are recovered in a Dulbecco's modified phosphate buffered saline (DPBS) and maintained in Dulbecco's modified essential medium (DMEM) supplemented with 10% fetal bovine serum.

Microinjection of an Ikaros transgene encoding can be performed using standard micromanipulators attached to a microscope. For instance, embryos are typically held in 100 microliter drops of DPBS under oil while being microinjected. DNA solution is microinjected into the male pronucleus. Successful injection is monitored by swelling of the pronucleus. Immediately after injection embryos are transferred to recipient females, e.g. mature mice mated to vasectomized male mice. In a general protocol, recipient females are anesthetized, paralumbar incisions are made to expose the oviducts, and the embryos are transformed into the ampullary region of the oviducts. The body wall is sutured and the skin closed with wound clips.

Transgenic animals can be identified after birth by standard protocols. For instance, at three weeks of age, about 2–3 cm long tail samples are excised for DNA analysis. The tail samples are digested by incubating overnight at 55° C. in the presence of 0.7 ml 50 mM Tris, pH 8.0, 100 mM EDTA, 0.5% SDS and 350 mg of proteinase K. The digested material is extracted once with equal volume of phenol and once with equal volume of phenol:chloroform (1:1 mixture). The supernatants are mixed with 70 ml 3M sodium acetate (pH 6.0) and the nucleic acid precipitated by adding equal volume of 100% ethanol. The precipitate is collected by cetrifugation, washed once with 70% ethanol, dried and dissolved in 100 ml TE buffer (10 mM Tris, pH 8.0 and 1 mM EDTA). The DNA is then cut with BamHI and BglII or EcoRI (or other frequent DNA cutter), electrophoresed on 1% agarose gels, blotted onto nitrocellulose paper and hybridized with labeled primers under very stringent conditions in order to discern between wild-type and mutant receptor genes. Alternatively, a ligation chain reaction (LCR) (see, e.g., Landegran et al. (1988) *Science* 241:1077–1080; and Nakazawa et al. (1944) *Proc. Natl. Acad. Sci. USA* 91:360–364), which is useful for detecting point mutations, can be used to determine the presence of the transgene in the neonate.

The resulting transgenic mice or founders can be bred and the offspring analyzed to establish lines from the founders that express the transgene. In the transgenic animals, multiple tissues can be screened to observe for endothelial cell and parenchymal cell expression. RNA studies in the various transgenic mouse lines will allow evaluation of independence of the integration site to expression levels of the transgene.

Mis-expression, as used herein, refers to a non-wild type pattern of gene expression. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of the tissue specificity of expression, e.g., increased or decreased expression (as compared with wild type) in a predetermined cell type or tissue type; a pattern of expression that differs from wild type in terms of the size, amino acid sequence, post-translational modification, or a biological activity of an Ikaros gene product; a pattern of expression that differs from wild type in terms of the effect of an environmental stimulus or extracellullar stimulus on expression of the gene, e.g., a pattern of increased or decreased expression (as compared with wild type) in the presence of an increase or decrease in the strength of the stimulus; or a pattern of isoform expression which differs from wild type.

An Ikaros-responsive control element, as used herein is a region of DNA which, when present upstream or downstream from a gene, results in regulation, e.g., increased transcription of the gene in the presence of an Ikaros protein.

Purified DNA is DNA that is not immediately contiguous with both of the coding sequences with which it is immediately contiguous (i.e., one at the 5' end and one at the 3' end) in the naturally occurring genome of the organism from which the DNA of the invention is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other DNA sequences. It also includes a recombinant DNA which is part of a hybrid gene encoding additional polypeptide sequence.

Homologous refers to the sequence similarity between two polypeptide molecules or between two nucleic acid molecules. When a position in both of the two compared sequences is occupied by the same base or amino acid monomeric subunit, e.g., if a position in each of two DNA molecules is occupied by adenine, then the molecules are homologous at that position. The homology between two sequences is a function of the number of matching or homologous positions shared by the two sequences. For example, 6 of 10, of the positions in two sequences are matched or homologous then the two sequences are 60% homologous. By way of example, the DNA sequences ATTGCC and TATGGC share 50% homology.

The terms peptide, protein, and polypeptide are used interchangeably herein.

A peptide has Ikaros activity if it has one or more of the following properties: the ability to stimulate transcription of a DNA sequence under the control any of a δA element, an NFKB element, or one of the Ikaros binding oligonucleotide consensus sequences disclosed herein; the ability to bind to any of a δA element, an NFKB element, or one of the Ikaros binding oligonucleotide consensus sequences disclosed herein; or the ability to competitively inhibit the binding of a naturally occurring Ikaros isoform to any of a δA element, an NFKB element, or one of the Ikaros binding oligonucleotide consensus sequences disclosed herein. An Ikaros peptide is a peptide with Ikaros activity.

"Ikaros antagonists", as used herein, refers to Ikaros isoforms arising naturally or by mutagenesis (including in vitro shuffling) which can inhibit at least one biological activity of a naturally occurring Ikaros protein. In preferred embodiments, the Ikaros antagonist is an inhibitor of: Ikaros-mediated transcriptional activation, e.g. it is a competitive inhibitor of Ikaros binding to Ikaros responsive elements, such as IK-BS1, IK-BS2, IK-BS4, IK-BS5, IK-BS6, IK-BS7, IK-BS8, or IK-BS9; or it is an inhibitor of protein—protein interations of transcriptional complexes formed with naturally occurring Ikaros isoforms.

As used herein, the term "exon", refers to those gene (e.g. DNA) sequences which are transcribed and processed to form mature messenger RNA (mRNA) encoding an Ikaros protein, or portion thereof, e.g. Ikaros coding sequences, and which, at the chromosomal level, are interrupted by intron sequences. Exemplary exons of the subject Ikaros proteins and genes include: with reference to SEQ ID NO:4 (mIk-1), the nucleotide sequence encoding exon 1/2 (E1/2) corresponding to Met-1 through Met-53; the nucleotide sequence encoding exon 3 (E3) corresponding to Ala-54 through Thr-140; the nucleotide sequence encoding exon 4 (E4) corresponding to Gly-141 through Ser-196; the nucleotide sequence encoding exon 5 (E5) corresponding to Val-197 through Pro-237; the nucleotide sequence encoding exon 6 (6) corresponding to Val-238 through Leu-282; the nucleotide sequence encoding exon 7 (E7) corresponding to Gly-283 through Ser-518; with reference to SEQ ID NO:2 (hIk-1), the nucleotide sequence encoding exon 3 (E3) corresponding to Asn-1 through Thr-85; the nucleotide sequence encoding exon 4 (E4) corresponding to Gly-86 through Ser-141; the nucleotide sequence encoding exon 5 (E5) corresponding to Val-142 through Pro-183; the nucleotide sequence encoding exon 6 (6) corresponding to Val-184 through Leu-228; the nucleotide sequence encoding exon 7 (E7) corresponding to Gly-229 through Ser-461. The term "intron" refers to a DNA sequence present in a given Ikaros gene which is not translated into protein and is generally found between exons. The term "gene" refers to a region of chromosomal DNA which contains DNA sequences encoding an Ikaros protein, including both exon and intron sequences. A "recombinant gene" refers to nucleic acid encoding an Ikaros protein and comprising Ikaros exon sequence, though it may optionally include intron sequences which are either derived from a chromosomal Ikaros gene or from an unrelated chromosomal gene. An exemplary recombinant gene is a nucleic acids having a sequence represented by any of SEQ ID NOS:1–7 or 13.

The term "Ikaros responsive element" or "IK-RF", refers to nucleic acid sequences which, when placed in proximity of a gene, act as transcriptional regulatory elements which control the level of transcription of the gene in an Ikaros protein-dependent manner. Exemplary IK-RE, as described below, include IK-BS1, IK-BS2, IK-BS4, IK-BS5, IK-BS6, IK-BS7, IK-BS8, or IK-BS9.

Ikaros: A Master Regulator of Hemopoietic Differentiation

The Ikaros gene is described briefly here A more detailed treatment can be found in the copending U.S. patent application referred to above. A hemopoietic stem cell in the appropriate microenvironment will commit and differentiate into one of many cell lineages. Signal transduction molecules and transcription factors operating at distinct check points in this developmental pathway will specify the cell fate of these early progenitors. Such molecules are viewed as master regulators in development but also serve as markers for the relatively poorly defined stages of early hemopoiesis.

In search of a lymphoid restricted transcriptional enhancer, in control of gene expression in early T cells, the Ikaros gene family was isolated, which encode zinc finger DNA binding proteins. In the early embryo, the Ikaros gene is expressed in the hemopoietic liver but from mid to late gestation becomes restricted to the thymus. The only other embryonic site with Ikaros mRNA is a small area in the corpus striatum. In the adult, the Ikaros mRNA is detected only in the thymus and in the spleen (Georgopoulos, K. et al. (1992) *Science* 258:808). The Ikaros gene functions as a transcriptional enhancer when ectopically expressed in non lymphoid cells.

The Ikaros gene plays an important role in early lymphocyte and T cell differentiation. The Ikaros gene is abundantly expressed at early embryonic hemopoietic sites is later on restricted in the developing thymus. The thymus together with the spleen are the prime sites of expression in the adult. This highly enriched expression of the Ikaros gene was also found in early and mature primary T cells and cell lines. This restricted pattern of expression of the Ikaros gene at sites where embryonic and adult T cell progenitors originate together with the ability of the encoded protein to activate transcription from the regulatory domain of an early T cell differentiation antigen supported a determining role in T cell specification.

Differential splicing at the Ikaros genomic locus generates at least five transcripts (Ik-1, Ik-2, Ik-3, Ik-4 and Ik-5) that encode proteins with distinct DNA binding domains. A high level of conservation was found between the human and mouse homologs of the Ikaros gene. The human and mouse Ikaros proteins exhibit nearly 100% identity at their N-terminal zinc finger domain (F1) which was shown to determine the DNA binding specificity of these proteins. In the mouse, differential splicing allows for the distinct combinations of zinc finger modules present in the Ik-1, Ik-2 Ik-3 and Ik-4 isoforms. This differential usage of zinc finger modules in the mouse isoforms establishes the basis of their distinct DNA binding properties and abilities to activate transcription. Differential splicing of the exons encoding the zinc finger DNA binding modules is also manifested in the human Ikaros gene and generates at least two isoforms homologues of the mouse Ik-1 and Ik-4.

These Ikaros protein isoforms (IK-1, IK-2, IK-3, IK-4, IK-5) have overlapping but also distinct DNA binding specificity dictated by the differential usage of zinc finger modules at their N-terminus. In the mouse isoforms (hereinafter designated "mIk"), and presumably in the human isoforms (hereinafter designated "hIk"), the core binding site for four of the Ikaros proteins is the GGGA motif but outside this sequence their specificity differs dramatically. The mIK-3 protein shows strong preferences for bases at both the 5' and 3' flanking sequences which restricts the number of sites it can bind to. The mIk-1 protein also exhibits strong preference for some of these flanking bases and can bind to wider range of sequences. The mIk-2 protein, the most promiscuous of the three proteins, can bind to sites with just the GGGAa/t motif. Finally, the mIk-4 protein with similar sequences specificity to mIk-1 binds with high affinity only when a second site is in close proximity suggesting cooperative site occupancy by this protein. Given the identity between the human and mouse Ik-1 and Ik-4 DNA binding domains, the human isoforms are expected to bind similar sequences to their mouse homologues and regulate transcription in a similar fashion. This extreme species conservation between these two functionally diverse Ikaros isoforms support an important role for these proteins in lymphocyte transcription. The C-terminal domain shared by all of the mouse and human Ikaros isoforms is also highly conserved. This portion of the Ikaros proteins contains conserved acidic motifs implicated as transcription activation domains.

Figure 7:
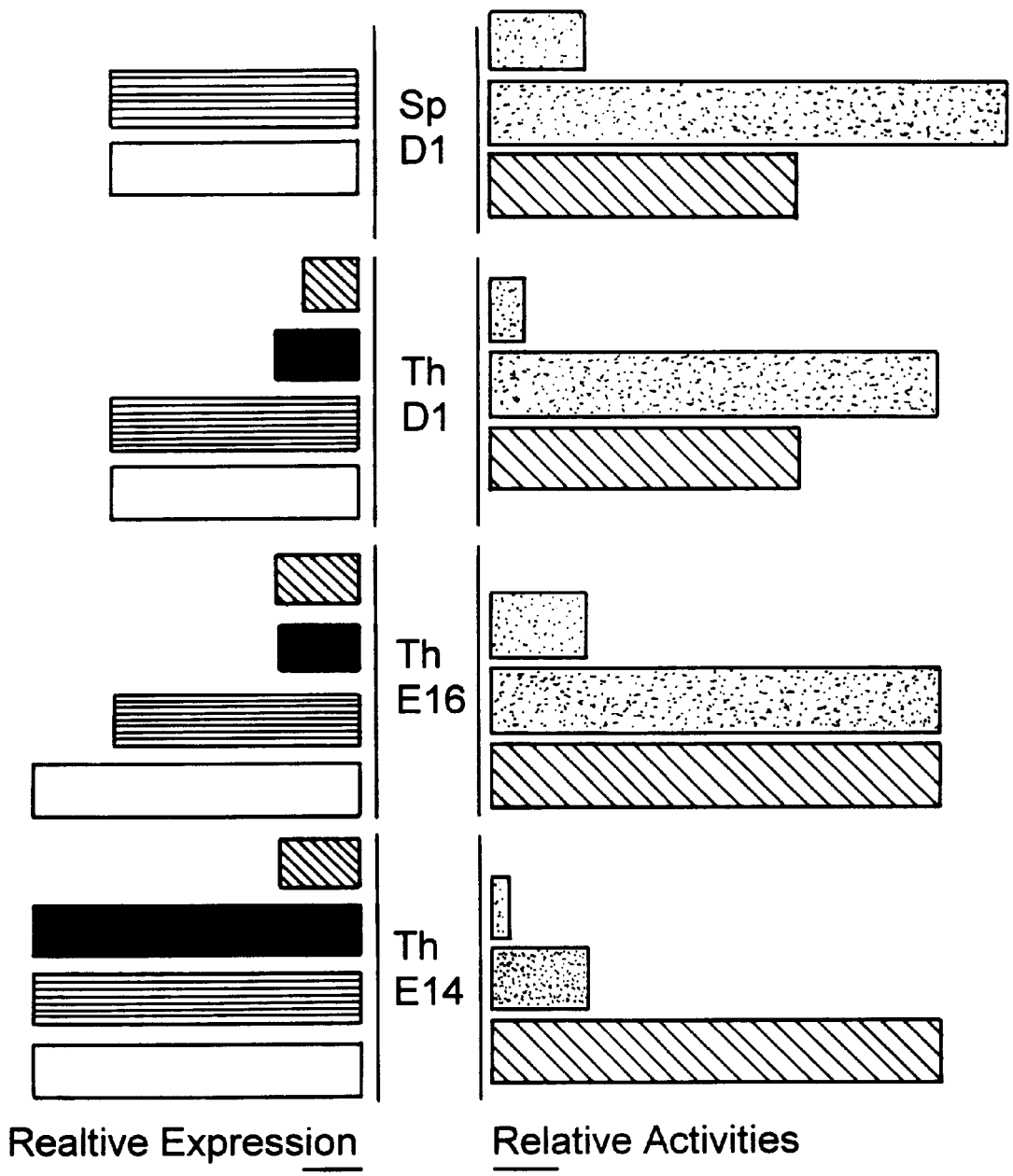
FIG. 7 is a model of Ikaros isoform control of differential gene expressions. Th=thymus; Sp=spleen; Ex=day of embryonic development; Dx=day of postnatal life. The left hand column represents the relative expression of an isoform at a given developmental stage. Open bar=mIk-1; Horizontal stripes=mIk-2; Diagonal stripes=mIk-3; and solid bar=mIk-4. The right hand side shows the resulting reactivity of Ikaros binding sites at a given developmental stage. Light bars=low affinity sites (sites at which isoforms 1, 2, 3 and 4 bind with similar affinities); Dark bars=high affinity inverted or direct repeat containing sites (e.g., NFKB sites, Ik1–4 bind with high affinity); Diagonal bars=single high affinity sites (sites where Ik1 and Ik2 bind but Ik3 and Ik4 don't bind (and therefore won't attenuate the binding of mIk-1 and mIk-2).

The embryonic expression pattern and activation potential of the Ikaros isoforms are also markedly distinct. The stronger transcriptional activators, Ik-1 and Ik-2, are found in abundance in the early fetal liver, in the maturing thymus and in a small area in the developing brain, whereas the weak activators, e.g. Ik-3 and Ik-4, are present at significantly lower levels in these tissues during these times. Consequently, Ik-1 and Ik-2 are expected to play a primary role in transcription from sites that can bind all four of the Ikaros proteins. However, in the early embryonic thymus and in the late mid-gestation hemopoietic liver the weak activator Ik-4 is expressed at similar mRNA levels to the Ik-1 and Ik-2 isoforms. The Ik-4 weak activator can bind only to composite sites while Ik-1 and Ik-2 can bind to a range of single and composite sites. The Ik-1 and Ik-2 proteins recruited to composite sites (a fraction of the total protein), during early to mid gestation, will have to compete for binding with the Ik-4 isoform, solely recruited to these sites. Consequently the activity of these composite sites may be primarily controlled by the Ik-4 isoform, a weak transcription activator. Modulation of Ik-4 expression in the developing thymocyte, in combination with steady levels of the Ik-1 and Ik-2 expression may determine the temporal and stage specific expression of T cell differentiation antigens. Low affinity binding sites for these proteins may also become transcriptionally active in the late stages of T cell development when the most potent activators, Ik-1 and lk-2, accumulate. In the fly embryo the NF-κB/rel homologue Dorsal, a maternal morphogen, engages in interactions with transcriptional factors binding to adjacent sites. These protein-protein interactions determine the activation level and threshold response from low and high affinity binding sites (Jiang et al. (1993) *Cell* 72:741–752). The transcriptional activity of the Ikaros proteins may be further regulated by such mechanisms in the developing lymphocyte. In addition, the activity of the Ikaros proteins may be under postranslational control operating during both lymphocyte differentiation and activation. FIG. 7 provides a model in which the relative concentrations of Ikaros isoforms at different developmental stages confer different reactivites on the various sites.

The transcriptional activity of the mIk-3 and mIk-4 proteins may be further regulated by T cell restricted signals mediating postranslational modifications or by protein-protein interactions. The mIk-4 protein binds NFkB motif in a cooperative fashion and may therefore interact in situ with other members of the Ikaros or of the NFkB family. These protein-protein-DNA complexes may dictate a differential transcriptional outcome.

The differential expression of the Ikaros isoforms during T cell ontogeny, their overlapping but also unique binding specificities and their diverse transcriptional potential may be responsible for the orderly activation of stage specific T cell differentiation markers. Multiple layers of gene expression in developing lymphocytes may be under the control of these Ikaros proteins. Synergistic interactions and/or competition between members of the Ikaros family and other transcription factors in these cells on qualitatively similar and distinct target sites could dictate the complex and ever changing gene expression in the differentiating and activated lymphocyte. This functional dissection of the Ikaros gene strongly suggest it functions as a master gene in lymphocytes, and an important genetic switch for early hemopoiesis and both B and r cell development.

The Ikaros gene maps to the proximal arm of human chromosome 7 between p11.2 and p13 next to Erbb In the mouse the Ikaros gene maps to the proximal arm of chromosome 11 tightly linked to Erbb. Other genes linked to the Ikaros locus in the mouse are the Leukemia inhibitory factor (Lif) and the oncogene Rel a member of the NFK-B family. All three of the genes linked to the Ikaros gene in the mouse appear to play an important role in the development of the hemopoietic system. The tight linkage between the Erbb and the Ikaros genes on syntenic loci in the mouse and human may be related to their genetic structure and regulation. Nevertheless, no known mutations were mapped to the Ikaros locus in the mouse. However, this does not preclude the importance of the Ikaros gene for the lymphopoietic system. Naturally occurring mutations that affect development of the immune system may not be readily obtained in mice since such mutant animals may only thrive under special care conditions That the Ikaros gene is a fundamentally important regulator of lymphocyte development is substantiated by analysis of its human homologue. The overall conservation of the Ikaros proteins between mice and man at the genetic level and protein level but also their restricted pattern of expression in the developing lymphocyte, e.g. in maturing T cells, e.g. in maturing B cell, strongly support their participation in the same regulatory pathway across species.

Cloning the Mouse Ikaros Gene

A T cell expression cDNA library from the mature T cell line E14 was constructed into the A ZAP phage vector.

A multimerized oligonucleotide encoding sequence (SEQ ID NO:14) from one of the protein binding sites of the CD38 enhancer was used as a radiolabeled probe to screen this expression library for the T cell specific proteins that bind and mediate enhancer function by the southwestern protocol of Singh and McKnight. Four gene encoding DNA binding proteins were isolated. One, the Ikaros gene, encoded a T cell specific protein.

The Sequence of Mouse Ikaros

The sequence of the Ikaros gene was determined using the Sanger dideoxyl sequencing protocol. The derived amino acid sequence was determined using the MAP program of GCG (available from the University of Wisconsin) and Strider sequence analysis progruns. FIG. 1 provides the sequence of a mouse Ikaros cDNA (mIk-2) and the derived amino acid sequence encoded thereby (SEQ ID NO:1). Sequence information for other isoforms of mouse Ikaros proteins (and cDNAs) are provided in SEQ ID NO:3 (mIk-3), SEQ ID NO:4 (mIk-1), SEQ ID NO:5 (mIk-4), and SEQ ID NO:6 (mIk-5).

A Mouse Ikaros Protein

The Ikaros protein shown in FIG. 1 (mIk-2) is comprised of 431 amino acids with five $CX_2CX_{12}HX_3H$ zinc finger motifs organized in two separate clusters. (See also FIG. 4.) The first cluster of three fingers is located 59 amino acids from the initiating methionine, while the second cluster is found at the C terminus of the protein 245 amino acids downstream from the first. Two of the finger modules of this protein deviate from the consensus amino acid composition of the Cys-His family of zinc fingers; finger 3 in the first cluster and finger 5 at the C terminus have four amino acids between the histidine residues. This arrangement of zinc fingers in two widely separated regions is reminiscent of that of the Drosophila segmentation gap gene Hunchback. Similarity searches in the protein data base revealed a 43% identity between the second finger cluster of Ikaros and Hunchback at the C terminus of these molecules. This similarity at the C terminus of these proteins and the similar arrangement of their finger domains raises the possibility that these proteins are evolutionary related and belong to a subfamily of zinc finger proteins conserved across species.

Ikaros Isoforms

Figure 4:
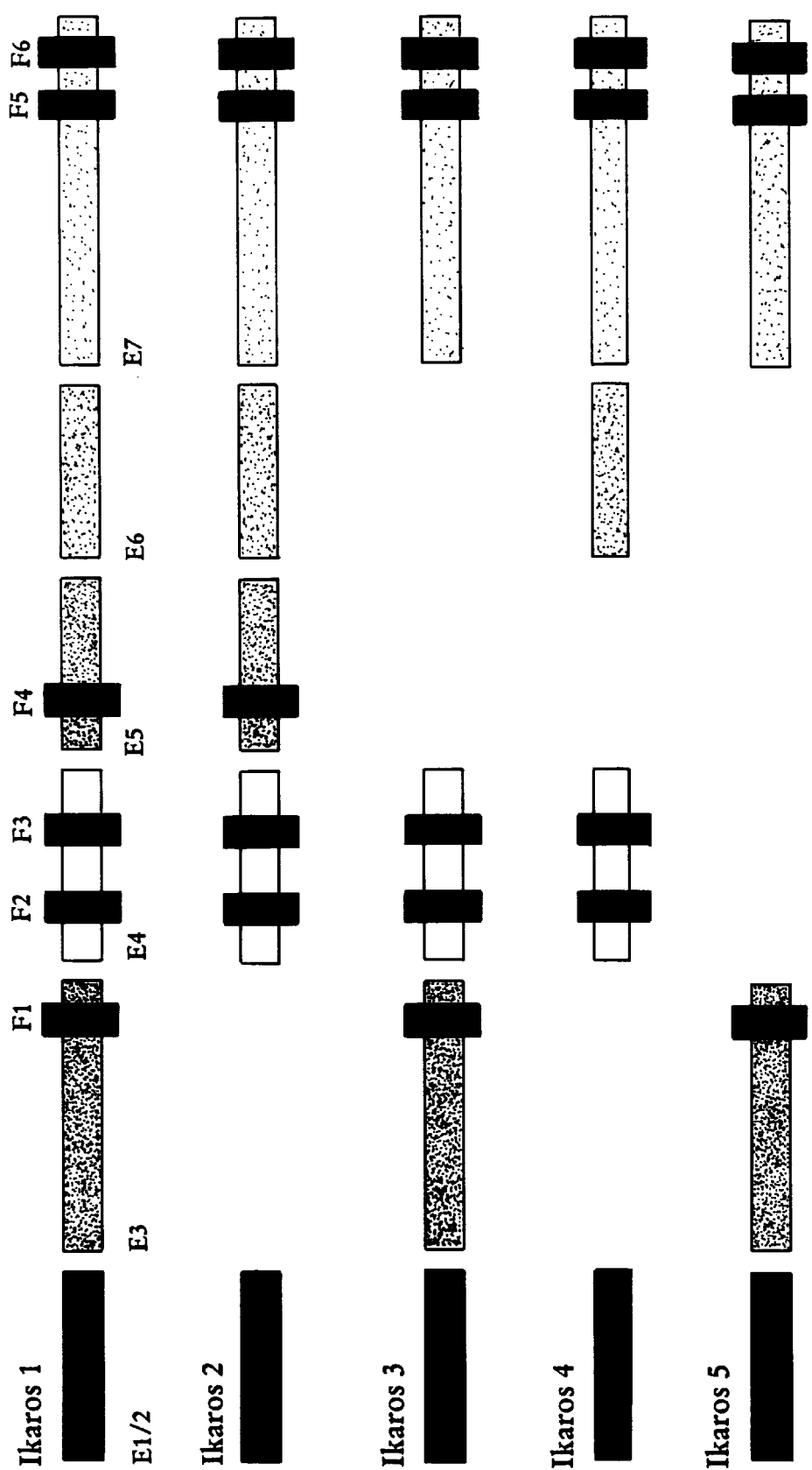
FIG. 4 is a diagram of exon usage in the Ikaros 1–5 cDNAs. Exon numbers are indicated at the bottom left hand corner of each box (Ex). Zinc finger modules are shown on top of the encoding exons (Fx).
Figure 5:
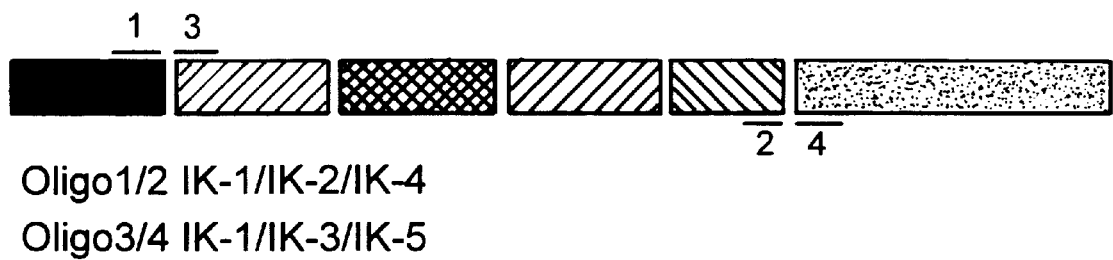
FIG. 5 is a depiction of the exon organization at the Ikaros locus indicating primer sets 1/2 and 3/4 used for amplification of the respective isoforms.

In addition to the cDNA corresponding to mIk-2, four other cDNAs produced by differential splicing at the Ikaros genomic locus were cloned. These isoform encoding cDNAs were identified using a 300 bp fragment from the 3' of the previously characterized Ikaros cDNA (mIk-2, FIG. 1). As shown in FIGS. 3 and 4, each isoform is derived from three or more of six exons, referred to as E1/2, E3, E4, E5, E6 and E7. All five cDNAs share exons E1/2 and E7 encoding respectively for the N-53 and C-terminal 236 amino acid domains. These five cDNAs consist of different combinations of exons E3-6 encoding the N-terminal zinc finger domain. The mIk-1 cDNA (SEQ ID NO:4) encodes a 57.5 kD protein with four zinc fingers at its N-terminus and two at its C-terminus and has the strongest similarity to the Drosophila segmentation protein Hunchback (Zinc fingers are indicated as F1, F2+F3, F4, and F5+F6 in FIG. 4). The mIk-2 (SEQ ID NO:1) and mIk-3 (SEQ ID NO:3) cDNAs encode 48 kd proteins with overlapping but different combinations of zinc fingers. The mIk-3 isoform contains fingers 1, 2, 3 while mIk-2 contains fingers 2, 3 and 4. The 43.5 kD mIk-4 protein (SEQ ID NO:5) has two fingers at its N-terminus also present in mIk-1 and mIk-2. The mIk-5 cDNA (SEQ ID NO:6) encodes a 42 kd protein with only one N-terminal finger shared by mIk-1 and mik-3. This differential usage of the zinc finger modules by the Ikaros proteins support an overlapping but differential DNA binding specificity.

cDNA cloning of isoforms was performed as follows. A cDNA library made from the T cell line EL4 in λZAP was screened at high stringency with a 300 bp fragment from the 3' of the previously described Ikaros cDNA (isoform 2). Positive clones were characterized by sequencing using an antisense primer from the 5' of exon 7.

Cloning of the Human Ikaros Gene

A DNA fragment derived from the shared 3' coding region of the mouse Ikaros cDNAs was used as a probe to screen for human Ikaros homologs. This DNA fragment, which encodes the C-terminal part of the Ikaros proteins, is believed to be essential for their activity and does not exhibit significant sequence similarities with other DNA binding proteins. A cDNA library from the human T cell line Jurkat was screened at high stringency and 9 partial cDNAs were isolated. The most full length cDNA and its deduced amino acid sequence is shown in FIG. 2 (SEQ ID NO:2). This cDNA encodes a protein homologous to the mouse Ik-1 isoform, the largest of the mouse Ikaros proteins comprised of all the translated exons. A high degree of conservation was detected between the human and the mouse Ik-1 isoforms both at the DNA and the protein levels. The portion of the mouse Ik-1 that contains exons 3 through 7 display 89% and 91% identity to its human homologue at the DNA and protein levels respectively. However the N-terminal portion of the mouse Ik-1 isoform encoded by exons 1/2 was not found in any of the three human cDNAs. The cDNAs instead display distinct 5' ends. The lack of conservation in this part of the human and mouse Ikaros proteins suggest that each of their N-terminal portions are probably not functionally significant. The distinct 5' untranslated sequences present in these human cDNAs are reminiscent of the number of distinct 5' untranslated sequences present in mouse cDNA products of potential alternate promoter usage.

Of the human cDNAs isolated, only one contained the splicing junction between exons-4 and -6 found in the mouse Ik-4 isoform. The lower frequency of cloning of human Ik-4 relative to human Ik-1 cDNAs may reflect their relative concentrations in this T cell line. In the mouse, the Ik-1 isoform is found in excess relative to the Ik-4 isoform in the differentiating T cells (A. Molnar et al 1994).

Human Ikaros isoforms were cloned as follows: A human cDNA library made from the mature T cell line Jurkat (Stratagene) was screened with a 150 bp single stranded probe derived from the most 3' of the IK-1 mouse Ikaros cDNA. From the $8 \times 10^5$ recombinant phages screened, 9 positive clones were obtained. Filters with recombinant phage DNA were incubated overnight in hybridization buffer (7% SDS, 1% BSA, 0.25 Sodium-phosphate pH 6.5 and 0.5 mM EDTA) with $1 \times 10^6$ cpm/ml probe at 65° C. Washes were performed twice in 2×SSC/1% SDS, 0.2×SSC/1% SDS and 0.2×SSC/0 1% SDS at 65° prior to autoradiogarphy. Positive clones were purified and characterized by dideoxy sequencing.

Expression of the Ikaros Gene in Human Tissues and Cell Lines.

Expression of the Ikaros gene was determined in human tissue and cell lines. Two major Ikaros RNA transcripts were detected only in polyA+ RNA from thymus, spleen, and peripheral leukocytes. Very low levels of Ikaros mRNA was also detected in the colon, and probably reflects the resident lymphocyte population in this tissue. The smaller (28S) of the two Ikaros mRNA forms correlates in size with the major Ikaros transcript detected in the mouse, while the larger form correlates in size with a low abundance transcript detected in the mouse upon overexposure of Northern blots. High levels of both of these mRNAs were expressed in the thymus, while the larger form predominated in the spleen. In peripheral leukocytes equal amounts of both transcripts were present, but at 2 fold lower level than in the thymus. These two mRNA species detected in the human may represent products of differential splicing with the larger species containing additional 5' and/or 3' non coding exons. In addition, they may be transcribed from distinct promoters and may be comprised of different combinations of 5' untranslated exons.

Northern Analysis was carried out as follows: Two Northern blots each containing 2 µgs of poly A+ RNA isolated from human heart, brain, placenta, lung, liver, skeletal muscle kidney, and pancreas (Clontech human blot) and from spleen, thymus, prostate, testis, ovary, small intestine, colon, and peripheral blood leukocytes (Clontech human blot II) were hybridized with a probe ($10^6$ cpm /ml in hybridization buffer) made from the 800 bp SacI-EcoRI fragment of hIk-1 cDNA. A northern blot containing 10 µgs of total RNA prepared from the T cell leukemic lines: CEM, Molt-4, from the acute myelogenous leukemia KG1, the acute monocytic leukemia THP-1, the U937 histiocytic lymphoma, 30 µgs of the T cell line HPB 1 and 2.5 µgs of human thymus.

The Ikaros Protein Isoforms are Conserved Between Mouse and Man.

The expression of the Ikaros protein isoforms was examined in human and mouse T cell nuclear extracts by Western blotting. Nuclear extracts from mouse and human fibroblast and epithelial cells were used to determine the specificity of the Ikaros antibody. A number of crossreacting proteins were detected in the nuclear extract from the mouse EL-4 T cell line. Since cDNAs that encode at least five size distinct Ikaros proteins were cloned from this cell line, the proteins detected with the Ikaros antibody are probably Ikaros isoforms expressed in this cell line. In the hu man T cell line Jurkat, the largest of these proteins was the most abundant form but other smaller proteins were detected at lower abundance. These human T cell nuclear proteins may represent the homologues of the mouse Ik-1, Ik-2, Ik-3 and Ik-4 isoforms in order of decreasing relative concentration. No crossreacting proteins were detected in the nuclear extracts from the CV1 and NIH-3T3 non expressing cell lines, thus confirming the specificity of the detecting antibody Western analysis of human and mouse nuclear extracts were carried out as follows: 20 µgs of protein, from nuclear extracts prepared from the Ikaros expressing mouse and human T cell lines EL4 and Jurkat, and from the Ikaros non-expressing mouse and monkey fibroblast and kidney epithelial lines NIH-3T3 and CV1, were run on 12% PAGE. Proteins were transferred to a nitrocellulose membrane and were analyzed with a 1:250 dilution of Ikaros antibody raised to the N-terminal portion of the mouse Ik-2 isoform containing exons 1, 3, 4, 5, and 6. The second step was performed using 1:3000 dilution of goat anti-rabbit antibody (BioRAD) conjugated to alkaline phoshatase. Antibody complexes were detected with BCIP and NBT substrates.

The Ikaros Mouse Genomic Locus

Figure 6:
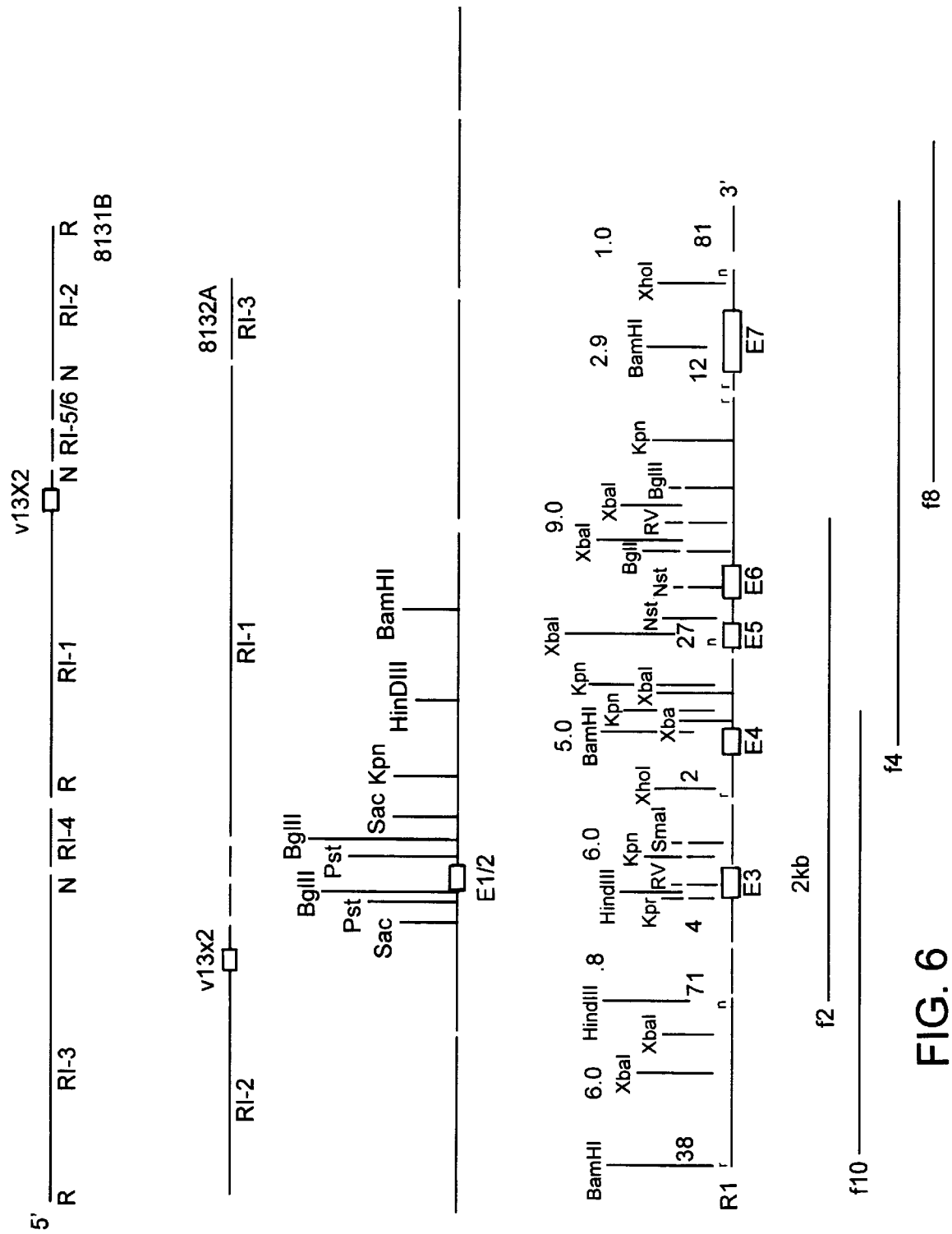
FIG. 6 is a map of the genomic organization of the mouse Ikaros gene. The entire gene is 80–90 kB in length. Intronic or uncharacterized DNA is indicated as a line between 5' and 3'. Exons are indicated as boxes. Lines numbered f2, f10, f4, and f8 indicate phage inserts corresponding to the sequence immediately above. Restriction sites are indicated by the usual abbreviations.

Based on sequence analysis of variant cDNAs, the genomic locus is thought to include about 9–11 exons. Genomic DNAs encompassing most or all of the Ikaros exons present in the genome were isolated by screening a mouse genomic SV129 library made into the λDASH II phage vector using the various Ikaros cDNAs as probes. The Ikaros gene includes at least 80–90 kb of genomic sequence which was isolated as distinct but also overlapping genomic clones. Some of the Ikaros genomic clones are indicated in FIG. 6. The exons are depicted as boxes while the introns as lines. The DNA sequence for: the 5' boundary (SEQ ID NO:8) and the 3' boundary (SEQ ID NO:9) of exon E5; the 5' boundary (SEQ ID NO:10) of exon E3; and the 5' boundary (SEQ ID NO:11) and the 3' boundary (SEQ ID NO:12) of exon E7, were determined.

The Mouse Ikaros Gene is Located at the Proximal Arm of Chromosome 11

The mouse chromosomal location of Ikaros was determined by interspecific backcross analysis using progeny derived from matings of [(C57BL/6J×F1 X C57BL/6J] mice. This interspecific backcross mapping panel has been typed for over 1300 loci that are well distributed among all the autosomes as well as the X chromosome. C57BL/6J and M spretus DNAs were digested with several enzymes and analyzed by Southern blot hybridization for informative restriction fragment length polymorphisms (RFLPs) using a mouse cDNA fragment as a probe. The 6.5 kb M. Spretus PstI restriction-fragment-length polymorphism (RFLP) was used to follow the segregation of the Ikaros locus in backcross mice. The mapping results indicated that Ikaros is located in the proximal region of mouse chromosome 11 linked to Lif, Erbb and Rel. Although 129 mice were analyzed for every marker, up to 157 mice were typed for some pairs of markers. Each locus was analyzed in pairwise combinations for recombination frequencies using the additional data. The ratios of the total number of mice exhibiting recombinant chromosomes to the total number of mice analyzed for each pair of loci and the most likely gene order are: centromere—Lif—6/167—Ikaros—3/146—Erbb—6/158—Rel. The recombination frequencies [expressed as genetic distances in centiMorgans (cM) +/- the standard error] are —Lif—3.6 +/-1.4—Ikaros—2.1 +/-1.2—Erbb—3.8 +/-1.5—Rel.

The interspecific map of chromosome 11 was composed with a composite mouse linkage map that reports the map location of many uncloned mouse mutations (compiled by M. T. Davisson, T. H. Roderick, A. L. Hillyard, and D. P. Doolittle and provided from GBASE, a computerized database maintained at The Jackson Laboratory, Bar Harbor, Me.). Ikaros mapped in a region of the composite map that lacks mouse mutations with a phenotype that might be expected for an alteration in this locus.

The proximal region of mouse chromosome 11 shares a region of homology with human chromosomes 22, 7 and 2. In particular Erbb has been placed on human 7p12. The tight linkage between Erbb and Ikaros in mouse suggests that Ikaros will reside on 7p as well.

Interspecific backcross progeny were generated by mating (C57BL/6J×M. spretus) F1 females and C57BL/6J males as described (Copeland and Jenkins, 1991). *Trends Genet* 7:113–118. A total of 205 F2 mice were used to map the Ikaros locus DNA isolation, restriction enzyme digestion, agarose gel electrophoresis, Southern blot transfer and hybridization were performed essentially as described (Jenkins et al. (1982) *J. Virol.* 43:26–36; and Jenkins et al (1982) *J. Virol.* 42:379–388). All blots were prepared with Zetabind nylon membrane (AMF-Cuno). The probe, a 350 bp mouse cDNA fragment was labeled with [α-$^{32}$P] dCTP using a random prime labeling kit (Amersham); washing was done to a final stringency of 1.0×SSCP, 0.1% SDS, 65° C. A fragment of 8.4 kh was detected in PstI digested C57BL/6J DNA and a fragment of 6.5 kb was detected in PstI digested M. spretus DNA. The presence or absence of the 6.5 kb M. spretus-specific PstI fragment was followed in backcross mice.

A description of the probes and RFLPs for the loci linked to Ikaros including leukemia inhibitory factor (Lif), avian erythroblastosis oncogene B (Erbb) and reticuloendotheliosis oncogene (Rel) has been reported previously (Karl et al. (1993) *Mol Cell Biol* 10:342–301; Karl et al. (1992) *Genetics* 131:103–173; and Karl et al. (1992) *Science* 256:100–102). Recombination distances were calculated using the computer program SPRETUS MADNESS. Gene order was determined by minimizing the number of recombination events required to explain the allele distribution patterns.

The Ikaros Gene Maps Between p11.2–p13 on Human Chromosome 7.

The human chromosome assignment of the Ikaros gene was performed using DNAs prepared from a panel of somatic cell hybrids made between human and rodent. Primers designed after non-conserved sequences at the 3' end of the human cDNAs were used to distinguish between the human and rodent genes. A 375 bp fragment, as predicted from the human Ik-1 cDNA was amplified from human DNA used as a control and from DNA prepared from the cell hybrid 10791 which contains chromosome 7. The identity of the amplified band was confirmed using a probe derived from this region. To fine map the location of the Ikaros gene a panel of somatic cell hybrids which contained parts of chromosome 7 fused to the rodent genome were analyzed. A hybridizing 10 kb BglII genomic fragment was detected with human genomic DNA. A fragment of similar size was readily detected with DNA from the cell lines Ru Rag 4-13 and 1365 Rag12-9. The former cell line contained the proximal arm of chromosome 7 while the latter contained the distal and part of the proximal up to segment p13. DNA from Rag GN6, a cell line that contains the whole distal arm of chromosome 7 and the proximal arm up to segment p11.2, did not hybridize. Another cell line which contained part of the proximal arm of chromosome 7 from p- to the telomere did not hybridize. This mapping restricts the location of the Ikaros gene between p11.2 and p13, placing it proximate to the Erbb gene locus, as predicted from the mouse.

PCR analysis of somatic cell hybrid DNA prepared from human mouse hamster and human-rodent somatic cell hybrids were used for the chromosome assignment of the human Ikaros gene DNAs from the following cell lines were used in PCR reactions h/h human-hamster hybrid h/m: human-mouse hybrid, 1 to 24 respectively 07299-h/h, 1082613-h/h, 10253-h/h, 10115-h/h 10114-h/h, 10629-h/h 10791-h/h, 10156B-h/h, 10611-h/h, 10926B-h/h, 10927A-h/h 10868-h/h, 10898-h/h 10479-h/m 11418-h/m 10567-h/m 10498-h/m 11010-h/h 10449-h/h 10478-h/m 10323-h/m 10888-h/h, 06318B-h/h 06317-h/h 25 human 26 mouse and 27: hamster DNAs were also used in control reactions 100 ngs of these DNAs were used in a PCR reaction together with 150 ngs of primers hIK-1 GGCTGCCACGGCTTC-CGTGATCCT (SEQ ID NO:15) and hIk-2: AGCG-GTCTGGGGAAACATCTAGGA (SEQ ID NO:16) designed after non-conserved sequences at the 3 min. of the human cDNA. Amplification parameters were: 95° C. for 5 min., 80° C. for 10 min. (with addition of 2.5 units of Taq polymerase), followed by 30 cycles at 93° C. for 1 min., 65° C. for 1 min. and 72° C. for 40", with an additional cycle at 93° C. for 5 min., 65° C. for 2 min. and 72° C. for 7 min. The amplified 375 bp product corresponds to the predicted size from the human cDNA. Fragment identity was confirmed by Southern hybridization with a probe derived from this region.

Fine mapping on human chromosome was further obtained by preparing 7 DNAs from a chromosome 7 hybrid panel which was used either in PCR amplification reactions with the primers described above, or in Southern analysis. The human chromosome 7 content of the hybrid cell lines used were 1365 Rag 12-9:7 qter-p13; Rag GN6:7 qter-p11.2; Ru Rag 4-13: 7 cen-pter (Vortkamp et. al. (1991) *Genomics* 11:737–743). For Southern blot analysis, 5 µg of human DNA and 10 µgs of hybrid and mouse DNA digested with BglII were hybridized with a 375 bp fragment contained within the hIk-1 and hIk-2 primers.

Generation of Transgenic Mice: Targeted Deletion of the DNA Binding Domain (Exons 3 and 4) in the Ikaros Gene (Mutation 2) and the Generation of Ikaros +/− and −/− Mutant Mice.

Cloning of the Ikaros gene, recombination constructs and targeting of embryonic stem (ES) cells.

Figures 8A, 9A:
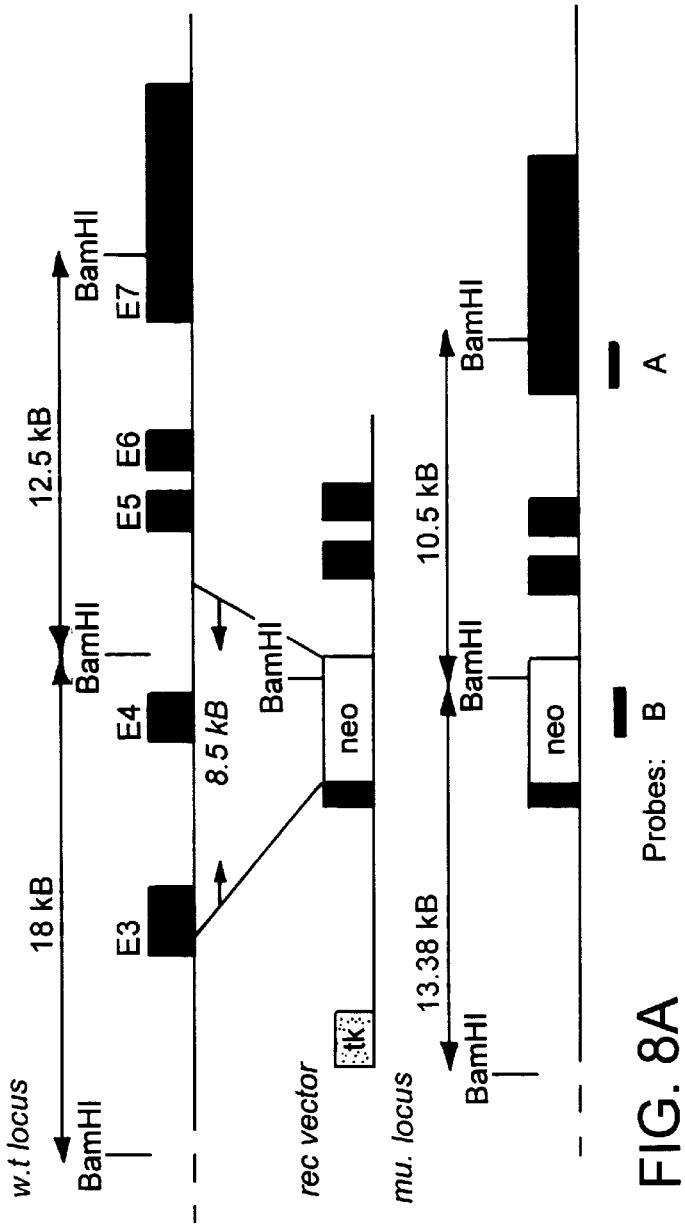
FIG. 8A shows the recombination strategy for targeting a deletion of an 8.5 kB genomic fragment encompassing part of exon 3 and exon 4 of the Ikaros gene.
FIG. 9A is a diagrammatic representation of the exon usage of the Ikaros gene. The zinc fingers modules are shown as perpendicularly stippled boxes. Fingers-1, -2, and -3 encoded by the deleted exons 3 and 4 are responsible for the specific DNA contacts of the Ikaros proteins.

A liver genomic library made from SV129 mouse liver DNA into the phage vector λ DASH II was screened with probes derived from the mouse Ikaros cDNA Ikaros-1 (Molnar, et al., 1994). Overlapping genomic clones were isolated that cover a region of 100 kb containing at least 6 translated exons. The recombination vector described in FIG. 8A was constructed with Ikaros genomic fragments and the neomycin and thymidine kinase expression cassettes (Li, E. et al. (1992) *Cell* 69:915–926) using standard molecular biology protocols. 25 µgs of the recombination vector were electroporated into $1 \times 10^7$ J1 embryonic stem cells maintained on subconfluent embryonic fibroblasts. Transfected ES cells were originally plated on embryonic fibroblasts and grown without selection. 20 hrs later media containing G418 (400 µgs/ml) and 48 hrs G418 and FIAU (0.2 µM Bristol Myers) were added. Cells were fed every two days, colonies were monitored for their undifferentiated morphology and picked between seven and nine days after plating. After DNA analysis, a number of ES cell clones with legitimate recombination events were placed back into culture and the ones which displayed undifferentiated properties were passaged once more before they were injected into a day 3.5 C57BL/6 or Balb/c blastocyst. Chimeric blastocysts were then injected in pseudo-pregnant foster mothers. Chimeric animals were born 18 days later and the ones that were more than 40% agouti were bred against background. Female and male F1 mice with germ line transmission of the Ikaros mutation were bred to homozygocity. The genotype of F1 and F2 mice was determined by Southern and by PCR analysis of tail DNA using either probe A as shown in FIG. 8A or appropriate primers designed from the neomycin (Neo1) and the Ikaros genes (Ex3F and Ex3R). Ex3F:AGT AAT GTT AAA GTA GAG ACT CAG (SEQ ID NO:17); Ex3R:GTA TGA CTT CTT TTG TGA ACC ATG (SEQ ID NO:18); Neo1: CCA GCC TCT GAG CCC AGA AAG CGA (SEQ ID NO:19)

Given the extensive differential splicing of Ikaros transcripts (Molnar, A. et al., (1994)), the multiple transcription initiation sites and the size and complexity of this genomic locus, a recombination vector was designed to replace an 8.5 kb genomic fragment containing part of exon 3 and exon 4 with the neomycin cassette (FIG. 8A). FIG. 8A shows the recombination strategy for targetting a deletion of an 8.5 kB genomic fragment encompassing part of exon 3 and exon 4. Probe A, which was derived from a region outside the recombination locus was used to screen for homologous recombination events. This mutation deletes zinc fingers - 1, -2, and -3, responsible for mediating the sequence specific DNA binding of the Ikaros proteins. This mutation should prevent the Ikaros proteins from binding DNA and activating transcription (Molnar, et al., 1994).

Figure 8B:
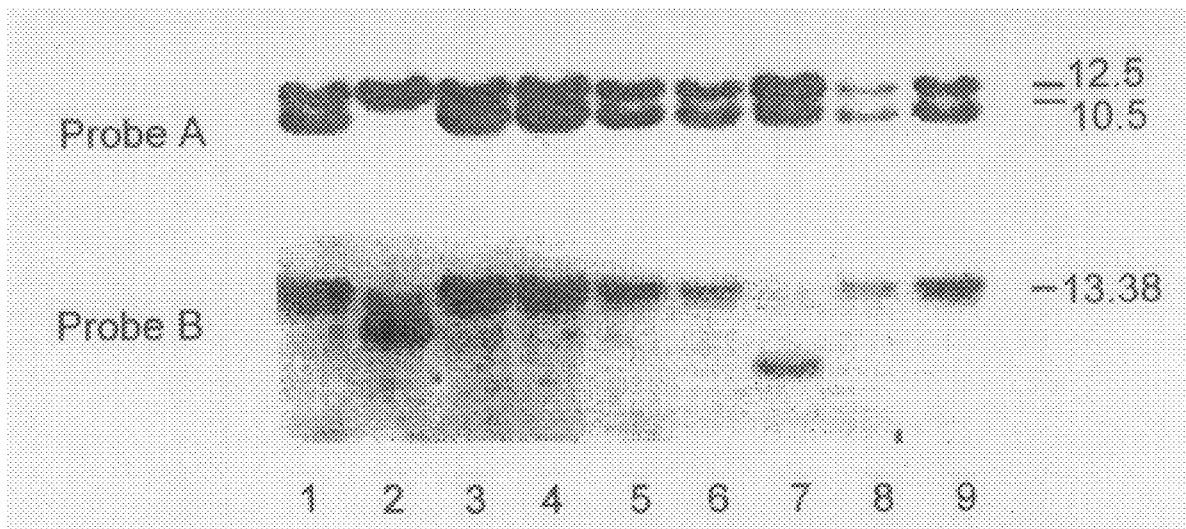
FIG. 8B shows an analysis of genomic DNA from 12 selected embryonic stem cell clones for homologous recombination events.
Figure 8C:
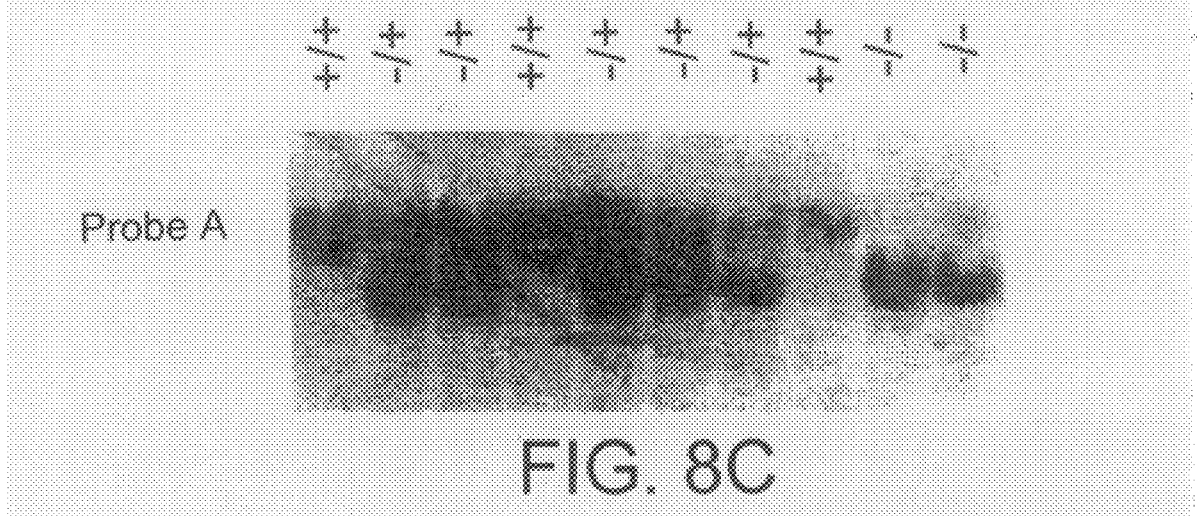
FIG. 8C is a Southern analysis of mouse tail DNA from a 2 week old F2 litter. This analysis revealed the occurrence of homozygous offspring at the expected Mendelian frequency.

This recombination vector was targeted in the embryonic stem (ES) cell line J1 (Li, E. et al. (1992) *Cell* 69:915–926). 300 neomycin and FIAU resistant ES cell colonies were picked and expanded. DNA was prepared and analyzed by Southern blotting using DNA probes from outside the homologous recombination area (FIG. 8B). FIG. 8B shows an analysis of genomic DNA from 12 selected ES cell clones. A 12.5 kB and a 10.5 kB BamHI genomic fragments from the wild type and the targeted Ikaros alleles respectively hybridized to probe A. Single integration events were scored using a probe derived from the neomycin gene (FIG. 8C). The homologous recombination frequency among the ES cell clones analyzed was 1:10. Two ES cell lines with legitimate homologous recombination events and with undifferentiated growth properties were passaged another time and were then injected into day 3.5 blastocysts (FIG. 8B,) ES cells whose DNA analysis is shown in lanes 4 and 9). Two distinct ES cell lines heterozygous for this mutation were used in separate blastocyst injections to rule out phenotypes that result from cell line mutations. To explore potential phenotype variability on different genetic backgrounds the mutant ES cells were injected in blastocysts from C57BL/6 and Balb/c mice. The chimeric blastocysts were reimplanted in pseudo-pregnant mice which gave birth to chimeric animals. Chimeras which were more than 40% agouti (SV129 positive) were bred against their host background. Male and female F1 progeny with germ line transmission were bred against each other. F2 litters were scored for wild type, heterozygous and homozygous pups as shown in FIG. 8C. FIG. 8C is a Southern analysis of tail DNAs from a 2 week old F2 litter which revealed the occurrence of homozygous offspring at the expected Mendelian frequency.
Characterization of Transgenic Mice Heterozygous for the DNA-Binding Defective Transgene Ikaros −/+ transgenic animals develop lymphomas.

Animals heterozygous for the Ikaros mutations develop lymphoproliferations in the thymus, spleen, and lymph nodes. The lymphoid organs become significantly enlarged, the spleen reaches the size of 4.5×1.3×0.6 cm. The thymus can range from moderately enlarged to occupying the whole thoracic cavity and the cervical and auxiliary lymph nodes can reach the size of 1 cm. The penetrance of lymphoproliferation if 100%. Most animals develop this syndrome around 2–3 months and do not survive past the fifth month of age. Microscopic examination of blood smears from these animals revealed large nucleated blast like cells with azurophilic cytoplasm and prominent nucleoli. These large nucleated cells predominate leukocytes in the blood smear of all animals. The leukocyte count in the blood of these animals is often 6 times the number of that in the blood of their wild type litter mates.

The cell populations of the spleen, the thymus, the lymph nodes and the bone marrow in the affected animals were analyzed with antibodies to T, B, myeloid and erythroid differentiation antigens by FACS. The majority of the cells analyzed were positive for Thy 1, CD5, TCR, CD25, CD18 antigens which demarcate mature but also activated T cells. This population was predominant in all four lymphoid tissues suggesting expansion of a T cell in all lymphomas. Cells obtained from these animals can be propagated in tissue culture in the presence of IL-2.

Preliminary cDNA and Northern analysis of these cells revealed three separate splicing events which join exon 2 to exon 5 and exon 7. These mutant mRNAs can generate proteins lacking the DNA binding domain (deleted exons 3 and 4) but containing their C-terminal part, similar or identical to the naturally occurring isoforms IL-5 and IK-6.
Characterization of Transgenic Animals Homozygous for the DNA-Binding Defective Transgene Ikaros −/− Mutant Mice are Born but Fail to Thrive Mice homozygous for the Ikaros mutation 2 were born with the expected Mendelian frequency indicating that the mutation does not affect their survival in utero. At birth homozygous, heterozygous and wild type littermates were indistinguishable. One week past birth, however, homozygous pups were identifiable by their smaller size. This size difference escalates during the third and fourth weeks of their lives. The size of homozygous animals varied from ⅓ to 2t3 of that of their wild type littermates and most of them displayed a matted coat appearance.

No morphological and hemopoietic cell differences were detected between wild type and heterozygous pups. A large majority of t he Ikaros −/− mutant mice (approximately 95%) died between the first and third week of their life. A large proportion of these deaths were associated with cannibalism by the mothers. The mortality rate was higher on the C57BL/6 mixed background where mothers were less tolerant of defective pups. Mutant animals survived better in smaller litters suggesting that competition in a larger litter may escalate the death rate.

Analysis of homozygous mice derived from the two distinct ES cell clones verified that the phenotype observed was due to the mutation in the Ikaros gene. Ikaros −/− mutant mice derived from either ES cell clones were identical in terms of their growth, survival, hemopoietic populations and disease contraction. Animals were studied from several days to 12 weeks past birth on the SV129×Balbc, SV129×C57 and SV129 backgrounds. Normal looking and severely growth retarded mutant mice were examined. Their hemopoietic system was extensively studied. Finally their inability to thrive and cause of death was investigated. The overall hemopoietic phenotype and disease contraction in homozygous animals described in the following sections was the same on all three genetic backgrounds. The small number of mutant mice that survived for more than one month is exclusively on the Sv129×Balb/c background but its hemopoietic populations were not any different from the majority of homozygous animals analyzed.

Ikaros −/− Mutant Mice have a Rudimentary Thymus with no Definitive T Cell Progenitors Gross anatomical examination of the thoracic cavity in Ikaros −/− mutant mice at 2–3 weeks of age failed to identify a thymic gland. However, upon careful microscopic inspection, a rudimentary organ was observed. The thymic rudiment was often found in adipose tissue and sometimes was located at a higher position in the thoracic cavity than the thymus in normal, age matched animals. The location and the often non-fused bilobed appearance of this thymus resemble those of the early embryonic organ. This mutant thymus contained approximately $1 \times 10^5$ cells in contrast to the $1$–$2 \times 10^8$ cells regularly obtained from wild type littermates. This thymic rudiment was difficult to identify in one week old mutant mice but it was easier to detect after the third postnatal week. The density of nucleated cells in the mutant thymus was low when compared to the cellularity of the normal thymus. Eosinophils detected in the wild type thymus were also seen in the mutant organ especially around the portal arteries.

Thymic rudiments from Ikaros −/− littermates (two to four mice depending on litter availability) were pooled and analyzed by fluorescent antibody staining and flow cytometry. Forward and side scatter analysis of the Ikaros −/− thymocytes revealed a smaller size population compared to wild type controls. The cell composition of the thymus in Ikaros mutant mice ($1 \times 10^5$ cells recovered per thymus) and wild type littermates ($2 \times 10^8$ cells recovered per thymus) was determined. Cells were double-stained with: anti-CD4$^{PE}$/anti-CD8$^{FITC}$, anti-CD3$^{PE}$/anti-TCRαβ$^{FITC}$, anti-Thy 1.2$^{PE}$/anti-CD25$^{FITC}$, anti-CD4$^{PE}$/anti-HSA$^{FITC}$. Forward and side scatter analysis was performed on Ikaros −/− and wild type thymocytes to estimate the size and complexity of this population. Combinations of antibodies specific for Thy-1/CD25, CD4/CD8, CD3/TCRαβ, and CD4/HSA antigens were used to stain the Ikaros −/− and wild type thymocytes. These combinations of antigens demarcate the earliest and the later stages in T cell development (reviewed by Godfrey, D. I. and Zlotnik, A. (1993) *Immunology Today*; von Boehmer, 1993 #88; Weisman 1993). The wild type thymus contained the normal complement of mature and immature thymocytes. In sharp contrast, 95% of the mutant organs were devoid of single or double positive CD4 or CD8 cells and lacked cells that stained positively for CD3, TCRαβ, Thy-1 or CD25 (IL-2 receptor) (data is from two week old animals). The majority of these thymic cells stained positive with HSA known to be expressed on 95% of hemopoietic cells apart from early T and B cells Interestingly, a small CD4$^{1o}$/HSA+ subpopulation was detected in some cases. The HSA+ cells detected in the Ikaros -/- thymus may belong to other hemopoietic lineages. Alternatively these cells may represent the earliest T cell progenitors, closely related or perhaps identical to the HSC, which lack expression of any definitive T cell markers. These putative T cell precursors may be arrested at the entry point into the T lymphocyte pathway.

Ikaros -/- Mutant Mice Lack Peripheral Lymphoid Centers.

Inguinal, cervical, axillary and mesenteric lymph nodes were absent by both visual and microscopic examination. Lymph nodes were absent in all of the Ikaros mutant mice examined but were readily detected in all of the wild type littermates. Peyer's patches and lymphocyte follicles were also absent from the gastrointestinal tract of the Ikaros -/- mutant mice but were present in the wild type intestines and colon.

Dendritic Epidermal T Cells are Absent in Ikaros -/- Mice

Epidermal sheets from ear skin from Ikaros -/- and wild type mice were examined for γδ T cells and for Langerhan cells. Ammonium thiocyanate-separated epidermal sheets were stained for immunofluorescence microscopy with fluorescein (FITC) conjugated monoclonal antibodies specific for γδ T cell receptors (mAb GL3) or unconjugated monoclonal antibodies specific for Class II molecules followed by FITC conjugated goat anti-mouse antibody as described in Bigby, M. et al. ((1987) *J. Invest. Dermatol.* 89:495–499), and Juhlin, L. and Shelly, W. B. ((1977) *Acta Dermatovener* (Stockholm) 57:289–296)). Isotype control antibodies were used as negative controls for GL3 and M5/114. Positively stained dendritic cells were identified by epifluorescence microscopy. Ears from three mice of each type were examined. γδ T cells were absent from epidermal sheets from Ikaros -/- mutant mice but were readily detectable in epidermal sheets from wild type mice. Staining with the Class II antibody revealed the presence of dendritic epidermal Langerhan cells in both mutant and wild type epidermis.

Hemopoietic Populations in the Bone Marrow of Ikaros -/- Mice

Hemopoietic populations in the bone marrow of the Ikaros -/- mice were analyzed by flow cytometry using antibodies to lineage specific differentiation antigens. Cells from the bone marrow of Ikaros mutant mice (3–10×10$^7$ cells per animal) and wild type littermates (4–10×10$^7$ cells per animal) were analyzed with the following combinations of mAbs: CD3$^{PE}$/Thy1.2$^{FITC}$, Thy1.2$^{PE}$/Sca-1$^{FITC}$, CD3$^{PE}$/TCRαβ$^{FITC}$, CD45R$^{PE}$/IgM$^{FITC}$, CD45R$^{PE}$/CD43$^{FITC}$, Mac-1$^{PE}$/Gr-1$^{FITC}$, Ter 119$^{PE}$/CD61$^{FITC}$.

Ikaros -/- mice were analyzed and compared to age matched wild type controls. At least six groups of animals were studied on each mixed background (SV129×C57BL/6 and on SV129×Balb/c) and one on Sv129. Each group consisted of pooled organs from one to four littermates at 2 to 3 weeks of age. Older animals (1 month +) were examined individually. Red blood cells in the spleen and bone marrow were lysed by ammonium chloride. Single cell suspensions of thymus, spleen or bone marrow cells were prepared and washed twice in staining wash (PBS with 0.1% BSA), incubated for 20 minutes on ice with a 1:20 dilution of normal rat serum and 1 µg mAb 2.4G2 (PharMingen, San Diego, Calif.) per 1×106 cells to block Fc receptors. Cells (1×10$^6$) were incubated with PE conjugated mAb and FITC conjugated mAb for 40 minutes. 2×10$^4$ thymocytes were stained with appropriate combinations of PE and FITC conjugated mAbs since few cells were recovered from mutant thymus. Cells were then washed 3 times and one- and two-color flow cytometric analyses were performed on a FACScan (Becton-Dickinson, San Jose, Calif.). Gating for viable cells was performed using propidium iodide exclusion and SSC and FSC as described (Yokoyama, W. M. et al. (1993) "Flow Cytometry Analysis Using the Becton Dickinson FACScan. In Current Protocols in Immunology, Coligan, J. E. et al., eds. (Greene Publishing Associates, N.Y.) 5.4.1–5.4.14. Isotype matched control antibodies were used as negative controls. Ten-thousand cells were analyzed for each sample.

The first stages of B cell development take place in the late mid-gestation liver and spleen in the embryo, and in the bone marrow in the adult (Li, Y.-S. et al. (1993) *J. Exp. Med.* 178:951–960). These stages are demarcated by the sequential activation of cell surface antigens. Combinations and levels of expression of these stage specific markers are used to define the pro-B to pre-B stage (CD45R+/CD43+) and the pre-B to the B cell transitions (CD45R+/sIgM+) (Ehlich, A. et al. (1993) *Cell* 72:695–704; Hardy, R. R. et al. (1991) *J. Exp. Med.* 173:1213–1225; Li, Y.-S. et al. (1993) *J. Exp. Med.* 178:951–960; Rolink, A. and Melchers, R. (1991) *Cell* 66:1081–1094). In wild type bone marrow, the CD45R+ population contains B lymphocytes at various stages of their maturation. The small CD45R+/sIgM+ population consists of mature B cells while the even smaller population of CD45R$^{1o}$/CD43R$^{1o}$ cells contains immature lymphocytes at the pro-B cell stage (data shown is from a group of two week old animals).

The rest of the CD45R+ population consists of pre-B cells with rearrranged heavy but not light chains as well as other hemopoietic cells. The CD45R+ population was greatly reduced and in many cases absent in the Ikaros mutant mice. The CD45R+ cells detected were low expressors and were negative for either CD43 or IgM. These cells may derive from an even earlier stage in B cell development than the one defined by the CD45R+/CD43+ combination. Alternatively they may belong to the CD5 lineage of B cells or to another hemopoietic lineage (Hardy, R. R. et al. (1986) *J. Exp. Med.* 173:1213–1225 and Herzenberg, et al., 1986).

T cell progenitors originate in the bone marrow in the adult and in the fetal liver in the embryo but the first definitive steps in T cell differentiation occur after their migration to the thymus. Given the lack of substantial numbers of defined T cell progenitors in the thymic rudiment of the Ikaros -/- mice, we examined their presence in the bone marrow. In most Ikaros -/- mice, a small population of Thy-1 $1^o$ positive cells was present. These cells were not positive for CD3, Sca-1 or CD4 antigens which are expressed on early but definitive T cell precursors. This population of Thy-1 lo cells in the bone marrow of Ikaros -/- mice may contain the earliest lymphocyte progenitors including T and B cell precursors that are arrested in development and therefore unable to home to the thymus or proceed to the next stages differentiation.

The majority of nucleated cells in the bone marrow of Ikaros -/- mice were of the erythroid lineage. The proportion of erythrocyte precursors was larger in the Ikaros mutant mice than in wild type controls (53 vs. 31%). At two weeks of age, a similar number of bone marrow cells were positive for the myeloid lineage marker Mac-1 in the Ikaros −/− mice and in their wild type littermates (19 vs 23% Mac-1+) which suggested that their myeloid compartment was also intact. However, in most cases the Mac-1+/Gr-1+ subpopulation that correlates with polymorphonuclear cells of a more mature granulocytic phenotype was not present among these Mac-1+ cells in most of the Ikaros mutant mice (Hestdal et al., 1991; Fleming et al., 1993, Lagasse and Weissman, 1993). Nevertheless, special stains and histological examination on blood smears and infected tissue has identified numerous circulating and infiltrating cells with mature polymorphonuclear and granulocytic morphology.

The Spleens of the Ikaros −/− Mutant Mice are Enlarged and Heavily Populated with Cells of Erythroid and Myeloid Origin Tissues harvested from euthanized wild type and Ikaros mutant mice were fixed in 4% buffered formalin for 1–2 days. They were then processed and embedded in paraffin. Sections were cut at 5 micron thicknesses, mounted and stained with hematoxylin and eosin or with modified gram stains. Light microscopy was performed at 20–600× magnification on an Olympus BMax-50 microscope. The spleens from the Ikaros −/− mice were enlarged compared to the wild type littermates. This size difference varied from one and a half to three times the size of the wild type spleen. The enlarged size of the Ikaros −/− spleens was in contrast to the absence of peripheral lymphatic centers and to the diminished size of the thymus detected in these mutant animals. The red and white pulp architecture of the wild type spleen was absent in the mutant organ. The white areas detected in mutant spleen were heavily populated with cells of myeloid morphology (m) and were surrounded by red areas populated by erythrocyte (e) precursors. A large number of megakaryocytes were also detected throughout these splenic sections The splenic populations in the Ikaros −/− mice were examined by flow cytometry to delineate the relative representation of the hemopoietic lineages. Single CD4+ and CD8+ cells which together comprise approximately 40% of spleen cells in normal mice were absent in all of the Ikaros −/− mice examined. $\alpha\beta$ and $\gamma\delta$ T cell receptor expressing cells were similarly absent from the Ikaros −/− spleens. flowever, a small but distinct population of Thy-1$^{lo}$ cells which were CD3- and Sca-1 was present as in the bone marrow.

The CD45R+/IgM+ population that represent the transition from the pre-B to the B cell stage in normal spleen were absent from this mutant organ. The CD45R+/CD43+ population that represent the pro-B to pre-B cell transition in the wild type bone marrow were not detected in either wild type or Ikaros −/− spleens.

The majority of the spleen cells in the Ikaros −/− mice were erythrocyte progenitors (TER119+). This population which ranged from 70% at 1–2 weeks of age to 25% in older mutant mice, never exceeded 20% in the spleen of wild type controls. Myeloid cells comprised the second predominant population in the spleen of Ikaros mutant mice and ranged from 9% in young animals to 60% in older mice. In the spleen of wild type mice, myeloid cells never exceeded 5%. In the Ikaros mutant spleen, the erythroid and myeloid lineages together accounted for the majority of the cells (80–100%). In contrast, in the wild type spleen these two lineages represent less than 20% of the total cell population which is accounted for by mature T and B cells.

The presence of myeloid progenitors in the spleen of Ikaros mutant mice was tested in a soft agar clonogenic assay. A large number of mixed macrophage and granulocyte (GM) colonies were established when spleen cells from two week old mutant mice were grown on soft agar in the presence of GM-CSF (Table I). Spleen cells from wild type littermates gave only a small number of mixed GM colonies. Similar numbers of mixed GM colonies were derived from cells from the spleen and bone marrow of mutant mice whereas in wild type animals bone marrow and spleen derived GM colonies differed approximately by ten fold (Table I).

TABLE I

G/M progenitors in the spleen and bone marrow of Ikaros −/− mice

| Experiment 1 | | | | Experiment 2 | | | |
|---|---|---|---|---|---|---|---|
| Spleen | | Bone marrow | | Spleen | | Bone marrow | |
| +/+ | −/− | +/+ | −/− | +/+ | −/− | +/+ | −/− |
| 3 | 38 | 38 | 55 | 8 | 85 | 58 | 100 |

Natural Killer Cell Activity was Absent from the Spleens of Ikaros −/− Mice

NK cells were not appear not to be present in the spleen of the Ikaros −/− mice (as detected by flow cytometry). A small population of these cells was present in wild type spleens (2–5% determined on the SV129×C57BL/6 background). Given the relatively small numbers of splenic NK cells, a functional assay was used to conclusively address their existence. Serial dilutions of spleen cells from Ikaros mutant and wild type animals were grown in the presence of 500 units/ml of IL-2 for 48 hours. These conditions are known to generate activated NK cells which can readily lyse their targets (Garni-Wagner, B. A. et al. (1990) *J. Immunol.* 144:796–803). After two days in culture, spleen cells from wild type control mice effectively lysed chromium labeled NK cell targets (Yac-1) over a wide range of effector to target cell ratios (Table II). However, spleen cells from the Ikaros −/− mice were unable to lyse NK targets even at the highest effector to target cell ratio (60:1)(Table II).

TABLE II

NATURAL KILLER CELL ACTIVITY[a]

| | Percent Lysis[b] | | | |
|---|---|---|---|---|
| Effector to | Experiment 1 | | Experiment 2 | |
| Target Ratio | +/+ | −/− | +/+ | −/− |
| 60:1 | 59 | 1 | ND | ND |
| 30:1 | 48 | 2 | 75 | 4 |
| 15:1 | 43 | 4 | 57 | 10 |
| 7.5:1 | 16 | 4 | 29 | 2 | a. Spleen cells from wild type (+/+) or Ikaros deletion (−/−) mice were cultured in complete RPMI containing 500 units/ml recombinant IL-2 for 72 hours and were then cultured in triplicate with 3000 CR$^{51}$ labeled Yac-1 cells in indicated ratios in a standard 4 hour chromium release assay.

$^b$Percent lysis = $\frac{[\text{CPM} - \text{Spontaneously released CPM}] \times 100}{[\text{Total lysis CPM} - \text{Spontaneously released CPM}]}$ Analysis of Ikaros Mutant mRNAs and Proteins.

The production of Ikaros mRNAs in the spleen of Ikaros mutant mice was investigated using a reverse transcription PCR amplification assay (RT-PCR). Georgopolous, K. et al. (1992) *Science* 258:808. Primers derived from the Ikaros exons within and outside the targeted deletion were used to amplify cDNAs prepared from Ikaros −/− spleen (FIG. 8A).

Figure 9B:
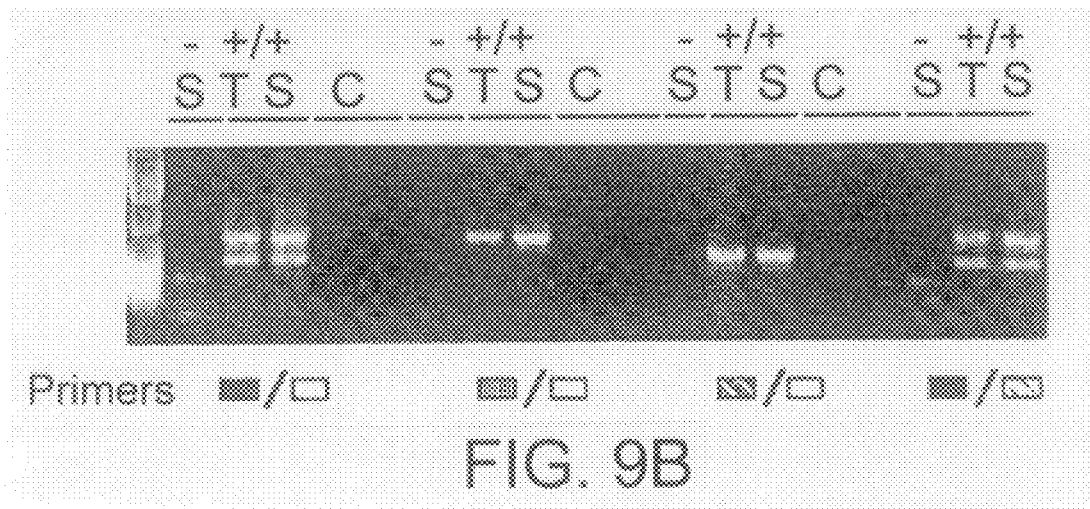
FIG. 9B shows amplification products from wild type (+/+) thymus (T) or wild type and mutant (−/−) spleens (S). cDNAs from wild type thymus or wild type and mutant spleens were PCR amplified with sets of primers that delineate their exon composition (primer sets are shown as filled boxes). These sets of primers amplified from wild type thymus and spleen predominantly products of the IK-1 and IK-2 transcripts. The major amplification product from the Ikaros mutant spleen cDNAs did not contain exon 3 and exon 4 but consisted of exons 1-2-4-5-6-7.
Figure 9C:
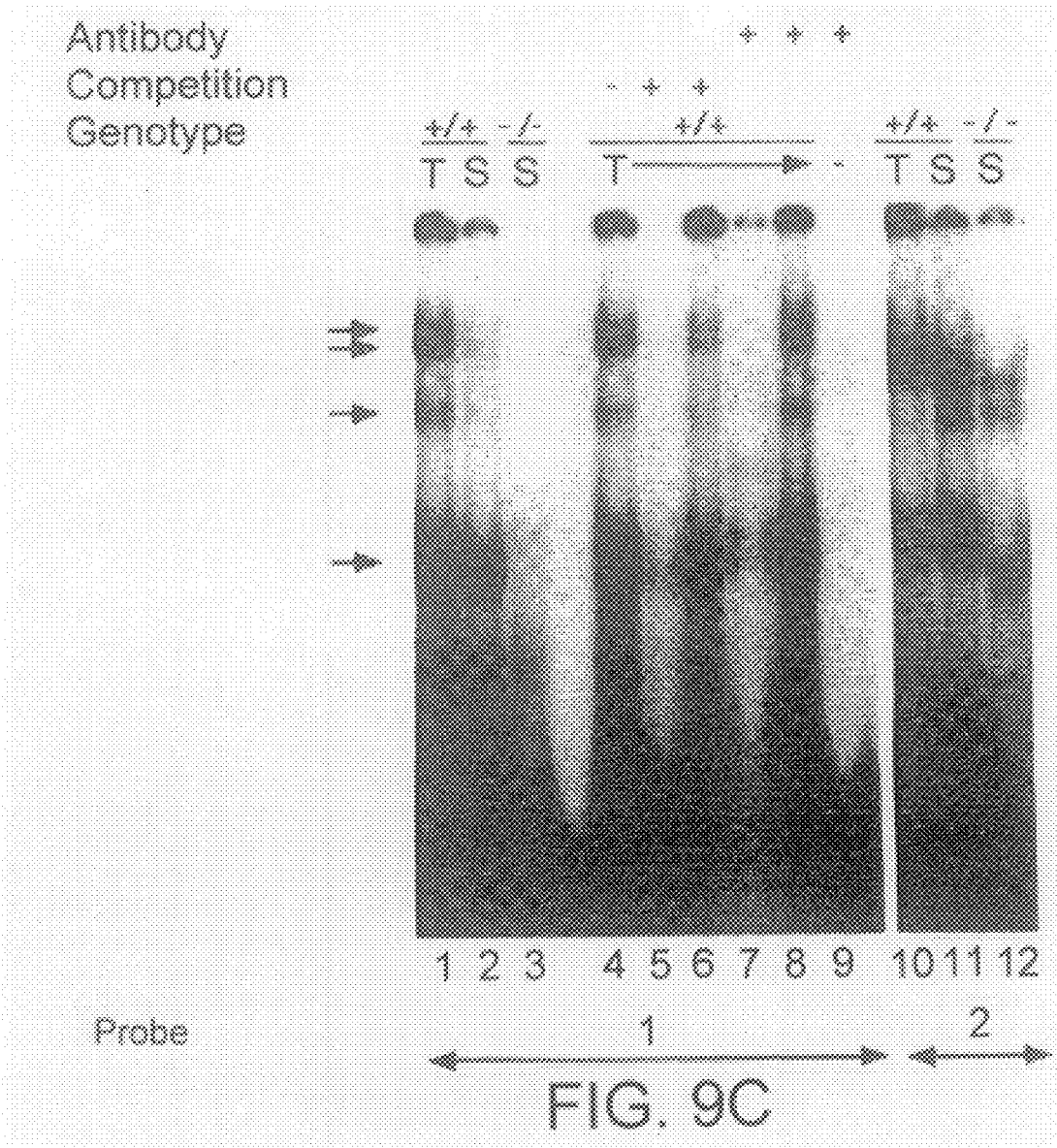
FIG. 9C shows the results of DNA competition assays in which the presence of Ikaros related DNA binding complexes were examined in nuclear extracts prepared from wild type thymus and from wild type and mutant spleen. Four sequence specific DNA binding complexes were established (lanes 4–6). The presence of Ikaros proteins in these nuclear complexes was established by Ikaros specific (lane 7) and non-specific antibodies (lane 8). These complexes are absent altogether from mutant spleen nuclear extracts which however support the formation of DNA binding complexes over an AP-1 site.

These primers, Ex2F/Ex7R, Ex2F/Ex6R, Ex3F/Ex7R, Ex4F/Ex7R, allow the determination of exon usage by the Ikaros transcripts. Ex2F: CAC TAC CTC TGG AGC ACA GCA GAA (SEQ ID NO:20); Ex3F:AGT AAT GTT AAA GTA GAG ACT CAG (SEQ ID NO:17); Ex4F: GGT GAA CGG CCT TTC CAG TGC (SEQ ID NO:21); Ex6R: TCT GAG GCA TAG AGC TCT TAC (SEQ ID NO:22); Ex7R: CAT AGG GCA TGT CTG ACA GGC ACT (SEQ ID NO:23). FIGS. 9A, 9B, and 9C are diagramatic representations of the exon usage in the Ikaros gene. The zinc finger modules are shown as perpendicularly stippled boxes. Fingers -1, -2 and -3 encoded by the deleted exons 3 and 4 are responsible for the specific DNA contacts of the Ikaros proteins (Molnar et al., 1994a). FIG. 9B shows cDNAs from wild type (+/+) thymus (T) or wild type and mutant (−/−) spleens (S) were PCR amplified with sets of primers that delineate their exon composition (primer sites are shown as filled boxes). These sets of primers amplified from wild type thymus and spleen predominantly products of the Ik-1 and Ik-2 transcripts as previously described (Molnar et al., 1994a). The major amplification product from the Ikaros mutant spleen cDNAs did not contain exon 3 and exon 4 but consisted of exons 1-2-5-6-7. In FIG. 9C, the presence of Ikaros related DNA binding complexes were examined in nuclear extracts prepared from wild type thymus and from wild type and mutant spleen. Four sequence specific DNA binding complexes (arrows) were established by DNA competition assays (lanes 4–6). The presence of Ikaros proteins in these nuclear complexes was established by Ikaros specific (lane 7) and non-specific antibodies (lane 8). These complexes are absent altogether from mutant spleen nuclear extracts which however support the formation of DNA binding complexes over an AP-1 site.

Analysis of these amplified products revealed the production of Ikaros mRNAs. These Ikaros mRNAs lack exons 3 and 4 and the major species corresponds in size to a transcript comprised of exons 1-2-5-6-7 (FIG. 9A). Proteins encoded by these Ikaros mRNAs lack the DNA binding zinc fingers -1, -2 and -3 encoded by exons 3 and 4 (Molnar, et al., 1994).

The absence of Ikaros related DNA binding complexes in the hemopoietic populations of Ikaros mutant mice was confirmed in a gel retardation assay. Nuclear extracts were prepared and gel retardation assays were carried out as previously described. Georgopoulos, K. et al. (1992) *Science* 258:808. 2 μgs of nuclear extract were incubated with end labeled oligonucleotides containing either a high affinity Ikaros (IKBS4) or an AP-1 binding site. IK-BS4: TCAGCTTTTGGGAATGTATTCCCTGTCA (SEQ ID NO:24); IK-BS5: TCAGCTTTTGAGAATACCCTGTCA (SEQ ID NO:25); AP1: GGC ATG ACT CAG AGC GA (SEQ ID NO:26).

Nuclear extracts prepared from two week old wild type thymus and wild type and mutant spleens were tested for binding to a high affinity recognition sequence for the Ikaros proteins (Molnar, et al., 1994). Four DNA binding complexes with distinct mobilities were detected when nuclear proteins from wild type thymus and spleen were used (FIG. 9B, lane 1 and 2). However, none of these four DNA binding complexes was formed when splenic nuclear extracts made from Ikaros mutant mice were used. Nevertheless, these nuclear extracts supported the formation of DNA binding complexes over an AP1 binding site (FIG. 9B, lanes 10–12). Competitor DNA with a high affinity recognition site for the Ikaros proteins abrogated binding of all four complexes while DNA with a mutation in the binding consensus for the Ikaros proteins had no effect (FIG. 9B, lanes 4–6 and Molnar, et al., 1994). Pretreatment of the thymic nuclear extract with Ikaros antibodies also abrogated all four of these DNA binding complexes whereas an unrelated antibody showed no effect. These data indicate that nuclear complexes which contain Ikaros proteins are present in cell populations in the thymus and spleen of wild type animals but are absent in the spleen cells of the homozygous mutants (FIG. 9B, lanes 7–9).

Opportunistic Infections and Death in Ikaros −/− Mice

Deaths of Ikaros −/− mice occurred as early as the end of their first postnatal week. The mortality rate increased during the second and the third weeks of life. Approximately 95% of the mice died within 4 weeks. Gross and histopathological examination of the mouse gastrointestinal tract, liver, lung and blood was performed to evaluate the cause of their death.

Examination of the intestines did not reveal major histopathological abnormalities, however, Ikaros −/− mice consistently had numerous and diverse bacterial microorganisms in their intestinal tract. Large numbers of gram negative and positive rods and cocci were detected on tissue gram stains of intestinal sections from the mutant mice. Although a small number of bacteria were observed in wild type intestinal epithelia, their number and diversity did not compare to that detected in mutant mice. Cultures from gastrointestinal epithelia from Ikaros −/− mice identified a number of proliferating microorganisms. Interestingly, anaerobic endospore-forming bacteria of the Oscillospira caryophanon group were found at a highly prolific state in the intestines of the Ikaros mutant mice while they were not detected in wild type controls.

The liver in almost all animals examined contained focal infarcts that appeared as pale or white nodules. In extreme cases, half of the liver had undergone necrosis. Necrotic areas and accumulation of large numbers of monocytes, macrophages and eosinophils were present on hematoxylin and eosin stained liver sections. Hematoxylin and eosin staining of lung tissue from one month old mutant animal revealed the destruction of normal tissue structure, bacterial abcsessae and myeloid infiltration. This staining exhibited necrotic areas and bacterial growth mainly at the subcupsullary region and extensive infiltration with myelocytes and eosinophils. Cultures from the liver grew pasturella pneumonotropica and enterobacteria species, microorganisms which comprise part of the microbial flora in the oral and gastrointestinal cavities of normal mice. Cultures from wild type liver had no growth. In a Wright stain of blood smears from a one month old Ikaros mutant mouse, basophils were the prevalent leucocyte population detected and were found concentrated over clusters of bacteria. The bacteria identified on Wright stained blood smears indicated high grade septicemia (Fife, A. et al. (1994) *J. Clin. Pathol.* 47:82–84). Blood clots were cultured and frequently contained multiple strains of microorganisms.

Ikaros and Hematopoietic Development

The analysis of mice with a mutation in the Ikaros gene provides convincing evidence that the Ikaros gene plays a pivotal role in lymphocyte specification. An intact Ikaros gene is essential for the development of T and B lymphocytes and NK cells. The Ikaros gene is not essential for the production of totipotential hemopoietic stem cells, erythrocytes, myelocytes, monocytes, dendritic cells, megakaryocytes and platelets.

As shown above, a mutation in the Ikaros gene that abolishes the DNA binding domain in at least four of its protein products has profound effects on T lymphocyte development. T cell differentiation is arrested at a very early stage. Ikaros −/− mutant mice have a rudimentary thymus which contains 1×10$^5$ cells, 2000 times less than the wild type organ. These cells are HSA+ with a small subpopulation approximately 10% expressing low levels of HSA and CD4. No other definitive early T cell marker, e.g., Thy-1, Sca-1, CD25, CD3 was expressed on these cells. The majority of these HSA+ cells in the Ikaros −/− thymus may belong to other hemopoietic lineages. Alternatively, they may contain small non cycling T cell progenitors arrested at a very early stage of intrathymic differentiation. The Thy-1+CD3$^-$SCA-1$^-$ cells detected in the bone marrow and spleen of the Ikaros mutant mice may also contain arrested T cell progenitors which may lack expression of the appropriate surface receptors that enable them to home to the thymus.

Lymphocyte progenitors that give rise mainly to the γδ T lineage populate the thymus from day 14 through day 17 of fetal development (Havran, W. L. and Allison, J. P. (1988) *Nature* 344:68–70; Ikuta, K. et al. (1992) *Annu. Rev. Immunol.* 10:759–783; Raulet, D. H. et al. (1991) *Immunol. Rev.* 120:185–204). Mature γδ T cells produced during this time populate the skin and vaginal epithelium and provide the life long supply of dendritic epiderrnal T cells (Asnarnow, D. M. et al. (1988) *Cell* need volume: 837–847; Havran and Allison, 1990; Havran, W. L. et al. (1989) *Proc. Natl. Acad. Sci. USA* 86:4185–4189). The absence of γδ T cells in Ikaros −/− mice implies that this stage in T cell ontogeny is never reached in these animals.

The Ikaros mutation has profound effects on the development of a third lineage of T cells, that of NK cells. Since these cytotoxic cells share differentiation antigens with T cells it has been proposed that they may be derived from a common progenitor (Rodewald, H. et al. (1992) *Cell* 139–150). Differentiation experiments with committed T cell progenitors have failed to generate the expected NK cell activity (Garni-Wagner, B. A. et al. (1990) *J. Immunol.* 144:796–803). Nevertheless, a common bipotential progenitor may exist which may not have a definitive T cell phenotype definable by early T cell differentiation antigens e.g. HSA, pgpl, CD4 and CD25. This progenitor pool may be part of the cell population detected in the Ikaros mutant thymus.

Many immunodeficient animals which do not produce mature lymphocytes appear to live well under relatively germ free conditions. This fact has been partly a attributed to the high numbers of circulating NK cells in these animals (Mombaerts, P. et al. (1992) *Cell* 68:869–877; Shinkai, Y. et al. (1992) *Cell* 68:855–867; Spanopoulou, E. et al. (1994) *Genes Dev.*). In contrast, Ikaros mutant mice fail to thrive even in relatively germ free conditions. A majority of these animals die soon after birth. Septicemia is the major cause of death in these animals. The rapid development of bacterial infections in Ikaros −/− animals may be due to the lack of NK cells in addition to lack of T and B lymphocytes.

No mature B cells or any of their well defined progenitors were found in the bone marrow or the spleen of the Ikaros mutant mice. A small population of CD45R$^{1o}$ cells was detected which did not express CD43 or IgM, surface markers characteristic of the pro-B and pre-B cell transition. This total lack of T and B cell progenitors is unprecedented among naturally occurring and genetically engineered immunodeficient mice (Karasuyama, et al.,need citation; Mombaerts, P. et al. (1992) *Cell* 68:869–877; Shinkai, Y. et al. (1992) *Cell* 68:855–867) suggesting that Ikaros mutant mice may be arrested at the hemopoietic stem cell level before lymphocyte specification. The described functional disruption of the Ikaros gene may affect the development of a progenitor stem cell that gives rise to T, B and the NK cell lineages. However, the Ikaros gene products may control the development of three distinct progenitors each responsible for giving rise to a distinct lymphocyte lineage with each lineage arrested at the very first steps of its ontogeny.

Profound effects from this Ikaros mutation were also seen on the population dynamics of the erythroid and myeloid lineages. The relative proportion of erythroid and myeloid progenitors were increased in the bone marrow and especially in the spleen of Ikaros mutant mice compared to their wild type littermates. However, the absolute number of hemopoietic cells was lower in the bone marrow but higher in the spleen of mutant mice. These observations were in contrast to other immunodeficient mice where lack of mature T and B lymphocytes dramatically decreased the number of hemopoietic cells in the spleen but had smaller effects on bone marrow populations. These results may have several explanations.

Figure 10:
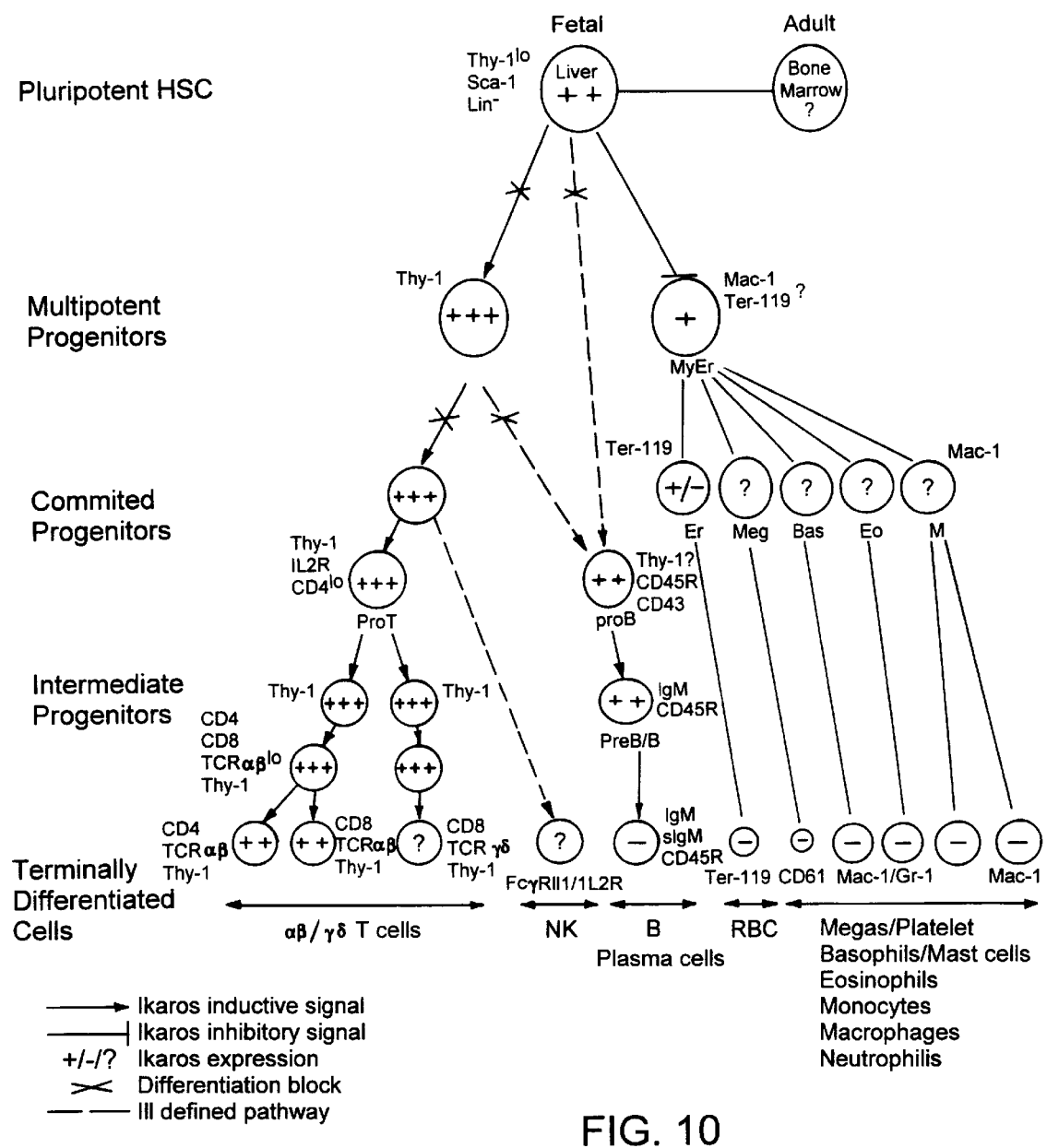
FIG. 10 is a schematic of an Ikaros view of the hemopoietic system which shows Ikaros expression and its putative roles in differentiation

One possibility is that one of the functions of the Ikaros gene products, potentially expressed in the pluripotential hemopoietic stem cell (HSC), is to signal its differentiation into the lymphocyte lineage (FIG. 10). FIG. 10 shows an Ikaros view of the hemopoietic system; expression and putative roles in differentiation. Ikaros expression at the various stages of hemopoietic development is an approximation (Georgopoulos, K. et al. (1992) *Science* 258:808). Expression data was derived from Northern and PCR analysis of primary cells and cell lines and by in situ hybridization of fetal hemopoictic centers. Relative levels of expression (+) or lack of (−) are shown at various stages in development. Potential inductive signals for lymphocyte commitment and differentiation provided by the Ikaros gene are shown as arrows. Interrupted lines indicate putative Ikaros related negative signals for differentiation in the erythroid and myeloid lineages. Transitions in the lymphocyte pathway during which development is probably aborted in Ikaros −/− mice are drawn as Xs on the pathway. Dashed lines indicate unsettled transitions in lymphocyte differentiation, e.g. the existence of a common committed progenitor for the T and B lineages or their independent derivation from the pluripotent hemopoietic stem cell is a controversial issue (Ikuta, K. et al. (1992) *Annu. Rev. Immunol.* 10:759–783). In addition the origin of the T and NK lineages from a common committed T cell progenitor remains under debate (Hackett, J. J. et al. (1986) *Proc. Natl. Acad. Sci. USA* 83:3427–3431; Hackett, J. J. et al. (1986) *J. Immunol.* 136:3124–3131.; Rodewald, H. et al. (1992) *Cell* 139:150). Differentiation antigens representative of the various stages of hemopoietic and lymphocyte development (also used in the analysis of the Ikaros −/− mice) are shown. In the absence of these lymphocyte specific differentiation signals provided by the Ikaros gene products, the HSC is diverted by default into one of the other hemopoietic pathways.

The differentiation of HSC may be tightly regulated by Ikaros gene products which may provide both positive signals for lymphocyte differentiation and negative signals to prevent or attenuate entry into the other hemopoietic pathways (FIG. 10). Finally, the body may sense the lack of lymphocytes and may attempt to correct this defect by increasing hemopoiesis. However, since the lymphocyte pathway is blocked, stem cells produced will passively or actively generate more progenitors for the other non-lymphocyte hemopoietic lineages. This may explain in part the abundance of erythroid, myeloid and megakaryocyte progenitors encountered in Ikaros −/− mice. The increased levels of myelopoiesis relative to erythropoiesis detected in older mutant animals may be caused by infections and septicemia that develop in these animals.

Ikaros gene products expressed during the earliest stages of fetal hemopoiesis (before the development of the lymphopoietic system) may influence the hemopoietic system in other ways than directing HCSs toward lymphocyte lineage commitment. HCSs have distinct migration pathways in the embryo and in the adult (Ikuta, K. et al. (1992) *Annu. Rev. Immunol.* 10:759–783). The migration of HCSs from one organ to another during embryonic development and the switch from embryonic to adult hemopoiesis that takes place at the IISC level may be in part controlled by the Ikaros gene (FIG. 10). The hypocellular bone marrow in the Ikaros mutant mice may result from a failure of HCS to migrate to the bone marrow and the high degree of extramedullary erythropoiesis and myelopoiesis detected in the spleen of these animals may result from dysregulated transition from embryonic to adult hemopoiesis. Alternatively lack of thymocyte progenitors in the Ikaros mutant mice may hinder the homing of the HSC into bone marrow cavities. The spleen may become the primary site of extramedullary hemopoiesis in Ikaros mutant mice because the hemopoietic compartment in the bone marrow is severely deficient.

The Ikaros gene plays an essential role for lymphocyte specification in the mouse hemopoietic system. Absence of functional Ikaros proteins leads to a total blockade in the development of T cells, B cells and NK cells. Ikaros mutant mice will provide an experimental system for addressing the molecular components which exist downstream of the Ikaros gene and whose expression is detrimental for lymphocyte specification and development.

An Ikaros Transgenic Mouse with a Deletion at Exon 7 of the Ikaros Gene

The Ikaros gene is believed to be a necessary factor for the generation and maintenance of early hemopoietic progenitors since it is expressed during embryonic hemopoiesis prior to lymphocyte ontogeny (fetal liver day 10). A mutation at the Ikaros locus which brings about a total loss of function at the level of its transcription activators and suppressors can lead to an embryonic lethal due to an impairment in the production of embryonic blood.

A recombination vector targeting a deletion to the C-terminal part of the Ikaros proteins was made and used to generate transgenic animals heterozygous and homozygous for a deletion in exon 7. This mutation is expected to generate proteins that appear only partially active in transcription.

Transcripts from this mutated locus lack exon 7. The encoded proteins, are expected to bind homologous or heterologous nuclear factors during lymphocyte development. This mutation is expected to interfere with the role of the Ikaros proteins in gene regulation but is not expected to totally abrogate their function in lymphocyte transcription.

Truncated Ikaros isoforms lacking the C-terminal domain encoded by exon 7 and shared by all of these proteins can bind DNA with the same specificity as their full length counterparts (as determined by gel retardation assays). However the ability of these truncated proteins to activate transcription appears to be significantly lower than that of their full length counterparts as determined in transient expression assays and experiments using Ikaros-lex-A hybrid proteins. Acidic motifs present in this C-terminal portion may serve as potential transcription activation domains and may be responsible for this effect. Deletion of an activation domain located in the deleted C-terminal region may be responsible for the decrease on their ability to activate transcription. The deleted C-terminal region contains in addition to the activation a dimerization domain for the Ikaros proteins established in the yeast two hybrid system.

Figure 11:
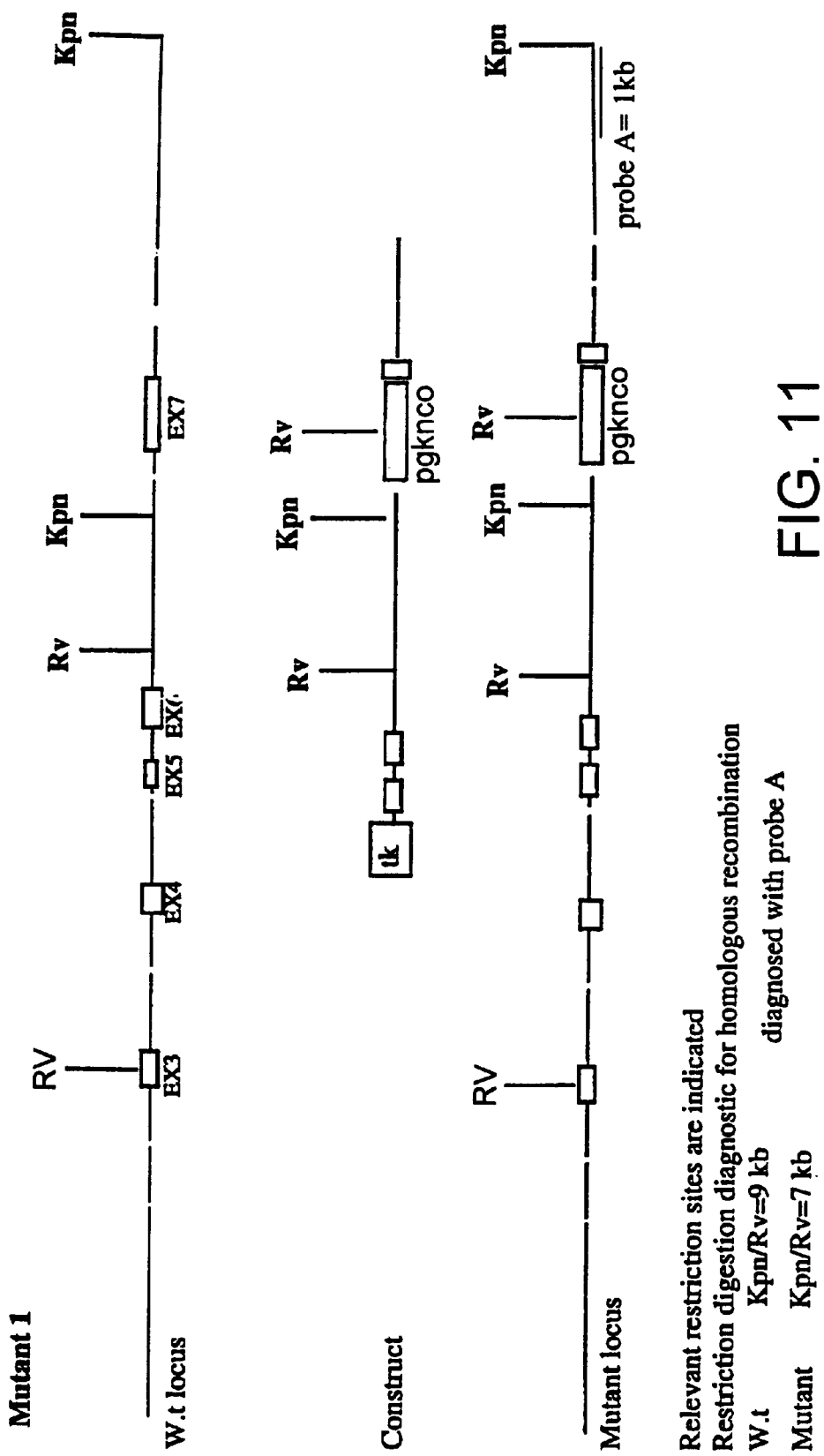
FIG. 11 shows the targeted replacement of 700 bp of exon 7 by the neomycin gene.

Replacement of 700 bp of exon 7 (FIG. 11) by the neomycin gene give rise to translation products which stop short of the shared C-terminal domain. These proteins are expected to bind DNA since they have a high affinity DNA binding domain at their N-terminus. However they should be compromised in their ability to activate transcription since part of their activation domain resides in their C-terminus. In lymphocytes heterozygous for this mutation, these mutant proteins may compete with their wild type counterparts for binding sites thus interfering with their function and with normal lymphocyte differentiation. Hematopoietic stem cells homozygous for this mutation may exhibit partial to total loss of Ikaros function depending on the ability of these truncated proteins to support transcripti on in vivo. The hematopoietic phenotype manife sted by these cells can vary from an early to a late lymphocyte arrest or to aberrant events in T cell homeostasis.

The Hemopoietic Populations of Mice Homozygous for the C-Terminal Ikaros Mutation Two independent embryonic stem cell lines with legitimate homologous recombination events were used to generate mice with germ line transmission of this mutation. Mice homozygous for this Ikaros mutation are born with the expected Mendelian frequency and are indistinguishable from wild type litter mates unless they are infected by opportunistic microorganisms. However the level of infections is not as extensive as with the N-terminal mutant homozygous mice and many animals survive for extended periods under sterile conditions. Male mutant homozygotes have successfully been bred with female heterozygous mutants.

Analysis of the hemopoietic system of a number of homozygous animals was performed. In contrast to the microscopically detectable thymic rudiment in the line of homozygous animals described above (the exon 3/4 deletion), this line of C-terminal homozygous mutants have a normal sized thymus. However, the ratio of $CD4^+/CD8^+$ and $CD4^+/CD8^+$ populations differed from those in wild type controls. The $CD4^+/CD8^+$ population was decreased in both healthy but mostly in the sick animals while the $CD4^+$ population was increased. Increased number of mature $CD4^+$ T cells were also detected in the spleen of healthy animals, while the $CD8^+$ population was similar in numbers to wild type litter mates. However in many sick homozygous mice, these mature $CD4^+$ and $CD8^+$ populations but predominantly the $CD4^+/CD8^+$ cells were greatly diminished.

In contrast to the presence of T lymphocytes from the early to the late stages of their development, B cells and their earliest identifiable progenitors were absent from all the hemopoietic centers analyzed in the Ikaros C-terminal –/– mutant mice.

The myeloid and erythroid lineages in these hemopoietic organs were intact and in a few cases elevated as in the N-terminal Ikaros homozygous mice. No peripheral lymphatic centers i.e. inguinal, cervical, axillary and mesenteric lymph nodes as well as Peyer's patches and lymphocyte follicles in the gastrointestinal tract were found in these Ikaros –/– mutant mice.

An Ikaros Transgenic Mouse with Two Ikaros Mutations (one Ikaros allele with a mutation that deletes the C-terminal portion of the protein, and the other Ikaros allele with a deletion in its DNA binding domain)

Mice homozygous for a germ line deletion of exons encoding the DNA binding domain of the Ikaros proteins lack T, B and NK lymphocytes and their progenitors. Analysis of the hemolymphopoietic system of mice homozygous for a germ line deletion of the C-terminal part of the Ikaros proteins has begun. In addition, mice heterozygous for the C-terminal and DNA binding mutations have been bred with one another to determine whether the two mutations can functionally complement each other with intermediate effects or defects in the development of the lymphopoietic system.

Transgenic Mice which Overexpress Ikaros Isoforms

Figure 12:
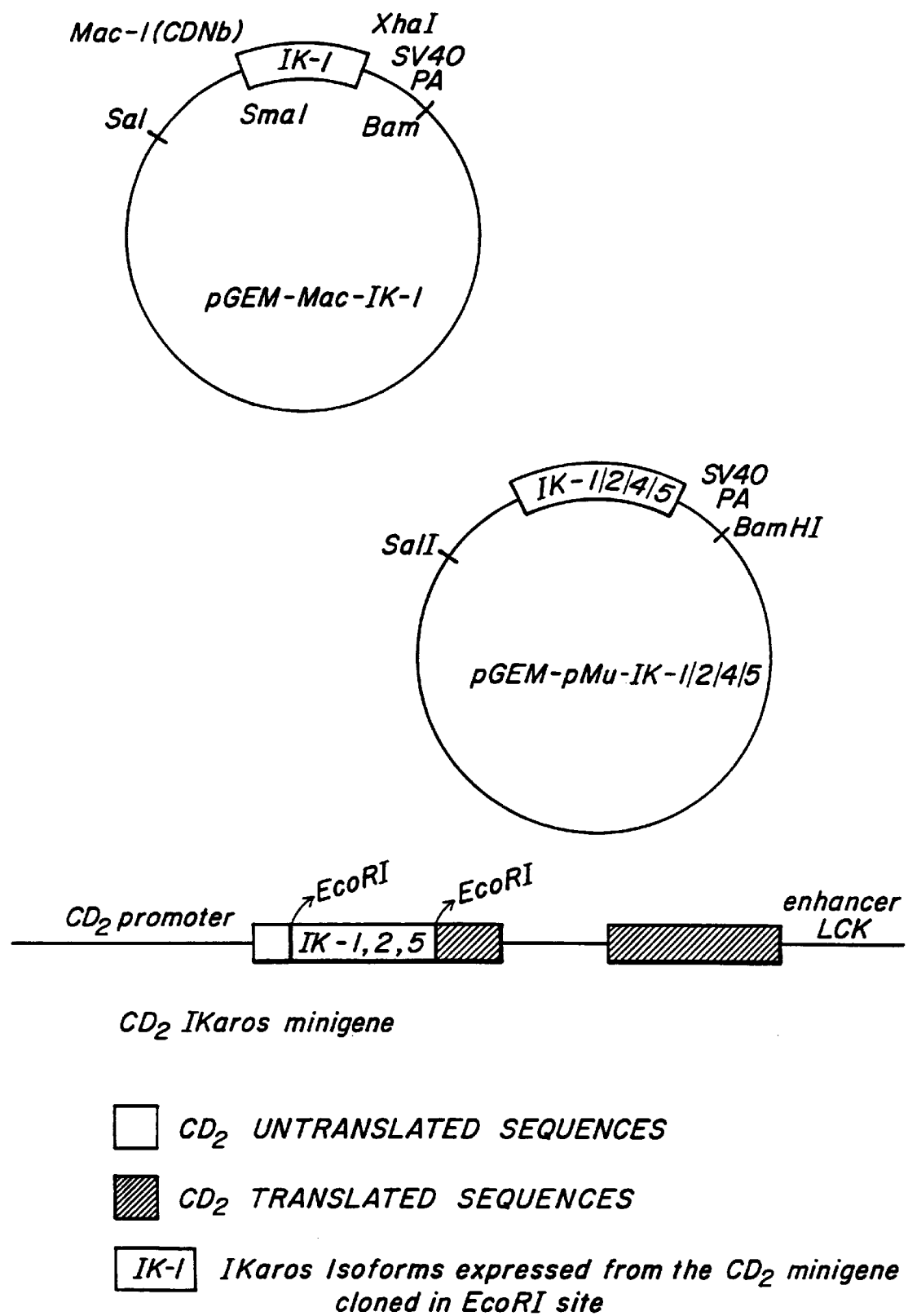
FIG. 12 is a map of two Ikaros plasmids.

Overexpression of Ikaros isoforms (Ik-1, -2, -4, -5) can be obtained by using the pMu expression cassette (to drive expression in the B lineage, 4 transgenic lines) (FIG. 12B) or by using the CD2 mini gene (to drive expression in the T lineage, 4 transgenic lines) (FIG. 12C)

Ikaros overexpression vectors have been generated using the immunoglobulin promoter enhancer regulatory sequences driving Ikaros isoform expression in the hemopoietic/lymphopoietic system. These vectors were generated in order to determine whether expression of Ikaros at the wrong times during development affects the developmental outcome of the B or T cell pathways to reconstitute the genetic background of the Ikaros mutant mice and functionally dissect the Ikaros proteins.

Overexpression of IK-1 in the myeloid lineage can be obtained by using the Mac-1 (CD11b) expression cassette. (FIG. 12A). The expression cassettes are excised from the pGEM backbone and introduced into mouse male pronuclei where they integrate transgenic mice as pronulcei chromosomes. The male pronuclei are then used to generate transgenic mice as described above.

Other Embodiments

Nucleic acid encoding all or part of the Ikaros gene can be used to transform cells. For example, the Ikaros gene, e.g., a mis-expressing or mutant form of the Ikaros gene, e.g., a deletion, or DNA encoding an Ikaros protein can be used to transform a cell and to produce a cell in which the cell's genomic Ikaros gene has been replaced by the transformed gene, producing, e.g., a cell deleted for the Ikaros gene. As described above, this approach can be used with cells capable of being grown in culture, e.g., cultured stem cells, to investigate the function of the Ikaros gene.

Analogously, nucleic acid encoding all or part of the Ikaros gene, e.g., a misexpression expressing or mutant form of the gene, e.g., a deletion, can be used to transform a cell which subsequently gives rise to a transgenic animal. This approach can be used to create, e.g., a transgenic animal in which the Ikaros gene is, e.g., inactivated, e.g., by a deletion. Homozygous transgenic animals can be made by crosses between the offspring of a founder transgenic animal. Cell or tissue cultures can be derived from a transgenic animal. A subject at risk for a disorder characterized by an abnormality in T cell development or function e.g., leukemia, can be detected by comparing the structure of the subject's Ikaros gene with the structure of a wild type Ikaros gene. Departure from the wild type structure by, e.g., frameshifts, critical point mutations, deletions, insertions, or translocations, are indicative of risk. The DNA sequence of the coding region of several exons as well as several intron exon boundaries are included herein. Other regions can be obtained or sequenced by methods known to those skilled in the art.

Embodiments of the invention also include animals having an Ikaros transgene and a second transgene which allows control over the expression of the Ikaros gene.

In vivo site-specific genetic manipulation together with genetic crosses between transgenic animals can be used to make animals which express the subject Ikaros protein in a developmentally regulated or tissue-specific manner. It is often desirable to limit the expression of a transgene to a particular stage of development or to a specific tissue. For example, many transgenes have deleterious effects on the cells of the transgenic animal in which they are expressed; thus, it is difficult to construct transgenic animals expressing these genes. Also, many promoters are "leaky" resulting in minimal levels of transcription of their target gene in all cell types. In many instances, it is desirable for a gene to be tightly repressed in all cells except those of a specific tissue. It may also be useful to study the role of a particular gene in development by causing or preventing its expression in particular tissues or at particular stages of development. One approach to the regulation of transgencs involves control of gene expression in vivo in either a tissue-specific manner or at a specific stage of the animal's development via site-specific genetic recombination.

Genetic techniques which allow for the expression of transgenes can be regulated via site-specific genetic manipulation in vivo are known to those skilled in the art. Genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of the subject protein. For example, excision of a target sequence which interferes with the expression of the subject protein can be designed to activate expression of that protein. This interference with expression of the subject protein can result from a variety of mechanisms, such as a spatial separation of the subject protein gene from the promoter element resulting in the inhibition of transcription of the Ikaros gene. In another instance, a target sequence containing an internal stop codon can be used to prevent translation of the subject protein. Alternatively, in situations where the target sequence comprises the subject gene coding sequence or the promoter element, recombinase catalyzed excision can be used to inhibit expression of the subject protein via excision of these sequences. Nucleic acid constructs can also be made wherein a target sequence containing a sequence encoding the subject protein is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

The cre/loxP recombinase system of bacteriophage P1 (Lakso et al. *PNAS* 89:6232–6236; Orban et al. *PNAS* 89:6861–6865) and the FLP recombinase system of *Saccharomyces cerevisiae* (O'Gorman et al. *Science* 251:1351–1355; PCT publication WO 92/15694) are examples of in vivo site-specific genetic recombination systems known in the art. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. *J. Biol. Chem.* 259:1509–1514). The Cre recombinase catalyzes the excision of the target sequence when the loxP sequences are oriented as direct repeats and catalyzes inversion of the target sequence when loxP sequences are oriented as inverted repeats.

Use of the cre/loxP recombinase system to regulate expression of the Ikaros protein requires the construction of a transgenic animal containing transgenes encoding both the Cre recombinase and the subject protein. Mice containing both the Cre recombinase and the subject protein genes can be provided through the construction of double transgenic mice. A convenient method for providing such mice is to mate two transgenic animals each containing a transgene. Double transgenic progeny of this mating are identified by screening the resulting offspring for the presence of both transgenes. The progeny may be tested for the presence of the constructs by Southern blot analysis of a segment of tissue. Typically, a small part of the tail is used for this purpose.

Recombinant vectors can be constructed wherein the nucleic acid sequence encoding the Ikaros protein is separated from a promoter element, e.g., a constitutive promoter, by an target sequence flanked by loxP sequences. This excisable target sequence can be used to inhibit expression of the Ikaros protein by, for example, containing an internal stop codon. In such a case, expression of the subject protein will be activated in cells containing Cre recombinase activity by excision of the target sequence and ligation of the abutting sequences. In this instance, excision of the target sequence results in the activation of protein expression at the level of translational. Alternatively, the target sequence can be placed in such a position that Cre recombinase mediated excision results in the promoter element being brought into close enough proximity to the subject gene to confer transcriptional activation. In this instance, the target sequence inhibits transcription of the subject protein gene by spatially separating the promoter element from the coding sequence. In another construct, the target sequence can comprise the nucleic acid sequence encoding the Ikaros protein which is oriented in a 3' to 5' with respect to the promoter. In this orientation the promoter will not be capable of activating transcription of the subject nucleic acid sequence. In this instance, Cre recombinase will catalyze the inversion of the target sequence encoding the Ikaros protein and thereby bring the 5' region of the coding sequence into the proper orientation with respect to the promoter for transcriptional activation.

In each of the above instances, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation or inactivation expression of the Ikaros protein can be regulated via regulation of recombinase expression.

Suitable recombinant vectors can be produced, for example, wherein a gene encoding the Cre recombinase is operably linked to a tissue-specific promoter, e.g., the mouse lck promoter which activates transcription in thymocytes. Tissue-specific expression of the Cre recombinase in each of the instances given above will result in a corresponding tissue-specific excision of the target sequence and activation or inactivation of the expression of the subject protein in that particular tissue. Thus, expression of the Ikaros protein will be up- or down-regulated only in cells expressing Cre recombinase activity.

One advantage derived from initially constructing transgenic mice containing a nucleotide sequence encoding the subject protein in a Cre recombinase mediated expressible format is evident when expression of the subject protein is deleterious to the transgenic animal. In such an instance, a founder population, in which the subject transgene is silent in all tissues, can be maintained. Individuals of this founder population can be crossed with animals expressing the Cre recombinase in, for example, one or more tissues. Thus, the creation of a founder population in which the subject transgene is silent will allow the study of genes which when expressed confer, for example, a lethal phenotype.

In instances where expression of the subject protein is not highly deleterious to the transgenic animal, tissue-specific gene activation systems similar to those described above can be devised which employs transgenic mice transfected with a single nucleic acid molecule. In such instances, the Cre recombinase and the nucleotide sequence encoding the subject protein are carried by the same vector and are integrated at the same chromosomal locus. Since the Cre recombinase is a trans-acting factor, the recombinase and the gene for which tissue-specific transcriptional activation is desired may be integrated at the same or different locations in the host genome.

Moreover, a tissue-specific promoter can be operably linked to more than one nucleic acid sequence, each encoding a different protein. In addition, more than one nucleic acid sequence containing a target sequence which inhibits protein expression, for example, can be introduced into cells. Thus, if desired, the subject Ikaros protein can be co-expressed with other transgenes where the expression of each protein is regulated in a tissue-specific or developmental stage-specific manner.

All of the above-cited references and publications are hereby incorporated by reference.

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 1788 base pairs
      (B) TYPE: nucleic acid
      (C) STRANDEDNESS: single
      (D) TOPOLOGY: linear (ii) MOLECULE TYPE: cDNA (ix) FEATURE:
    (A) NAME/KEY: CDS
    (B) LOCATION: 223..1515

(xi) SEQUENCE DESCRIPTION: SEQ ID NO:1:

```
AATTCGTTCT ACCTTCTCTG AACCCCAGTG GTGTGTCAAG GCCGGACTGG GAGCTTGGGG      60

GAAGAGGAAG AGGAAGAGGA ATCTGCGGCT CATCCAGGGA TCAGGGTCCT TCCCAAGTGG     120

CCACTCAGAG GGGACTCAGA GCAAGTCTAG ATTTGTGTGG CAGAGAGAGA CAGCTCTCGT     180

TTGGCCTTGG GGAGGCACAA GTCTGTTGAT AACCTGAAGA CA                       222
```

```
ATG GAT GTC GAT GAG GGT CAA GAC ATG TCC CAA GTT TCA GGA AAG GAG      270
Met Asp Val Asp Glu Gly Gln Asp Met Ser Gln Val Ser Gly Lys Glu
 1               5                  10                  15

AGC CCC CCA GTC AGT GAC ACT CCA GAT GAA GGG GAT GAG CCC ATG CCT      318
Ser Pro Pro Val Ser Asp Thr Pro Asp Glu Gly Asp Glu Pro Met Pro
             20                  25                  30

GTC CCT GAG GAC CTG TCC ACT ACC TCT GGA GCA CAG CAG AAC TCC AAG      366
Val Pro Glu Asp Leu Ser Thr Thr Ser Gly Ala Gln Gln Asn Ser Lys
         35                  40                  45

AGT GAT CGA GGC ATG GGT GAA CGG CCT TTC CAG TGC AAC CAG TCT GGG      414
Ser Asp Arg Gly Met Gly Glu Arg Pro Phe Gln Cys Asn Gln Ser Gly
 50                  55                  60

GCC TCC TTT ACC CAG AAA GGC AAC CTC CTG CGG CAC ATC AAG CTG CAC      462
Ala Ser Phe Thr Gln Lys Gly Asn Leu Leu Arg His Ile Lys Leu His
65                   70                  75                  80

TCG GGT GAG AAG CCC TTC AAA TGC CAT CTT TGC AAC TAT GCC TGC CGC      510
Ser Gly Glu Lys Pro Phe Lys Cys His Leu Cys Asn Tyr Ala Cys Arg
                 85                  90                  95

CGG AGG GAC GCC CTC ACC GGC CAC CTG AGG ACG CAC TCC GTT GGT AAG      558
Arg Arg Asp Ala Leu Thr Gly His Leu Arg Thr His Ser Val Gly Lys
             100                 105                 110

CCT CAC AAA TGT GGA TAT TGT GGC CGG AGC TAT AAA CAG CGA AGC TCT      606
Pro His Lys Cys Gly Tyr Cys Gly Arg Ser Tyr Lys Gln Arg Ser Ser
         115                 120                 125

TTA GAG GAG CAT AAA GAG CGA TGC CAC AAC TAC TTG GAA AGC ATG GGC      654
Leu Glu Glu His Lys Glu Arg Cys His Asn Tyr Leu Glu Ser Met Gly
130                 135                 140

CTT CCG GGC GTG TGC CCA GTC ATT AAG GAA GAA ACT AAC CAC AAC GAG      702
Leu Pro Gly Val Cys Pro Val Ile Lys Glu Glu Thr Asn His Asn Glu
145                 150                 155                 160

ATG GCA GAA GAC CTG TGC AAG ATA GGA GCA GAG AGG TCC CTT GTC CTG      750
Met Ala Glu Asp Leu Cys Lys Ile Gly Ala Glu Arg Ser Leu Val Leu
                 165                 170                 175

GAC AGG CTG GCA AGC AAT GTC GCC AAA CGT AAG AGC TCT ATG CCT CAG      798
Asp Arg Leu Ala Ser Asn Val Ala Lys Arg Lys Ser Ser Met Pro Gln
             180                 185                 190

AAA TTT CTT GGA GAC AAG TGC CTG TCA GAC ATG CCC TAT GAC AGT GCC      846
Lys Phe Leu Gly Asp Lys Cys Leu Ser Asp Met Pro Tyr Asp Ser Ala
         195                 200                 205

AAC TAT GAG AAG GAG GAT ATG ATG ACA TCC CAC GTG ATG GAC CAG GCC      894
Asn Tyr Glu Lys Glu Asp Met Met Thr Ser His Val Met Asp Gln Ala
     210                 215                 220

ATC AAC AAT GCC ATC AAC TAC CTG GGG GCT GAG TCC CTG CGC CCA TTG      942
Ile Asn Asn Ala Ile Asn Tyr Leu Gly Ala Glu Ser Leu Arg Pro Leu
225                 230                 235                 240

GTG CAG ACA CCC CCC GGT AGC TCC GAG GTG GTG CCA GTC ATC AGC TCC      990
Val Gln Thr Pro Pro Gly Ser Ser Glu Val Val Pro Val Ile Ser Ser
```

```
ATG TAC CAG CTG CAC AAG CCC CCC TCA GAT GGC CCC CCA CGG TCC AAC      1038
Met Tyr Gln Leu His Lys Pro Pro Ser Asp Gly Pro Pro Arg Ser Asn
            260             265             270

CAT TCA GCA CAG GAC GCC GTG GAT AAC TTG CTG CTG CTG TCC AAG GCC      1086
His Ser Ala Gln Asp Ala Val Asp Asn Leu Leu Leu Leu Ser Lys Ala
        275             280             285

AAG TCT GTG TCA TCG GAG CGA GAG GCC TCC CCG AGC AAC AGC TGC CAA      1134
Lys Ser Val Ser Ser Glu Arg Glu Ala Ser Pro Ser Asn Ser Cys Gln
    290             295             300

GAC TCC ACA GAT ACA GAG AGC AAC GCG GAG GAA CAG CGC AGC GGC CTT      1182
Asp Ser Thr Asp Thr Glu Ser Asn Ala Glu Glu Gln Arg Ser Gly Leu
305             310             315             320

ATC TAC CTA ACC AAC CAC ATC AAC CCG CAT GCA CGC AAT GGG CTG GCT      1230
Ile Tyr Leu Thr Asn His Ile Asn Pro His Ala Arg Asn Gly Leu Ala
                325             330             335

CTC AAG GAG GAG CAG CGC GCC TAC GAG GTG CTG AGG GCG GCC TCA GAG      1278
Leu Lys Glu Glu Gln Arg Ala Tyr Glu Val Leu Arg Ala Ala Ser Glu
            340             345             350

AAC TCG CAG GAT GCC TTC CGT GTG GTC AGC ACG AGT GGC GAG CAG CTG      1326
Asn Ser Gln Asp Ala Phe Arg Val Val Ser Thr Ser Gly Glu Gln Leu
        355             360             365

AAG GTG TAC AAG TGC GAA CAC TGC CGC GTG CTC TTC CTG GAT CAC GTC      1374
Lys Val Tyr Lys Cys Glu His Cys Arg Val Leu Phe Leu Asp His Val
    370             375             380

ATG TAT ACC ATT CAC ATG GGC TGC CAT GGC TGC CAT GGC TTT CGG GAT      1422
Met Tyr Thr Ile His Met Gly Cys His Gly Cys His Gly Phe Arg Asp
385             390             395             400

CCC TTT GAG TGT AAC ATG TGT GGT TAT CAC AGC CAG GAC AGG TAC GAG      1470
Pro Phe Glu Cys Asn Met Cys Gly Tyr His Ser Gln Asp Arg Tyr Glu
                405             410             415

TTC TCA TCC CAT ATC ACG CGG GGG GAG CAT CGT TAC CAC CTG AGC          1515
Phe Ser Ser His Ile Thr Arg Gly Glu His Arg Tyr His Leu Ser
            420             425             430

TAAACCCAGC CAGGCCCCAC TGAAGCACAA AGATAGCTGG TTATGCCTCC TTCCCGGCAG    1575

CTGGACCCAC AGCGGACAAT GTGGGAGTGG ATTTGCAGGC AGCATTTGTT CTTTTATGTT    1635

GGTTGTTTGG CGTTTCATTT GCGTTGGAAG ATAAGTTTTT AATGTTAGTG ACAGGATTGC    1695

ATTGCATCAG CAACATTCAC AACATCCATC CTTCTAGCCA GTTTTGTTCA CTGGTAGCTG    1755

AGGTTTCCCG GATATGTGGC TTCCTAACAC TCT                                1788

(2) INFORMATION FOR SEQ ID NO:2:

(i) SEQUENCE CHARACTERISTICS:
        (A) LENGTH: 1386 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..1386

(xi) SEQUENCE DESCRIPTION: SEQ ID NO:2:

AAT GTT AAA GTA GAG ACT CAG AGT GAT GAA GAG AAT GGG CGT GCC TGT        48
Asn Val Lys Val Glu Thr Gln Ser Asp Glu Glu Asn Gly Arg Ala Cys
 1               5                  10                  15

GAA ATG AAT GGG GAA GAA TGT GCG GAG GAT TTA CGA ATG CTT GAT GCC        96
Glu Met Asn Gly Glu Glu Cys Ala Glu Asp Leu Arg Met Leu Asp Ala
```

-continued

| | | | |
|---|---|---|---|
| TCG GGA GAG AAA ATG AAT GGC TCC CAC AGG GAC CAA GGC AGC TCG GCT | 144 | | |
| Ser Gly Glu Lys Met Asn Gly Ser His Arg Asp Gln Gly Ser Ser Ala | | | |
| 35 40 45 | | | |
| TTG TCG GGA GTT GGA GGC ATT CGA CTT CCT AAC GGA AAA CTA AAG TGT | 192 | | |
| Leu Ser Gly Val Gly Gly Ile Arg Leu Pro Asn Gly Lys Leu Lys Cys | | | |
| 50 55 60 | | | |
| GAT ATC TGT GGG ATC ATT TGC ATC GGG CCC AAT GTG CTC ATG GTT CAC | 240 | | |
| Asp Ile Cys Gly Ile Ile Cys Ile Gly Pro Asn Val Leu Met Val His | | | |
| 65 70 75 80 | | | |
| AAA AGA AGC CAC ACT GGA GAA CGG CCC TTC CAG TGC AAT CAG TGC GGG | 288 | | |
| Lys Arg Ser His Thr Gly Glu Arg Pro Phe Gln Cys Asn Gln Cys Gly | | | |
| 85 90 95 | | | |
| GCC TCA TTC ACC CAG AAG GGC AAC CTG CTC CGG CAC ATC AAG CTG CAT | 336 | | |
| Ala Ser Phe Thr Gln Lys Gly Asn Leu Leu Arg His Ile Lys Leu His | | | |
| 100 105 110 | | | |
| TCC GGG GAG AAG CCC TTC AAA TGC CAC CTC TGC AAC TAC GCC TGC CGC | 384 | | |
| Ser Gly Glu Lys Pro Phe Lys Cys His Leu Cys Asn Tyr Ala Cys Arg | | | |
| 115 120 125 | | | |
| CGG AGG GAC GCC CTC ACT GGC CAC CTG AGG ACG CAC TCC GTT GGT AAA | 432 | | |
| Arg Arg Asp Ala Leu Thr Gly His Leu Arg Thr His Ser Val Gly Lys | | | |
| 130 135 140 | | | |
| CCT CAC AAA TGT GGA TAT TGT GGC CGA AGC TAT AAA CAG CGA ACG TCT | 480 | | |
| Pro His Lys Cys Gly Tyr Cys Gly Arg Ser Tyr Lys Gln Arg Thr Ser | | | |
| 145 150 155 160 | | | |
| TTA GAG GAA CAT AAA GAG CGC TGC CAC AAC TAC TTG GAA AGC ATG GGC | 528 | | |
| Leu Glu Glu His Lys Glu Arg Cys His Asn Tyr Leu Glu Ser Met Gly | | | |
| 165 170 175 | | | |
| CTT CCG GGC ACA CTG TAC CCA GTC ATT AAA GAA GAA ACT AAG CAC AGT | 576 | | |
| Leu Pro Gly Thr Leu Tyr Pro Val Ile Lys Glu Glu Thr Lys His Ser | | | |
| 180 185 190 | | | |
| GAA ATG GCA GAA GAC CTG TGC AAG ATA GGA TCA GAG AGA TCT CTC GTG | 624 | | |
| Glu Met Ala Glu Asp Leu Cys Lys Ile Gly Ser Glu Arg Ser Leu Val | | | |
| 195 200 205 | | | |
| CTG GAC AGA CTA GCA AGT AAT GTC GCC AAA CGT AAG AGC TCT ATG CCT | 672 | | |
| Leu Asp Arg Leu Ala Ser Asn Val Ala Lys Arg Lys Ser Ser Met Pro | | | |
| 210 215 220 | | | |
| CAG AAA TTT CTT GGG GAC AAG GGC CTG TCC GAC ACG CCC TAC GAC AGT | 720 | | |
| Gln Lys Phe Leu Gly Asp Lys Gly Leu Ser Asp Thr Pro Tyr Asp Ser | | | |
| 225 230 235 240 | | | |
| GCC ACG TAC GAG AAG GAG AAC GAA ATG ATG AAG TCC CAC GTG ATG GAC | 768 | | |
| Ala Thr Tyr Glu Lys Glu Asn Glu Met Met Lys Ser His Val Met Asp | | | |
| 245 250 255 | | | |
| CAA GCC ATC AAC AAC GCC ATC AAC TAC CTG GGG GCC GAG TCC CTG CGC | 816 | | |
| Gln Ala Ile Asn Asn Ala Ile Asn Tyr Leu Gly Ala Glu Ser Leu Arg | | | |
| 260 265 270 | | | |
| CCG CTG GTG CAG ACG CCC CCG GGC GGT TCC GAG GTG GTC CCG GTC ATC | 864 | | |
| Pro Leu Val Gln Thr Pro Pro Gly Gly Ser Glu Val Val Pro Val Ile | | | |
| 275 280 285 | | | |
| AGC CCG ATG TAC CAG CTG CAC AGG CGC TCG GAG GGC ACC CCG CGC TCC | 912 | | |
| Ser Pro Met Tyr Gln Leu His Arg Arg Ser Glu Gly Thr Pro Arg Ser | | | |
| 290 295 300 | | | |
| AAC CAC TCG GCC CAG GAC AGC GCC GTG GAG TAC CTG CTG CTC TCC | 960 | | |
| Asn His Ser Ala Gln Asp Ser Ala Val Glu Tyr Leu Leu Leu Ser | | | |
| 305 310 315 320 | | | |
| AAG GCC AAG TTG GTG CCC TCG GAG CGC GAG GCG TCC CCG AGC AAC AGC | 1008 | | |
| Lys Ala Lys Leu Val Pro Ser Glu Arg Glu Ala Ser Pro Ser Asn Ser | | | |
| 325 330 335 | | | |
| TGC CAA GAC TCC ACG GAC ACC GAG AGC AAC AAC GAG GAG CAG CGC AGC | 1056 | | |

```
                                                           -continued

Cys Gln Asp Ser Thr Asp Thr Glu Ser Asn Asn Glu Glu Gln Arg Ser
            340                 345                 350

GGT CTT ATC TAC CTG ACC AAC CAC ATC GCC CGA CGC GCG CAA CGC GTG         1104
Gly Leu Ile Tyr Leu Thr Asn His Ile Ala Arg Arg Ala Gln Arg Val
            355                 360                 365

TCG CTC AAG GAG GAG CAC CGC GCC TAC GAC CTG CTG CGC GCC GCC TCC         1152
Ser Leu Lys Glu Glu His Arg Ala Tyr Asp Leu Leu Arg Ala Ala Ser
        370                 375                 380

GAG AAC TCG CAG GAC GCG CTC CGC GTG GTC AGC ACC AGC GGG GAG CAG         1200
Glu Asn Ser Gln Asp Ala Leu Arg Val Val Ser Thr Ser Gly Glu Gln
385                 390                 395                 400

ATG AAG GTG TAC AAG TGC GAA CAC TGC CGG GTG CTC TTC CTG GAT CAC         1248
Met Lys Val Tyr Lys Cys Glu His Cys Arg Val Leu Phe Leu Asp His
                405                 410                 415

GTC ATG TAC ACC ATC CAC ATG GGC TGC CAC GGC TTC CGT GAT CCT TTT         1296
Val Met Tyr Thr Ile His Met Gly Cys His Gly Phe Arg Asp Pro Phe
            420                 425                 430

GAG TGC AAC ATG TGC GGC TAC CAC AGC CAG GAC CGG TAC GAG TTC TCG         1344
Glu Cys Asn Met Cys Gly Tyr His Ser Gln Asp Arg Tyr Glu Phe Ser
        435                 440                 445

TCG CAC ATA ACG CGA GGG GAG CAC CGC TTC CAC ATG AGC TAA               1386
Ser His Ile Thr Arg Gly Glu His Arg Phe His Met Ser
450                 455                 460

(2) INFORMATION FOR SEQ ID NO:3:

(i) SEQUENCE CHARACTERISTICS:
        (A) LENGTH: 1296 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1296

(xi) SEQUENCE DESCRIPTION: SEQ ID NO:3:

ATG GAT GTC GAT GAG GGT CAA GAC ATG TCC CAA GTT TCA GGA AAG GAG          48
Met Asp Val Asp Glu Gly Gln Asp Met Ser Gln Val Ser Gly Lys Glu
1               5                   10                  15

AGC CCC CCA GTC AGT GAC ACT CCA GAT GAA GGG GAT GAG CCC ATG CCT          96
Ser Pro Pro Val Ser Asp Thr Pro Asp Glu Gly Asp Glu Pro Met Pro
            20                  25                  30

GTC CCT GAG GAC CTG TCC ACT ACC TCT GGA GCA CAG CAG AAC TCC AAG         144
Val Pro Glu Asp Leu Ser Thr Thr Ser Gly Ala Gln Gln Asn Ser Lys
        35                  40                  45

AGT GAT CGA GGC ATG GCC AGT AAT GTT AAA GTA GAG ACT CAG AGT GAT         192
Ser Asp Arg Gly Met Ala Ser Asn Val Lys Val Glu Thr Gln Ser Asp
    50                  55                  60

GAA GAG AAT GGG CGT GCC TGT GAA ATG AAT GGG GAA GAA TGT GCA GAG         240
Glu Glu Asn Gly Arg Ala Cys Glu Met Asn Gly Glu Glu Cys Ala Glu
65                  70                  75                  80

GAT TTA CGA ATG CTT GAT GCC TCG GGA GAG AAA ATG AAT GGC TCC CAC         288
Asp Leu Arg Met Leu Asp Ala Ser Gly Glu Lys Met Asn Gly Ser His
                85                  90                  95

AGG GAC CAA GGC AGC TCG GCT TTG TCA GGA GTT GGA GGC ATT CGA CTT         336
Arg Asp Gln Gly Ser Ser Ala Leu Ser Gly Val Gly Gly Ile Arg Leu
            100                 105                 110

CCT AAC GGA AAA CTA AAG TGT GAT ATC TGT GGG ATC GTT TGC ATC GGG         384
Pro Asn Gly Lys Leu Lys Cys Asp Ile Cys Gly Ile Val Cys Ile Gly
        115                 120                 125
```

```
CCC AAT GTG CTC ATG GTT CAC AAA AGA AGT CAT ACT GGT GAA CGG CCT       432
Pro Asn Val Leu Met Val His Lys Arg Ser His Thr Gly Glu Arg Pro
    130                 135                 140

TTC CAG TGC AAC CAG TCT GGG GCC TCC TTT ACC CAG AAA GGC AAC CTC       480
Phe Gln Cys Asn Gln Ser Gly Ala Ser Phe Thr Gln Lys Gly Asn Leu
145                 150                 155                 160

CTG CGG CAC ATC AAG CTG CAC TCG GGT GAG AAG CCC TTC AAA TGC CAT       528
Leu Arg His Ile Lys Leu His Ser Gly Glu Lys Pro Phe Lys Cys His
                165                 170                 175

CTT TGC AAC TAT GCC TGC CGC CGG AGG GAC GCC CTC ACC GGC CAC CTG       576
Leu Cys Asn Tyr Ala Cys Arg Arg Arg Asp Ala Leu Thr Gly His Leu
            180                 185                 190

AGG ACG CAC TCC GGA GAC AAG TGC CTG TCA GAC ATG CCC TAT GAC AGT       624
Arg Thr His Ser Gly Asp Lys Cys Leu Ser Asp Met Pro Tyr Asp Ser
        195                 200                 205

GCC AAC TAT GAG AAG GAG GAT ATG ATG ACA TCC CAC GTG ATG GAC CAG       672
Ala Asn Tyr Glu Lys Glu Asp Met Met Thr Ser His Val Met Asp Gln
    210                 215                 220

GCC ATC AAC AAT GCC ATC AAC TAC CTG GGG GCT GAG TCC CTG CGC CCA       720
Ala Ile Asn Asn Ala Ile Asn Tyr Leu Gly Ala Glu Ser Leu Arg Pro
225                 230                 235                 240

TTG GTG CAG ACA CCC CCC GGT AGC TCC GAG GTG GTG CCA GTC ATC AGC       768
Leu Val Gln Thr Pro Pro Gly Ser Ser Glu Val Val Pro Val Ile Ser
                245                 250                 255

TCC ATG TAC CAG CTG CAC AAG CCC CCC TCA GAT GGC CCC CCA CGG TCC       816
Ser Met Tyr Gln Leu His Lys Pro Pro Ser Asp Gly Pro Pro Arg Ser
            260                 265                 270

AAC CAT TCA GCA CAG GAC GCC GTG GAT AAC TTG CTG CTG CTG TCC AAG       864
Asn His Ser Ala Gln Asp Ala Val Asp Asn Leu Leu Leu Leu Ser Lys
        275                 280                 285

GCC AAG TCT GTG TCA TCG GAG CGA GAG GCC TCC CCG AGC AAC AGC TGC       912
Ala Lys Ser Val Ser Ser Glu Arg Glu Ala Ser Pro Ser Asn Ser Cys
    290                 295                 300

CAA GAC TCC ACA GAT ACA GAG AGC AAC GCG GAG GAA CAG CGC AGC GGC       960
Gln Asp Ser Thr Asp Thr Glu Ser Asn Ala Glu Glu Gln Arg Ser Gly
305                 310                 315                 320

CTT ATC TAC CTA ACC AAC CAC ATC AAC CCG CAT GCA CGC AAT GGG CTG      1008
Leu Ile Tyr Leu Thr Asn His Ile Asn Pro His Ala Arg Asn Gly Leu
                325                 330                 335

GCT CTC AAG GAG GAG CAG CGC GCC TAC GAG GTG CTG AGG GCG GCC TCA      1056
Ala Leu Lys Glu Glu Gln Arg Ala Tyr Glu Val Leu Arg Ala Ala Ser
            340                 345                 350

GAG AAC TCG CAG GAT GCC TTC CGT GTG GTC AGC ACG AGT GGC GAG CAG      1104
Glu Asn Ser Gln Asp Ala Phe Arg Val Val Ser Thr Ser Gly Glu Gln
        355                 360                 365

CTG AAG GTG TAC AAG TGC GAA CAC TGC CGC GTG CTC TTC CTG GAT CAC      1152
Leu Lys Val Tyr Lys Cys Glu His Cys Arg Val Leu Phe Leu Asp His
    370                 375                 380

GTC ATG TAT ACC ATT CAC ATG GGC TGC CAT GGC TGC CAT GGC TTT CGG      1200
Val Met Tyr Thr Ile His Met Gly Cys His Gly Cys His Gly Phe Arg
385                 390                 395                 400

GAT CCC TTT GAG TGT AAC ATG TGT GGT TAT CAC AGC CAG GAC AGG TAC      1248
Asp Pro Phe Glu Cys Asn Met Cys Gly Tyr His Ser Gln Asp Arg Tyr
                405                 410                 415

GAG TTC TCA TCC CAT ATC ACG CGG GGG GAG CAT CGT TAC CAC CTG AGC      1296
Glu Phe Ser Ser His Ile Thr Arg Gly Glu His Arg Tyr His Leu Ser
            420                 425                 430
```

(2) INFORMATION FOR SEQ ID NO:4:

(i) SEQUENCE CHARACTERISTICS:
    (A) LENGTH: 2049 base pairs
    (B) TYPE: nucleic acid
    (C) STRANDEDNESS: double
    (D) TOPOLOGY: linear (ii) MOLECULE TYPE: cDNA (ix) FEATURE:
    (A) NAME/KEY: CDS
    (B) LOCATION: 223..1776

(xi) SEQUENCE DESCRIPTION: SEQ ID NO:4:

```
AATTCGTTCT ACCTTCTCTG AACCCCAGTG GTGTGTCAAG GCCGGACTGG GAGCTTGGGG      60

GAAGAGGAAG AGGAAGAGGA ATCTGCGGCT CATCCAGGGA TCAGGGTCCT TCCCAAGTGG     120

CCACTCAGAG GGGACTCAGA GCAAGTCTAG ATTTGTGTGG CAGAGAGAGA CAGCTCTCGT     180

TTGGCCTTGG GGAGGCACAA GTCTGTTGAT AACCTGAAGA CA ATG GAT GTC GAT        234
                                               Met Asp Val Asp
                                                1

GAG GGT CAA GAC ATG TCC CAA GTT TCA GGA AAG GAG AGC CCC CCA GTC       282
Glu Gly Gln Asp Met Ser Gln Val Ser Gly Lys Glu Ser Pro Pro Val
 5                  10                  15                  20

AGT GAC ACT CCA GAT GAA GGG GAT GAG CCC ATG CCT GTC CCT GAG GAC       330
Ser Asp Thr Pro Asp Glu Gly Asp Glu Pro Met Pro Val Pro Glu Asp
             25                  30                  35

CTG TCC ACT ACC TCT GGA GCA CAG CAG AAC TCC AAG AGT GAT CGA GGC       378
Leu Ser Thr Thr Ser Gly Ala Gln Gln Asn Ser Lys Ser Asp Arg Gly
         40                  45                  50

ATG GCC AGT AAT GTT AAA GTA GAG ACT CAG AGT GAT GAA GAG AAT GGG       426
Met Ala Ser Asn Val Lys Val Glu Thr Gln Ser Asp Glu Glu Asn Gly
     55                  60                  65

CGT GCC TGT GAA ATG AAT GGG GAA GAA TGT GCA GAG GAT TTA CGA ATG       474
Arg Ala Cys Glu Met Asn Gly Glu Glu Cys Ala Glu Asp Leu Arg Met
 70                  75                  80

CTT GAT GCC TCG GGA GAG AAA ATG AAT GGC TCC CAC AGG GAC CAA GGC       522
Leu Asp Ala Ser Gly Glu Lys Met Asn Gly Ser His Arg Asp Gln Gly
 85                  90                  95                 100

AGC TCG GCT TTG TCA GGA GTT GGA GGC ATT CGA CTT CCT AAC GGA AAA       570
Ser Ser Ala Leu Ser Gly Val Gly Gly Ile Arg Leu Pro Asn Gly Lys
             105                 110                 115

CTA AAG TGT GAT ATC TGT GGG ATC GTT TGC ATC GGG CCC AAT GTG CTC       618
Leu Lys Cys Asp Ile Cys Gly Ile Val Cys Ile Gly Pro Asn Val Leu
         120                 125                 130

ATG GTT CAC AAA AGA AGT CAT ACT GGT GAA CGG CCT TTC CAG TGC AAC       666
Met Val His Lys Arg Ser His Thr Gly Glu Arg Pro Phe Gln Cys Asn
     135                 140                 145

CAG TCT GGG GCC TCC TTT ACC CAG AAA GGC AAC CTC CTG CGG CAC ATC       714
Gln Ser Gly Ala Ser Phe Thr Gln Lys Gly Asn Leu Leu Arg His Ile
 150                 155                 160

AAG CTG CAC TCG GGT GAG AAG CCC TTC AAA TGC CAT CTT TGC AAC TAT       762
Lys Leu His Ser Gly Glu Lys Pro Phe Lys Cys His Leu Cys Asn Tyr
165                 170                 175                 180

GCC TGC CGC CGG AGG GAC GCC CTC ACC GGC CAC CTG AGG ACG CAC TCC       810
Ala Cys Arg Arg Arg Asp Ala Leu Thr Gly His Leu Arg Thr His Ser
             185                 190                 195

GTT GGT AAG CCT CAC AAA TGT GGA TAT TGT GGC CGG AGC TAT AAA CAG       858
Val Gly Lys Pro His Lys Cys Gly Tyr Cys Gly Arg Ser Tyr Lys Gln
         200                 205                 210

CGA AGC TCT TTA GAG GAG CAT AAA GAG CGA TGC CAC AAC TAC TTG GAA       906
Arg Ser Ser Leu Glu Glu His Lys Glu Arg Cys His Asn Tyr Leu Glu
```

-continued

```
          215                 220                 225
AGC ATG GGC CTT CCG GGC GTG TGC CCA GTC ATT AAG GAA GAA ACT AAC      954
Ser Met Gly Leu Pro Gly Val Cys Pro Val Ile Lys Glu Glu Thr Asn
        230                 235                 240

CAC AAC GAG ATG GCA GAA GAC CTG TGC AAG ATA GGA GCA GAG AGG TCC     1002
His Asn Glu Met Ala Glu Asp Leu Cys Lys Ile Gly Ala Glu Arg Ser
245                 250                 255                 260

CTT GTC CTG GAC AGG CTG GCA AGC AAT GTC GCC AAA CGT AAG AGC TCT     1050
Leu Val Leu Asp Arg Leu Ala Ser Asn Val Ala Lys Arg Lys Ser Ser
                265                 270                 275

ATG CCT CAG AAA TTT CTT GGA GAC AAG TGC CTG TCA GAC ATG CCC TAT     1098
Met Pro Gln Lys Phe Leu Gly Asp Lys Cys Leu Ser Asp Met Pro Tyr
            280                 285                 290

GAC AGT GCC AAC TAT GAG AAG GAG GAT ATG ATG ACA TCC CAC GTG ATG     1146
Asp Ser Ala Asn Tyr Glu Lys Glu Asp Met Met Thr Ser His Val Met
        295                 300                 305

GAC CAG GCC ATC AAC AAT GCC ATC AAC TAC CTG GGG GCT GAG TCC CTG     1194
Asp Gln Ala Ile Asn Asn Ala Ile Asn Tyr Leu Gly Ala Glu Ser Leu
    310                 315                 320

CGC CCA TTG GTG CAG ACA CCC CCC GGT AGC TCC GAG GTG GTG CCA GTC     1242
Arg Pro Leu Val Gln Thr Pro Pro Gly Ser Ser Glu Val Val Pro Val
325                 330                 335                 340

ATC AGC TCC ATG TAC CAG CTG CAC AAG CCC CCC TCA GAT GGC CCC CCA     1290
Ile Ser Ser Met Tyr Gln Leu His Lys Pro Pro Ser Asp Gly Pro Pro
                345                 350                 355

CGG TCC AAC CAT TCA GCA CAG GAC GCC GTG GAT AAC TTG CTG CTG CTG     1338
Arg Ser Asn His Ser Ala Gln Asp Ala Val Asp Asn Leu Leu Leu Leu
            360                 365                 370

TCC AAG GCC AAG TCT GTG TCA TCG GAG CGA GAG GCC TCC CCG AGC AAC     1386
Ser Lys Ala Lys Ser Val Ser Ser Glu Arg Glu Ala Ser Pro Ser Asn
        375                 380                 385

AGC TGC CAA GAC TCC ACA GAT ACA GAG AGC AAC GCG GAG GAA CAG CGC     1434
Ser Cys Gln Asp Ser Thr Asp Thr Glu Ser Asn Ala Glu Glu Gln Arg
    390                 395                 400

AGC GGC CTT ATC TAC CTA ACC AAC CAC ATC AAC CCG CAT GCA CGC AAT     1482
Ser Gly Leu Ile Tyr Leu Thr Asn His Ile Asn Pro His Ala Arg Asn
405                 410                 415                 420

GGG CTG GCT CTC AAG GAG GAG CAG CGC GCC TAC GAG GTG CTG AGG GCG     1530
Gly Leu Ala Leu Lys Glu Glu Gln Arg Ala Tyr Glu Val Leu Arg Ala
                425                 430                 435

GCC TCA GAG AAC TCG CAG GAT GCC TTC CGT GTG GTC AGC ACG AGT GGC     1578
Ala Ser Glu Asn Ser Gln Asp Ala Phe Arg Val Val Ser Thr Ser Gly
            440                 445                 450

GAG CAG CTG AAG GTG TAC AAG TGC GAA CAC TGC CGC GTG CTC TTC CTG     1626
Glu Gln Leu Lys Val Tyr Lys Cys Glu His Cys Arg Val Leu Phe Leu
        455                 460                 465

GAT CAC GTC ATG TAT ACC ATT CAC ATG GGC TGC CAT GGC TGC CAT GGC     1674
Asp His Val Met Tyr Thr Ile His Met Gly Cys His Gly Cys His Gly
    470                 475                 480

TTT CGG GAT CCC TTT GAG TGT AAC ATG TGT GGT TAT CAC AGC CAG GAC     1722
Phe Arg Asp Pro Phe Glu Cys Asn Met Cys Gly Tyr His Ser Gln Asp
485                 490                 495                 500

AGG TAC GAG TTC TCA TCC CAT ATC ACG CGG GGG GAG CAT CGT TAC CAC     1770
Arg Tyr Glu Phe Ser Ser His Ile Thr Arg Gly Glu His Arg Tyr His
                505                 510                 515

CTG AGC TAAACCCAGC CAGGCCCCAC TGAAGCACAA AGATAGCTGG TTATGCCTCC     1826
Leu Ser

TTCCCGGCAG CTGGACCCAC AGCGGACAAT GTGGGAGTGG ATTTGCAGGC AGCATTTGTT    1886
```

```
CTTTTATGTT GGTTGTTTGG CGTTTCATTT GCGTTGGAAG ATAAGTTTTT AATGTTAGTG      1946

ACAGGATTGC ATTGCATCAG CAACATTCAC AACATCCATC CTTCTAGCCA GTTTTGTTCA      2006

CTGGTAGCTG AGGTTTCCCG GATATGTGGC TTCCTAACAC TCT                        2049
```

(2) INFORMATION FOR SEQ ID NO:5:

(i) SEQUENCE CHARACTERISTICS:
        (A) LENGTH: 1170 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1170

(xi) SEQUENCE DESCRIPTION: SEQ ID NO:5:

```
ATG GAT GTC GAT GAG GGT CAA GAC ATG TCC CAA GTT TCA GGA AAG GAG        48
Met Asp Val Asp Glu Gly Gln Asp Met Ser Gln Val Ser Gly Lys Glu
 1               5                  10                  15

AGC CCC CCA GTC AGT GAC ACT CCA GAT GAA GGG GAT GAG CCC ATG CCT        96
Ser Pro Pro Val Ser Asp Thr Pro Asp Glu Gly Asp Glu Pro Met Pro
                20                  25                  30

GTC CCT GAG GAC CTG TCC ACT ACC TCT GGA GCA CAG CAG AAC TCC AAG       144
Val Pro Glu Asp Leu Ser Thr Thr Ser Gly Ala Gln Gln Asn Ser Lys
         35                  40                  45

AGT GAT CGA GGC ATG GGT GAA CGG CCT TTC CAG TGC AAC CAG TCT GGG       192
Ser Asp Arg Gly Met Gly Glu Arg Pro Phe Gln Cys Asn Gln Ser Gly
     50                  55                  60

GCC TCC TTT ACC CAG AAA GGC AAC CTC CTG CGG CAC ATC AAG CTG CAC       240
Ala Ser Phe Thr Gln Lys Gly Asn Leu Leu Arg His Ile Lys Leu His
 65                  70                  75                  80

TCG GGT GAG AAG CCC TTC AAA TGC CAT CTT TGC AAC TAT GCC TGC CGC       288
Ser Gly Glu Lys Pro Phe Lys Cys His Leu Cys Asn Tyr Ala Cys Arg
                 85                  90                  95

CGG AGG GAC GCC CTC ACC GGC CAC CTG AGG ACG CAC TCC GTC ATT AAG       336
Arg Arg Asp Ala Leu Thr Gly His Leu Arg Thr His Ser Val Ile Lys
                100                 105                 110

GAA GAA ACT AAC CAC AAC GAG ATG GCA GAA GAC CTG TGC AAG ATA GGA       384
Glu Glu Thr Asn His Asn Glu Met Ala Glu Asp Leu Cys Lys Ile Gly
        115                 120                 125

GCA GAG AGG TCC CTT GTC CTG GAC AGG CTG GCA AGC AAT GTC GCC AAA       432
Ala Glu Arg Ser Leu Val Leu Asp Arg Leu Ala Ser Asn Val Ala Lys
    130                 135                 140

CGT AAG AGC TCT ATG CCT CAG AAA TTT CTT GGA GAC AAG TGC CTG TCA       480
Arg Lys Ser Ser Met Pro Gln Lys Phe Leu Gly Asp Lys Cys Leu Ser
145                 150                 155                 160

GAC ATG CCC TAT GAC AGT GCC AAC TAT GAG AAG GAG GAT ATG ATG ACA       528
Asp Met Pro Tyr Asp Ser Ala Asn Tyr Glu Lys Glu Asp Met Met Thr
                165                 170                 175

TCC CAC GTG ATG GAC CAG GCC ATC AAC AAT GCC ATC AAC TAC CTG GGG       576
Ser His Val Met Asp Gln Ala Ile Asn Asn Ala Ile Asn Tyr Leu Gly
            180                 185                 190

GCT GAG TCC CTG CGC CCA TTG GTG CAG ACA CCC CCC GGT AGC TCC GAG       624
Ala Glu Ser Leu Arg Pro Leu Val Gln Thr Pro Pro Gly Ser Ser Glu
        195                 200                 205

GTG GTG CCA GTC ATC AGC TCC ATG TAC CAG CTG CAC AAG CCC CCC TCA       672
Val Val Pro Val Ile Ser Ser Met Tyr Gln Leu His Lys Pro Pro Ser
    210                 215                 220
```

```
GAT GGC CCC CCA CGG TCC AAC CAT TCA GCA CAG GAC GCC GTG GAT AAC       720
Asp Gly Pro Pro Arg Ser Asn His Ser Ala Gln Asp Ala Val Asp Asn
225                 230                 235                 240

TTG CTG CTG CTG TCC AAG GCC AAG TCT GTG TCA TCG GAG CGA GAG GCC       768
Leu Leu Leu Leu Ser Lys Ala Lys Ser Val Ser Ser Glu Arg Glu Ala
                245                 250                 255

TCC CCG AGC AAC AGC TGC CAA GAC TCC ACA GAT ACA GAG AGC AAC GCG       816
Ser Pro Ser Asn Ser Cys Gln Asp Ser Thr Asp Thr Glu Ser Asn Ala
            260                 265                 270

GAG GAA CAG CGC AGC GGC CTT ATC TAC CTA ACC AAC CAC ATC AAC CCG       864
Glu Glu Gln Arg Ser Gly Leu Ile Tyr Leu Thr Asn His Ile Asn Pro
        275                 280                 285

CAT GCA CGC AAT GGG CTG GCT CTC AAG GAG GAG CAG CGC GCC TAC GAG       912
His Ala Arg Asn Gly Leu Ala Leu Lys Glu Glu Gln Arg Ala Tyr Glu
    290                 295                 300

GTG CTG AGG GCG GCC TCA GAG AAC TCG CAG GAT GCC TTC CGT GTG GTC       960
Val Leu Arg Ala Ala Ser Glu Asn Ser Gln Asp Ala Phe Arg Val Val
305                 310                 315                 320

AGC ACG AGT GGC GAG CAG CTG AAG GTG TAC AAG TGC GAA CAC TGC CGC      1008
Ser Thr Ser Gly Glu Gln Leu Lys Val Tyr Lys Cys Glu His Cys Arg
                325                 330                 335

GTG CTC TTC CTG GAT CAC GTC ATG TAT ACC ATT CAC ATG GGC TGC CAT      1056
Val Leu Phe Leu Asp His Val Met Tyr Thr Ile His Met Gly Cys His
            340                 345                 350

GGC TGC CAT GGC TTT CGG GAT CCC TTT GAG TGT AAC ATG TGT GGT TAT      1104
Gly Cys His Gly Phe Arg Asp Pro Phe Glu Cys Asn Met Cys Gly Tyr
        355                 360                 365

CAC AGC CAG GAC AGG TAC GAG TTC TCA TCC CAT ATC ACG CGG GGG GAG      1152
His Ser Gln Asp Arg Tyr Glu Phe Ser Ser His Ile Thr Arg Gly Glu
    370                 375                 380

CAT CGT TAC CAC CTG AGC                                              1170
His Arg Tyr His Leu Ser
385                 390

(2) INFORMATION FOR SEQ ID NO:6:

(i) SEQUENCE CHARACTERISTICS:
        (A) LENGTH: 1128 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1128

(xi) SEQUENCE DESCRIPTION: SEQ ID NO:6:

ATG GAT GTC GAT GAG GGT CAA GAC ATG TCC CAA GTT TCA GGA AAG GAG        48
Met Asp Val Asp Glu Gly Gln Asp Met Ser Gln Val Ser Gly Lys Glu
1               5                   10                  15

AGC CCC CCA GTC AGT GAC ACT CCA GAT GAA GGG GAT GAG CCC ATG CCT        96
Ser Pro Pro Val Ser Asp Thr Pro Asp Glu Gly Asp Glu Pro Met Pro
                20                  25                  30

GTC CCT GAG GAC CTG TCC ACT ACC TCT GGA GCA CAG CAG AAC TCC AAG       144
Val Pro Glu Asp Leu Ser Thr Thr Ser Gly Ala Gln Gln Asn Ser Lys
            35                  40                  45

AGT GAT CGA GGC ATG GCC AGT AAT GTT AAA GTA GAG ACT CAG AGT GAT       192
Ser Asp Arg Gly Met Ala Ser Asn Val Lys Val Glu Thr Gln Ser Asp
        50                  55                  60

GAA GAG AAT GGG CGT GCC TGT GAA ATG AAT GGG GAA GAA TGT GCA GAG       240
Glu Glu Asn Gly Arg Ala Cys Glu Met Asn Gly Glu Glu Cys Ala Glu
```

-continued

```
         65                      70                      75                      80
GAT TTA CGA ATG CTT GAT GCC TCG GGA GAG AAA ATG AAT GGC TCC CAC                  288
Asp Leu Arg Met Leu Asp Ala Ser Gly Glu Lys Met Asn Gly Ser His
                         85                      90                      95

AGG GAC CAA GGC AGC TCG GCT TTG TCA GGA GTT GGA GGC ATT CGA CTT                  336
Arg Asp Gln Gly Ser Ser Ala Leu Ser Gly Val Gly Gly Ile Arg Leu
                100                     105                     110

CCT AAC GGA AAA CTA AAG TGT GAT ATC TGT GGG ATC GTT TGC ATC GGG                  384
Pro Asn Gly Lys Leu Lys Cys Asp Ile Cys Gly Ile Val Cys Ile Gly
            115                     120                     125

CCC AAT GTG CTC ATG GTT CAC AAA AGA AGT CAT ACT GGA GAC AAG TGC                  432
Pro Asn Val Leu Met Val His Lys Arg Ser His Thr Gly Asp Lys Cys
        130                     135                     140

CTG TCA GAC ATG CCC TAT GAC AGT GCC AAC TAT GAG AAG GAG GAT ATG                  480
Leu Ser Asp Met Pro Tyr Asp Ser Ala Asn Tyr Glu Lys Glu Asp Met
145                     150                     155                     160

ATG ACA TCC CAC GTG ATG GAC CAG GCC ATC AAC AAT GCC ATC AAC TAC                  528
Met Thr Ser His Val Met Asp Gln Ala Ile Asn Asn Ala Ile Asn Tyr
                165                     170                     175

CTG GGG GCT GAG TCC CTG CGC CCA TTG GTG CAG ACA CCC CCC GGT AGC                  576
Leu Gly Ala Glu Ser Leu Arg Pro Leu Val Gln Thr Pro Pro Gly Ser
            180                     185                     190

TCC GAG GTG GTG CCA GTC ATC AGC TCC ATG TAC CAG CTG CAC AAG CCC                  624
Ser Glu Val Val Pro Val Ile Ser Ser Met Tyr Gln Leu His Lys Pro
        195                     200                     205

CCC TCA GAT GGC CCC CCA CGG TCC AAC CAT TCA GCA CAG GAC GCC GTG                  672
Pro Ser Asp Gly Pro Pro Arg Ser Asn His Ser Ala Gln Asp Ala Val
210                     215                     220

GAT AAC TTG CTG CTG CTG TCC AAG GCC AAG TCT GTG TCA TCG GAG CGA                  720
Asp Asn Leu Leu Leu Leu Ser Lys Ala Lys Ser Val Ser Ser Glu Arg
225                     230                     235                     240

GAG GCC TCC CCG AGC AAC AGC TGC CAA GAC TCC ACA GAT ACA GAG AGC                  768
Glu Ala Ser Pro Ser Asn Ser Cys Gln Asp Ser Thr Asp Thr Glu Ser
                245                     250                     255

AAC GCG GAG GAA CAG CGC AGC GGC CTT ATC TAC CTA ACC AAC CAC ATC                  816
Asn Ala Glu Glu Gln Arg Ser Gly Leu Ile Tyr Leu Thr Asn His Ile
            260                     265                     270

AAC CCG CAT GCA CGC AAT GGG CTG GCT CTC AAG GAG GAG CAG CGC GCC                  864
Asn Pro His Ala Arg Asn Gly Leu Ala Leu Lys Glu Glu Gln Arg Ala
        275                     280                     285

TAC GAG GTG CTG AGG GCG GCC TCA GAG AAC TCG CAG GAT GCC TTC CGT                  912
Tyr Glu Val Leu Arg Ala Ala Ser Glu Asn Ser Gln Asp Ala Phe Arg
    290                     295                     300

GTG GTC AGC ACG AGT GGC GAG CAG CTG AAG GTG TAC AAG TGC GAA CAC                  960
Val Val Ser Thr Ser Gly Glu Gln Leu Lys Val Tyr Lys Cys Glu His
305                     310                     315                     320

TGC CGC GTG CTC TTC CTG GAT CAC GTC ATG TAT ACC ATT CAC ATG GGC                 1008
Cys Arg Val Leu Phe Leu Asp His Val Met Tyr Thr Ile His Met Gly
                325                     330                     335

TGC CAT GGC TGC CAT GGC TTT CGG GAT CCC TTT GAG TGT AAC ATG TGT                 1056
Cys His Gly Cys His Gly Phe Arg Asp Pro Phe Glu Cys Asn Met Cys
            340                     345                     350

GGT TAT CAC AGC CAG GAC AGG TAC GAG TTC TCA TCC CAT ATC ACG CGG                 1104
Gly Tyr His Ser Gln Asp Arg Tyr Glu Phe Ser Ser His Ile Thr Arg
        355                     360                     365

GGG GAG CAT CGT TAC CAC CTG AGC                                                 1128
Gly Glu His Arg Tyr His Leu Ser
    370                     375
```

(2) INFORMATION FOR SEQ ID NO:7:

(i) SEQUENCE CHARACTERISTICS:
        (A) LENGTH: 1004 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1004

(xi) SEQUENCE DESCRIPTION: SEQ ID NO:7:

```
GGA GAA CGG CCC TTC CAG TGC AAT CAG TGC GGG GCC TCA TTC ACC CAG      48
Gly Glu Arg Pro Phe Gln Cys Asn Gln Cys Gly Ala Ser Phe Thr Gln
 1               5                  10                  15

AAG GGC AAC CTG CTC CGG CAC ATC AAG CTG CAT TCC GGG GAG AAG CCC      96
Lys Gly Asn Leu Leu Arg His Ile Lys Leu His Ser Gly Glu Lys Pro
             20                  25                  30

TTC AAA TGC CAC CTC TGC AAC TAC GCC TGC CGC CGG AGG GAC GCC CTC     144
Phe Lys Cys His Leu Cys Asn Tyr Ala Cys Arg Arg Arg Asp Ala Leu
         35                  40                  45

ACT GGC CAC CTG AGG ACG CAC TCC GTC ATT AAA GAA GAA ACT AAG CAC     192
Thr Gly His Leu Arg Thr His Ser Val Ile Lys Glu Glu Thr Lys His
     50                  55                  60

AGT GAA ATG GCA GAA GAC CTG TGC AAG ATA GGA TCA GAG AGA TCT CTC     240
Ser Glu Met Ala Glu Asp Leu Cys Lys Ile Gly Ser Glu Arg Ser Leu
 65                  70                  75                  80

GTG CTG GAC AGA CTA GCA AGT AAT GTC GCC AAA CGT AAG AGC TCT ATG     288
Val Leu Asp Arg Leu Ala Ser Asn Val Ala Lys Arg Lys Ser Ser Met
                 85                  90                  95

CCT CAG AAA TTT CTT GGG GAC AAG GGC CTG TCC GAC ACG CCC TAC GAC     336
Pro Gln Lys Phe Leu Gly Asp Lys Gly Leu Ser Asp Thr Pro Tyr Asp
            100                 105                 110

AGT GCC ACG TAC GAG AAG GAG AAC GAA ATG ATG AAG TCC CAC GTG ATG     384
Ser Ala Thr Tyr Glu Lys Glu Asn Glu Met Met Lys Ser His Val Met
        115                 120                 125

GAC CAA GCC ATC AAC AAC GCC ATC AAC TAC CTG GGG GCC GAG TCC CTG     432
Asp Gln Ala Ile Asn Asn Ala Ile Asn Tyr Leu Gly Ala Glu Ser Leu
    130                 135                 140

CGC CCG CTG GTG CAG ACG CCC CCG GGC GGT TCC GAG GTG GTC CCG GTC     480
Arg Pro Leu Val Gln Thr Pro Pro Gly Gly Ser Glu Val Val Pro Val
145                 150                 155                 160

ATC AGC CCG ATG TAC CAG CTG CAC AGG CGC TCG GAG GGC ACC CCG CGC     528
Ile Ser Pro Met Tyr Gln Leu His Arg Arg Ser Glu Gly Thr Pro Arg
                165                 170                 175

TCC AAC CAC TCG GCC CAG GAC AGC GCC GTG GAG TAC CTG CTG CTG CTC     576
Ser Asn His Ser Ala Gln Asp Ser Ala Val Glu Tyr Leu Leu Leu Leu
            180                 185                 190

TCC AAG GCC AAG TTG GTG CCC TCG GAG CGC GAG GCG TCC CCG AGC AAC     624
Ser Lys Ala Lys Leu Val Pro Ser Glu Arg Glu Ala Ser Pro Ser Asn
        195                 200                 205

AGC TGC CAA GAC TCC ACG GAC ACC GAG AGC AAC AAC GAG GAG CAG CGC     672
Ser Cys Gln Asp Ser Thr Asp Thr Glu Ser Asn Asn Glu Glu Gln Arg
    210                 215                 220

AGC GGT CTT ATC TAC CTG ACC AAC CAC ATC GCC CGA CGC GCG CAA CGC     720
Ser Gly Leu Ile Tyr Leu Thr Asn His Ile Ala Arg Arg Ala Gln Arg
225                 230                 235                 240

GTG TCG CTC AAG GAG GAG CAC CGC GCC TAC GAC CTG CTC CGC GCC GCC     768
Val Ser Leu Lys Glu Glu His Arg Ala Tyr Asp Leu Leu Arg Ala Ala
                245                 250                 255
```

```
TCC GAG AAC TCG CAG GAC GCG CTC CGC GTG GTC AGC ACC AGC GGG GAG      816
Ser Glu Asn Ser Gln Asp Ala Leu Arg Val Val Ser Thr Ser Gly Glu
            260                 265                 270

CAG ATG AAG GTG TAC AAG TGC GAA CAC TGC CGG GTG CTC TTC CTG GAT      864
Gln Met Lys Val Tyr Lys Cys Glu His Cys Arg Val Leu Phe Leu Asp
            275                 280                 285

CAC GTC ATG TAC ACC ATC CAC ATG GGC TGC CAC GGC TTC CGT GAT CCT      912
His Val Met Tyr Thr Ile His Met Gly Cys His Gly Phe Arg Asp Pro
            290                 295                 300

TTT GAG TGC AAC ATG TGC GGC TAC CAC AGC CAG GAC CGG TAC GAG TTC      960
Phe Glu Cys Asn Met Cys Gly Tyr His Ser Gln Asp Arg Tyr Glu Phe
305                 310                 315                 320

TCG TCG CAC ATA ACG CGA GGG GAG CAC CGC TTC CAC ATG AGC TA          1004
Ser Ser His Ile Thr Arg Gly Glu His Arg Phe His Met Ser
                325                 330                 335
```

(2) INFORMATION FOR SEQ ID NO:8:

(i) SEQUENCE CHARACTERISTICS:
        (A) LENGTH: 103 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
TTTGGTTATA AATGTATTGA TTGCATCCCC ATTACCCAGA AGGCCAATAT TTAATTGGAG     60

TCTTAACTCA ATTGTGTTTT CGTCAGTTGG TAAGCCTCAC AAA                      103
```

(2) INFORMATION FOR SEQ ID NO:9:

(i) SEQUENCE CHARACTERISTICS:
        (A) LENGTH: 116 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
ATGGGCCTTC CGGGCATGTA CCCAGGTAAG CACTGAGGCC CTGCTGAGCT GCACCCCTCC     60

CCCTCCCAGC GCCTGGGCCA GGATGGGGCT CTGTGGCCTG TTTCAGCCAC AGGAGG        116
```

(2) INFORMATION FOR SEQ ID NO:10:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
CCTTGTTGCT GCTGTGTTGC TATCTTGTGA CTTATTTTTG CAGTGACACT GAGTGGCCTC     60

CTGTGTTGTC TCTTTCAGCC AGTAATGTTA AAGT                                94
```

(2) INFORMATION FOR SEQ ID NO:11:

(i) SEQUENCE CHARACTERISTICS:
        (A) LENGTH: 120 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO:11:

GAGCCCTGGC AGATGTGTCC TGTCTGCTGT GACACTAGAA CACCATTCAA CCCCTGGGTG    60

TAGATTTCAC TTATGACCAT CTACTTCCCG CAGGAGACAA GTGCCTGTCA GACATGCCCT    120

(2) INFORMATION FOR SEQ ID NO:12:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

ACATGTGTGG TTATCACAGC CAGGACAGGT ACGAGTTCTC ATCCCATATC ACGCGGGGGG    60

AGCATCGTTA CCACCTGAGC TAAACCCAGC CAGGCCCCAC TGAAGCACAA AGATAGCTGG    120

(2) INFORMATION FOR SEQ ID NO:13:

(i) SEQUENCE CHARACTERISTICS:
        (A) LENGTH: 470 amino acids
        (B) TYPE: amino acid
        (C) STRANDEDNESS: single
        (D) TOPOLOGY: linear (ii) MOLECULE TYPE: peptide (v) FRAGMENT TYPE: C-terminal (xi) SEQUENCE DESCRIPTION: SEQ ID NO:13:

```
Xaa Xaa Ala Ser Asn Val Lys Val Glu Thr Gln Ser Asp Glu Glu Asn
  1               5                  10                  15

Gly Arg Ala Cys Glu Met Asn Gly Glu Glu Cys Ala Glu Asp Leu Arg
             20                  25                  30

Met Leu Asp Ala Ser Gly Glu Lys Met Asn Gly Ser His Arg Asp Gln
         35                  40                  45

Gly Ser Ser Ala Leu Ser Gly Val Gly Gly Ile Arg Leu Pro Asn Gly
     50                  55                  60

Lys Leu Lys Cys Asp Ile Cys Gly Ile Xaa Cys Ile Gly Pro Asn Val
 65                  70                  75                  80

Leu Met Val His Lys Arg Ser His Thr Gly Glu Arg Pro Phe Gln Cys
                 85                  90                  95

Asn Gln Cys Gly Ala Ser Phe Thr Gln Lys Gly Asn Leu Leu Arg His
            100                 105                 110

Ile Lys Leu His Ser Gly Glu Lys Pro Phe Lys Cys His Leu Cys Asn
        115                 120                 125

Tyr Ala Cys Arg Arg Arg Asp Ala Leu Thr Gly His Leu Arg Thr His
    130                 135                 140

Ser Val Gly Lys Pro His Lys Cys Gly Tyr Cys Gly Arg Ser Tyr Lys
145                 150                 155                 160

Gln Arg Xaa Ser Leu Glu Glu His Lys Glu Arg Cys His Asn Tyr Leu
                165                 170                 175

Glu Ser Met Gly Leu Pro Gly Xaa Xaa Xaa Pro Val Ile Lys Glu Glu
            180                 185                 190

Thr Xaa His Xaa Glu Met Ala Glu Asp Leu Cys Lys Ile Gly Xaa Glu
```

```
                195                 200                 205
Arg Ser Leu Val Leu Asp Arg Leu Ala Ser Asn Val Ala Lys Arg Lys
        210                 215                 220

Ser Ser Met Pro Gln Lys Phe Leu Gly Asp Lys Xaa Leu Ser Asp Xaa
225                 230                 235                 240

Pro Tyr Asp Ser Ala Xaa Tyr Glu Lys Glu Xaa Xaa Met Met Xaa Ser
                245                 250                 255

His Val Met Asp Xaa Ala Ile Asn Asn Ala Ile Asn Tyr Leu Gly Ala
            260                 265                 270

Glu Ser Leu Arg Pro Leu Val Gln Thr Pro Gly Xaa Ser Glu Val
        275                 280                 285

Val Pro Val Ile Ser Pro Met Tyr Gln Leu His Xaa Xaa Xaa Ser Xaa
290                 295                 300

Gly Xaa Pro Arg Ser Asn His Ser Ala Gln Asp Xaa Ala Val Xaa Xaa
305                 310                 315                 320

Leu Leu Leu Leu Ser Lys Ala Lys Xaa Val Xaa Ser Glu Arg Glu Ala
                325                 330                 335

Ser Pro Ser Asn Ser Cys Gln Asp Ser Thr Asp Thr Glu Ser Asn Xaa
                340                 345                 350

Glu Glu Gln Arg Ser Gly Leu Ile Tyr Leu Thr Asn His Ile Xaa Xaa
            355                 360                 365

Xaa Ala Xaa Xaa Xaa Xaa Xaa Leu Lys Glu Glu Xaa Arg Ala Tyr Xaa
    370                 375                 380

Xaa Leu Arg Ala Ala Ser Glu Asn Ser Gln Asp Ala Xaa Arg Val Val
385                 390                 395                 400

Ser Thr Ser Gly Glu Gln Xaa Lys Val Tyr Lys Cys Glu His Cys Arg
                405                 410                 415

Val Leu Phe Leu Asp His Val Met Tyr Thr Ile His Met Xaa Xaa Xaa
            420                 425                 430

Gly Cys His Gly Phe Arg Asp Pro Phe Glu Cys Asn Met Cys Gly Tyr
            435                 440                 445

His Ser Gln Asp Arg Tyr Glu Phe Ser Ser His Ile Thr Arg Gly Glu
        450                 455                 460

His Arg Xaa His Xaa Ser (2) INFORMATION FOR SEQ ID NO:14:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

AGAAGTTTCC ATAAGATGAT GAATGGGGGT GGCAGAGA                    38

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:
```

GGCTGCCACG GCTTCCGTGA TCCT                                           24

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

AGCGGTCTGG GGAAACATCT AGGA                                           24

(2) INFORMATION FOR SEQ ID NO:17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

AGTAATGTTA AAGTAGAGAC TCAG                                           24

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

GTATGACTTC TTTTGTGAAC CATG                                           24

(2) INFORMATION FOR SEQ ID NO:19:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

CCAGCCTCTG AGCCCAGAAA GCGA                                           24

(2) INFORMATION FOR SEQ ID NO:20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

CACTACCTCT GGAGCACAGC AGAA                                           24

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

GGTGAACGGC CTTTCCAGTG C                                              21

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

TCTGAGGCAT AGAGCTCTTA C                                              21

(2) INFORMATION FOR SEQ ID NO:23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

CATAGGGCAT GTCTGACAGG CACT                                           24

(2) INFORMATION FOR SEQ ID NO:24:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

TCAGCTTTTG GGAATGTCTT CCCTGTCA                                       28

(2) INFORMATION FOR SEQ ID NO:25:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

TCAGCTTTTG AGAATACCCT GTCA                                           24

(2) INFORMATION FOR SEQ ID NO:26:

(i) SEQUENCE CHARACTERISTICS:
        (A) LENGTH: 17 base pairs

```
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:26:

GGCATGACTC AGAGCGA                                                   17
```

Other embodiments are within the following claims.

What is claimed is:

1. A transgenic mouse whose genome has been altered by disrupting at least one exon of the endogenous Ikaros gene, wherein said disrupting is caused by the insertion of a DNA sequence, and wherein the altered genome results in said mouse exhibiting at least one of the following phenotypic characteristics:

a) the development of lymphomas,
   b) the lack of B cells as compared to a wild-type mouse,
   c) the lack of T cells as compared to a wild-type mouse,
   d) the lack of NK cells as compared to a wild-type mouse,
   e) a skewed population of CD4+/CD8+ cells as compared to a wild-type mouse,
   f) a decreased proportion of CD4+/CD8+ cells relative to a wild-type mouse,
   g) a skewed population of CD+/CD8– cells as compared to a wild-type mouse,
   h) an increased proportion of CD4+/CD8– cells relative to a wild-type mouse,
   i) a decreased ability to activate Ikaros-mediated transcription as compared to a wild-type mouse,
   j) an enlarged spleen as compared to a wild-type mouse,
   k) a decreased development of T cells as compared to a wild-type mouse,
   l) a decreased development of B cells as compared to a wild-type mouse,
   m) a decreased development of NK cells as compared to a wild-type mouse,
   n) the lack of immune responses mediated by T and B cells as compared to a wild-type mouse, or
   o) a severely immune-compromised state.

2. The transgenic mouse of claim 1, wherein said insertion is the result of any of an inversion, deletion, translocation, or reciprocal translocation.

3. The transgenic mouse of claim 1, wherein said insertion is in or alters the sequence, expression, or splicing of one or more of the following exons: exon 1/2, exon 3, exon 4, exon 5, exon 6, and exon 7.

4. The transgenic mouse of claim 1, wherein said insertion is in or alters the sequence, expression, or splicing of a DNA binding domain of the Ikaros gene.

5. The transgenic mouse of claim 1, wherein said insertion results in a deletion of portions of exon 3 and exon 4.

6. The transgenic mouse of claim 1, wherein said mouse is heterozygous for said insertion.

7. The transgenic mouse of claim 1, wherein said mouse is homozygous for said insertion.

8. The transgenic mouse of claim 1, wherein said altered genome of said mouse comprises said insertion and a second mutation in an Ikaros locus.

9. The transgenic mouse of claim 1, wherein said insertion is in a domain involved in transcriptional activation or in dimerization.

10. The transgenic mouse of claim 1, wherein said insertion is in exon 7.

11. The transgenic mouse of claim 1, wherein said insertion is in any of Zinc finger domains 1–6.

\* \* \* \* \*